US012669442B2

(12) United States Patent     (10) Patent No.:     US 12,669,442 B2
Yu et al.                          (45) **Date of Patent:      \*Jun. 30, 2026**

(54) WATER TEST PAPER AND MULTIFUNCTIONAL DETECTION TEST KIT

(71) Applicant: Lili Yu, Shenzhen City (CN)

(72) Inventors: Lili Yu, Shenzhen City (CN); Kuizi Wang, Shenzhen City (CN)

(73) Assignee: Lili Yu, Shenzhen City (CN)

( \* ) Notice:   Subject to any disclaimer, the term of this patent is extended or adjusted under 35 U.S.C. 154(b) by 0 days.

This patent is subject to a terminal disclaimer.

(21) Appl. No.: 19/062,036

(22) Filed:     Feb. 25, 2025

(65)             Prior Publication Data

US 2025/0369895 A1      Dec. 4, 2025

Related U.S. Application Data

(63) Continuation-in-part of application No. 18/957,829, filed on Nov. 24, 2024, which is a (Continued)

(30)        Foreign Application Priority Data

May 28, 2024   (CN) ......................... 202410674559.6
May 28, 2024   (CN) ......................... 202410674568.5
May 28, 2024   (CN) ......................... 202410674575.5

(51) Int. Cl.
  G01N 21/78        (2006.01)
  G01N 21/77        (2006.01)
       (Continued)

(52) U.S. Cl.
   CPC ............. *G01N 21/78* (2013.01); *G01N 33/18* (2013.01); *G01N 21/77* (2013.01);
       (Continued)

(58) Field of Classification Search
   CPC ........ G01N 21/77; G01N 21/78; G01N 21/80; G01N 2021/7759; G01N 33/18; G01N 33/1853; G01N 31/22; G01N 31/221; Y10T 436/145555; Y10T 436/147777; Y10T 436/148888; Y10T 436/16; Y10T 436/17; Y10T 436/173076; Y10T 436/19; Y10T 436/193333; Y10T 436/203332
   USPC .... 436/39, 77, 80, 84, 96, 98, 99, 103, 106, 436/110, 124, 125, 131, 163, 164, 165, 436/166, 169, 170; 422/400, 420, 421, 422/424, 430
   See application file for complete search history.

(56)               References Cited

U.S. PATENT DOCUMENTS 3,006,735  A  \*  10/1961  Jordan ................... G01N 31/22
                                                    422/403
3,730,688  A  \*   5/1973  Schmitt .................. G01N 31/22
                                                    422/420
                        (Continued)

*Primary Examiner* — Maureen Wallenhorst
(74) *Attorney, Agent, or Firm* — Che-Yang Chen

(57)               ABSTRACT

A multifunctional detection test kit includes a water test paper including a base and a plurality of test modules provided on different test zones of the base. Each of the test modules is configured to detect one of pH value, total alkalinity, cyanuric acid, total chlorine, bromine, free chlorine water hardness, lead, iron, copper, nitrite, nitrate, MPS, nickel, and phosphate.

19 Claims, 31 Drawing Sheets

Related U.S. Application Data continuation-in-part of application No. 18/925,094, filed on Oct. 24, 2024, and a continuation-in-part of application No. 18/925,089, filed on Oct. 24, 2024.

(51) Int. Cl.
 *G01N 21/80* (2006.01)
 *G01N 31/22* (2006.01)
 *G01N 33/18* (2006.01)

(52) U.S. Cl.
 CPC ..... *G01N 2021/7759* (2013.01); *G01N 21/80* (2013.01); *G01N 31/221* (2013.01); *G01N 33/1853* (2013.01)

(56) References Cited

U.S. PATENT DOCUMENTS

| | | | | |
|---|---|---|---|---|
| 3,796,543 A * | 3/1974 | Kamphake | ............. | G01N 31/02 436/103 |
| 4,301,115 A * | 11/1981 | Rapkin | ................. | G01N 31/22 435/805 |
| 4,855,239 A * | 8/1989 | Rupe | .................... | G01N 31/221 422/420 |
| 6,413,473 B1 * | 7/2002 | Bacon | .................... | G01N 31/22 436/166 |
| 2003/0102271 A1 * | 6/2003 | Howarth | ................. | C02F 1/766 210/764 |
| 2006/0182655 A1 * | 8/2006 | Zou | ........................ | B01L 3/5025 422/400 |
| 2009/0169630 A1 * | 7/2009 | Ward | ...................... | A61L 2/186 424/94.4 |
| 2011/0020943 A1 * | 1/2011 | Okamoto | ............... | G01N 31/22 427/256 |
| 2011/0143334 A1 * | 6/2011 | Roscoe | .................. | C12M 25/06 435/5 |
| 2014/0011283 A1 * | 1/2014 | Rudde | .................... | G01N 21/78 436/110 |
| 2014/0295568 A1 * | 10/2014 | Evtodienko | ............ | G01N 21/78 436/125 |
| 2014/0299526 A1 * | 10/2014 | Mastio | ..................... | G06G 1/08 210/85 |
| 2021/0172923 A1 * | 6/2021 | Kaufman | .............. | C07K 16/44 |

* cited by examiner

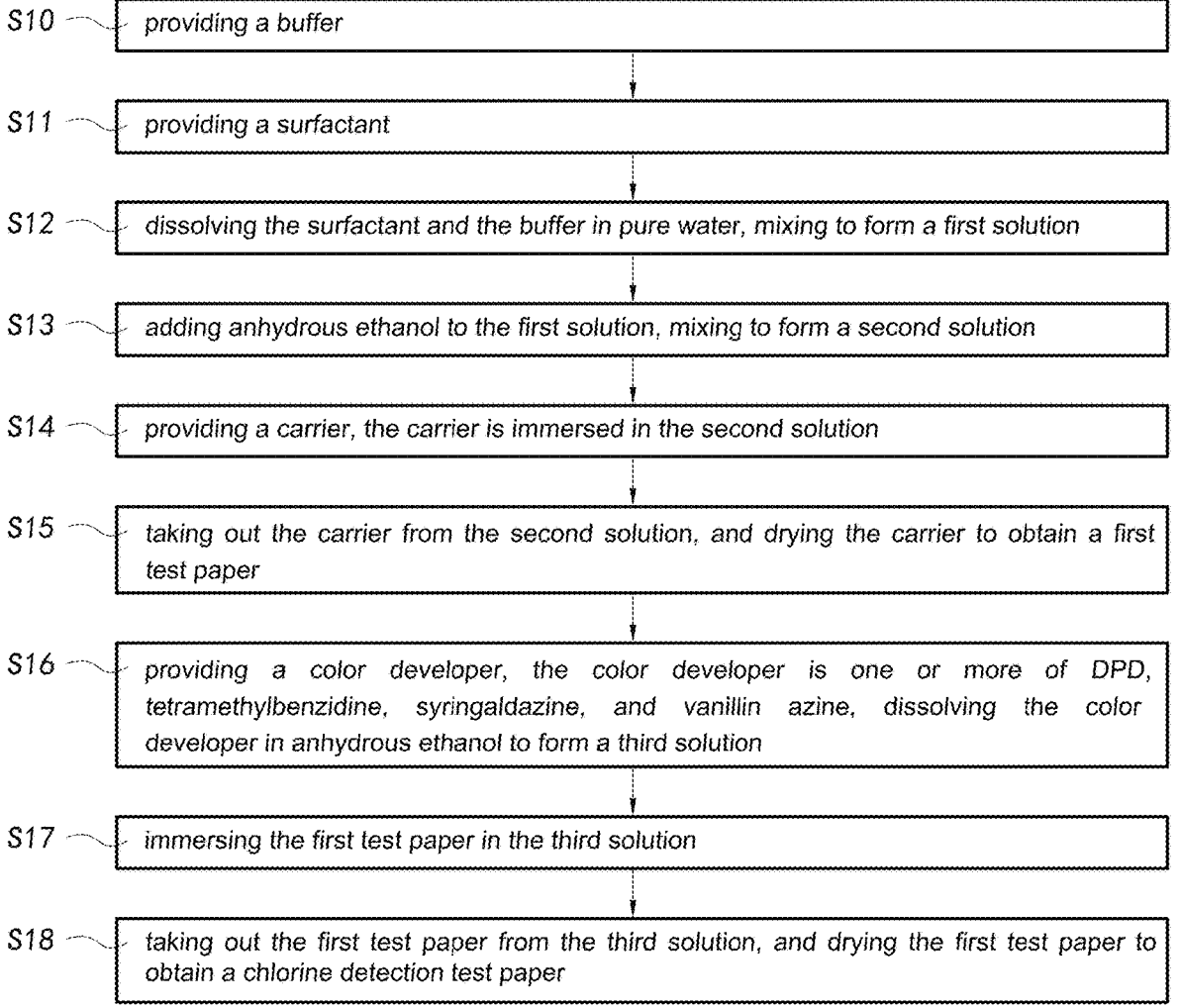

S10 —⤳ providing a buffer

S11 —⤳ providing a surfactant

S12 —⤳ dissolving the surfactant and the buffer in pure water, mixing to form a first solution S13 —⤳ adding anhydrous ethanol to the first solution, mixing to form a second solution S14 —⤳ providing a carrier, the carrier is immersed in the second solution S15 —⤳ taking out the carrier from the second solution, and drying the carrier to obtain a first test paper S16 —⤳ providing a color developer, the color developer is one or more of DPD, tetramethylbenzidine, syringaldazine, and vanillin azine, dissolving the color developer in anhydrous ethanol to form a third solution S17 —⤳ immersing the first test paper in the third solution S18 —⤳ taking out the first test paper from the third solution, and drying the first test paper to obtain a chlorine detection test paper

FIG.1

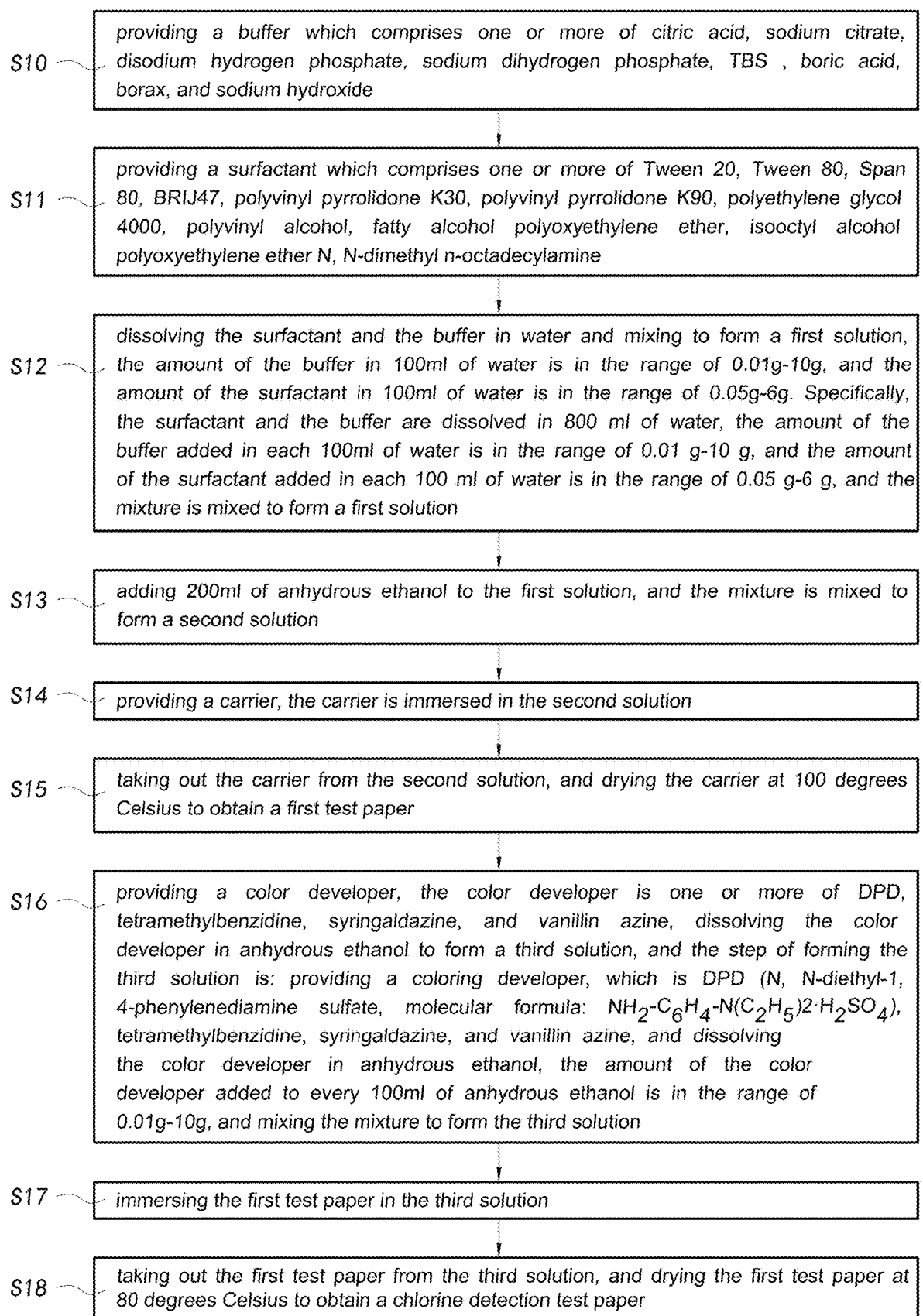

S10 — providing a buffer which comprises one or more of citric acid, sodium citrate, disodium hydrogen phosphate, sodium dihydrogen phosphate, TBS , boric acid, borax, and sodium hydroxide S11 — providing a surfactant which comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine S12 — dissolving the surfactant and the buffer in water and mixing to form a first solution, the amount of the buffer in 100ml of water is in the range of 0.01g-10g, and the amount of the surfactant in 100ml of water is in the range of 0.05g-6g. Specifically, the surfactant and the buffer are dissolved in 800 ml of water, the amount of the buffer added in each 100ml of water is in the range of 0.01 g-10 g, and the amount of the surfactant added in each 100 ml of water is in the range of 0.05 g-6 g, and the mixture is mixed to form a first solution S13 — adding 200ml of anhydrous ethanol to the first solution, and the mixture is mixed to form a second solution S14 — providing a carrier, the carrier is immersed in the second solution S15 — taking out the carrier from the second solution, and drying the carrier at 100 degrees Celsius to obtain a first test paper S16 — providing a color developer, the color developer is one or more of DPD, tetramethylbenzidine, syringaldazine, and vanillin azine, dissolving the color developer in anhydrous ethanol to form a third solution, and the step of forming the third solution is: providing a coloring developer, which is DPD (N, N-diethyl-1, 4-phenylenediamine sulfate, molecular formula: $NH_2\text{-}C_6H_4\text{-}N(C_2H_5)2\text{·}H_2SO_4$), tetramethylbenzidine, syringaldazine, and vanillin azine, and dissolving the color developer in anhydrous ethanol, the amount of the color developer added to every 100ml of anhydrous ethanol is in the range of 0.01g-10g, and mixing the mixture to form the third solution S17 — immersing the first test paper in the third solution S18 — taking out the first test paper from the third solution, and drying the first test paper at 80 degrees Celsius to obtain a chlorine detection test paper

FIG.2

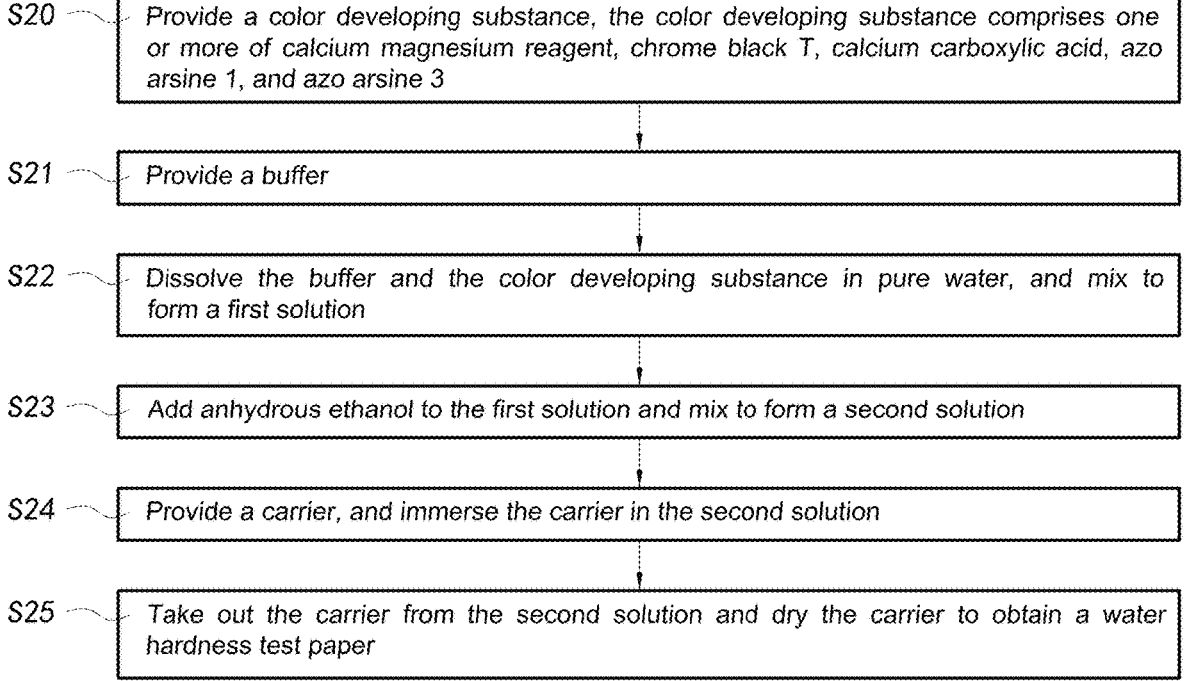

S20 — Provide a color developing substance, the color developing substance comprises one or more of calcium magnesium reagent, chrome black T, calcium carboxylic acid, azo arsine 1, and azo arsine 3

S21 — Provide a buffer

S22 — Dissolve the buffer and the color developing substance in pure water, and mix to form a first solution S23 — Add anhydrous ethanol to the first solution and mix to form a second solution S24 — Provide a carrier, and immerse the carrier in the second solution S25 — Take out the carrier from the second solution and dry the carrier to obtain a water hardness test paper

FIG.7

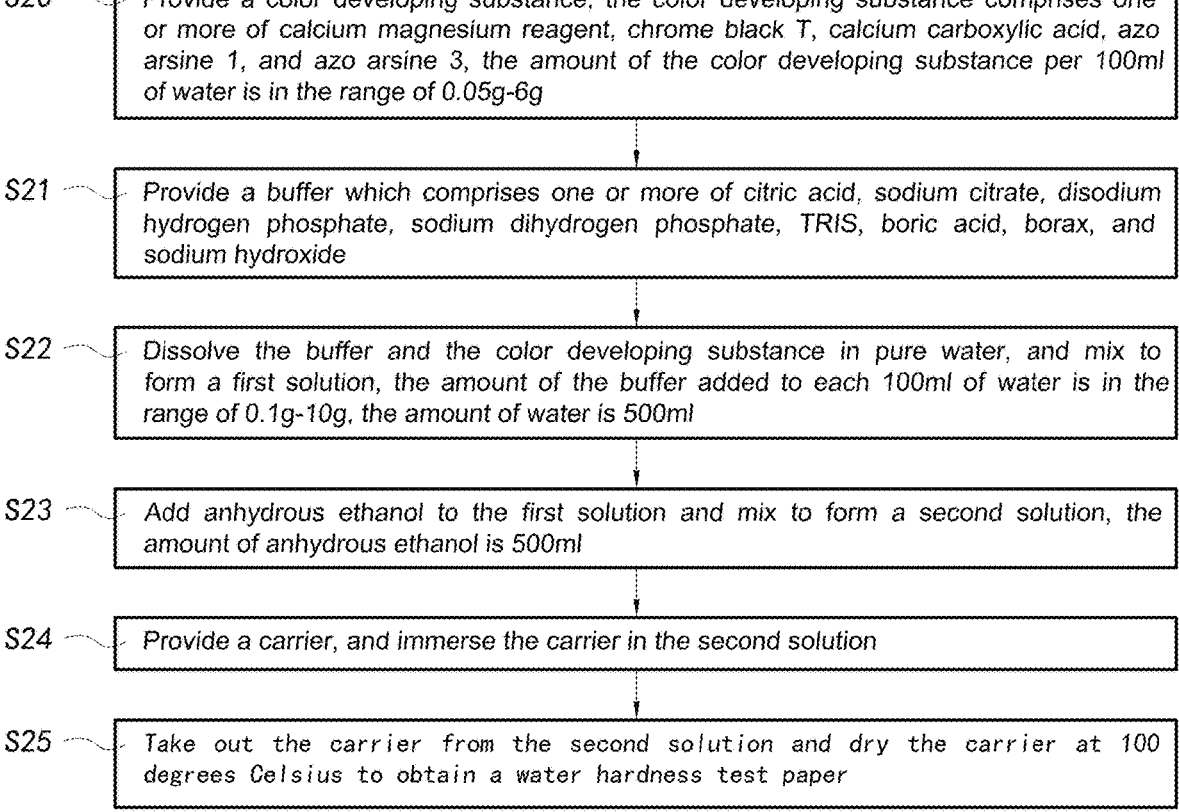

S20 — Provide a color developing substance, the color developing substance comprises one or more of calcium magnesium reagent, chrome black T, calcium carboxylic acid, azo arsine 1, and azo arsine 3, the amount of the color developing substance per 100ml of water is in the range of 0.05g-6g S21 — Provide a buffer which comprises one or more of citric acid, sodium citrate, disodium hydrogen phosphate, sodium dihydrogen phosphate, TRIS, boric acid, borax, and sodium hydroxide S22 — Dissolve the buffer and the color developing substance in pure water, and mix to form a first solution, the amount of the buffer added to each 100ml of water is in the range of 0.1g-10g, the amount of water is 500ml S23 — Add anhydrous ethanol to the first solution and mix to form a second solution, the amount of anhydrous ethanol is 500ml S24 — Provide a carrier, and immerse the carrier in the second solution S25 — Take out the carrier from the second solution and dry the carrier at 100 degrees Celsius to obtain a water hardness test paper

FIG.8

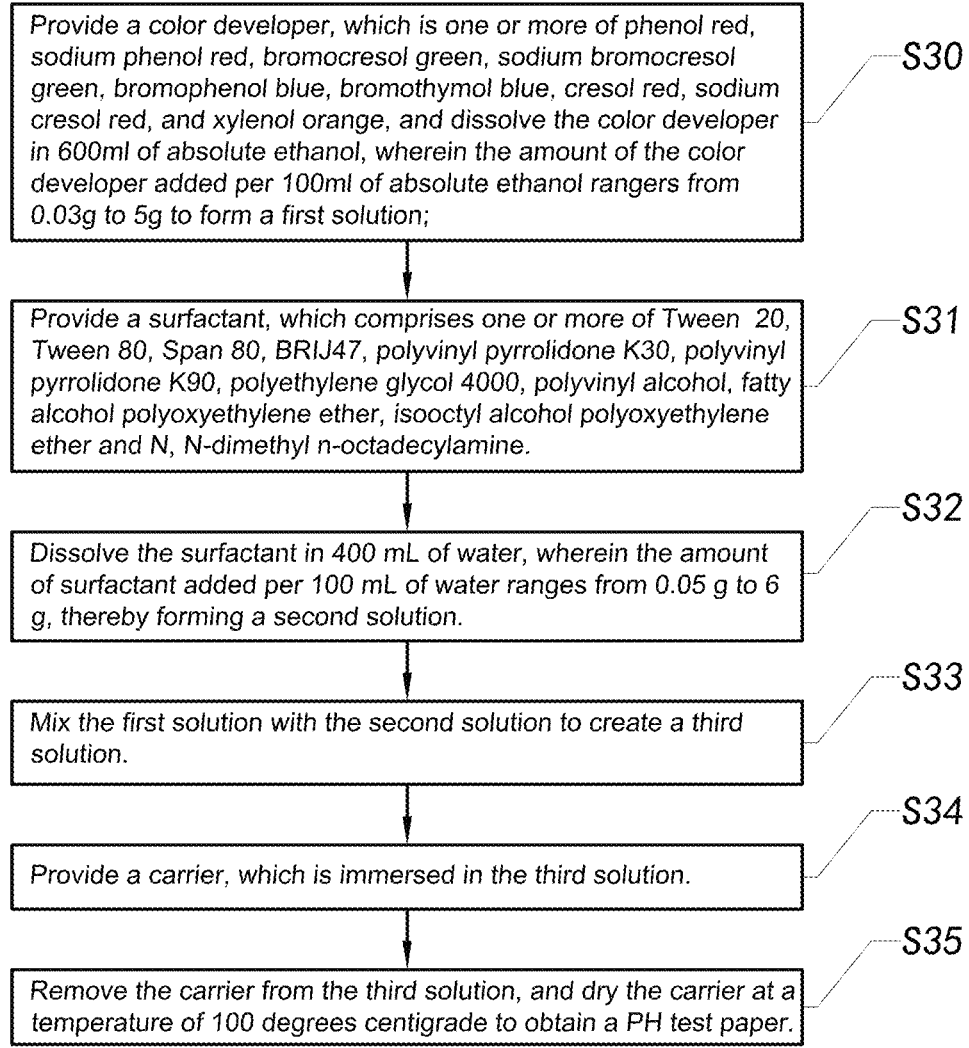

*Provide a color developer, which is one or more of phenol red, sodium phenol red, bromocresol green, sodium bromocresol green, bromophenol blue, bromothymol blue, cresol red, sodium cresol red, and xylenol orange, and dissolve the color developer in 600ml of absolute ethanol, wherein the amount of the color developer added per 100ml of absolute ethanol rangers from 0.03g to 5g to form a first solution;*                    S30

*Provide a surfactant, which comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.*                    S31

Dissolve the surfactant in 400 mL of water, wherein the amount of surfactant added per 100 mL of water ranges from 0.05 g to 6 g, thereby forming a second solution.                    S32

Mix the first solution with the second solution to create a third solution.                    S33

Provide a carrier, which is immersed in the third solution.                    S34

Remove the carrier from the third solution, and dry the carrier at a temperature of 100 degrees centigrade to obtain a PH test paper.                    S35

FIG.13

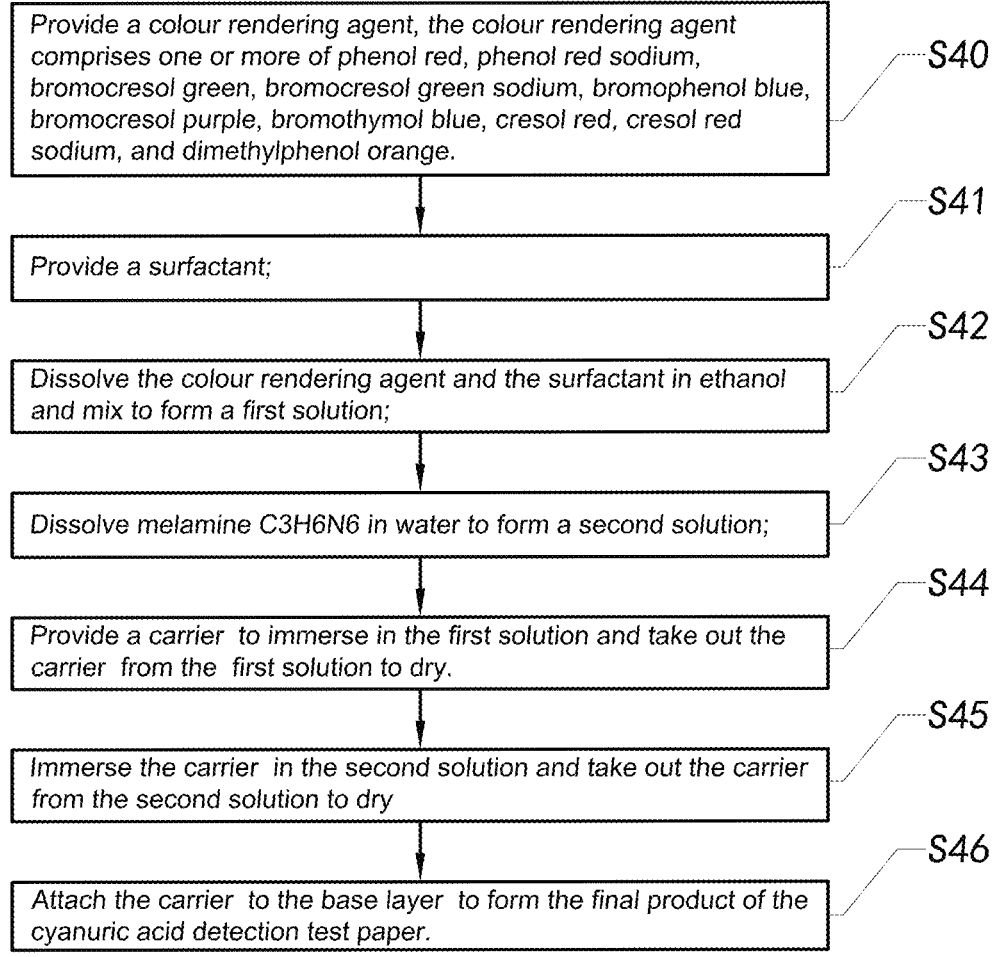

Provide a colour rendering agent, the colour rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

S40

Provide a surfactant;

S41

Dissolve the colour rendering agent and the surfactant in ethanol and mix to form a first solution;

S42

Dissolve melamine C3H6N6 in water to form a second solution;

S43

Provide a carrier to immerse in the first solution and take out the carrier from the first solution to dry.

S44

Immerse the carrier in the second solution and take out the carrier from the second solution to dry

S45

Attach the carrier to the base layer to form the final product of the cyanuric acid detection test paper.

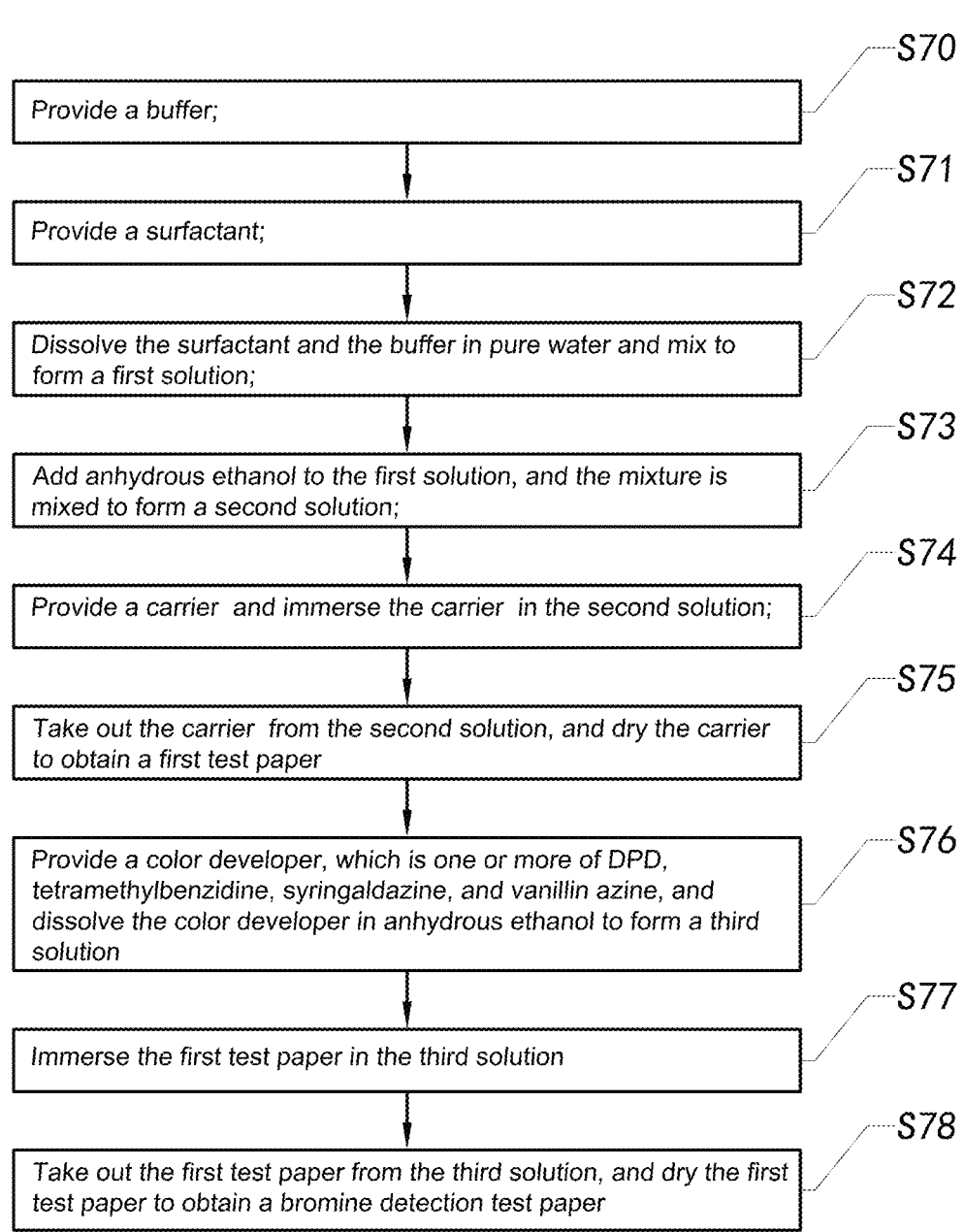
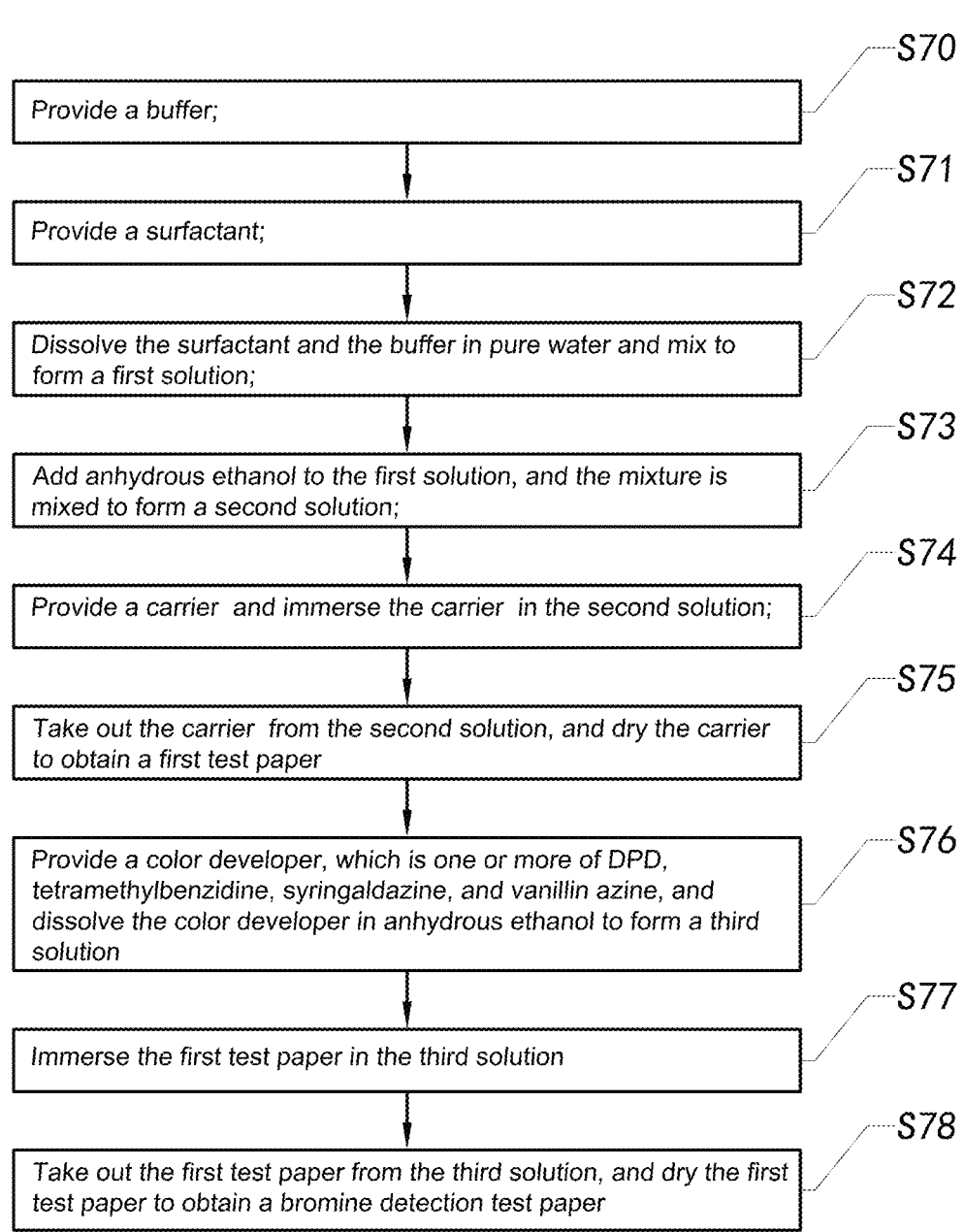
FIG.22

S91 — Provide a base 10g

S92 — Provide a plurality of test modules 20g, each test module 20g can detect one of pH, total alkalinity, cyanuric acid, total chlorine, bromine, free chlorine water hardness, lead, iron, copper, nitrite, nitrate, MPS, nickle, phosphate S93 — Attach the test modules 20g to the base 10g to obtain a multifunctional detection test paper

WATER TEST PAPER AND MULTIFUNCTIONAL DETECTION TEST KIT

CROSS REFERENCE OF RELATED APPLICATION

This application is a Continuation-In-Part application that claims the benefit of priority under 35 U.S.C. § 120 to a non-provisional application, application Ser. No. 18/957,829, filing date Nov. 24, 2024, which is a Continuation-In-Part application that claims the benefit of priority under 35 U.S.C. § 120 to a non-provisional application, application Ser. No. 18/925,094, filing date Oct. 24, 2024, which is a non-provisional application that claims priority under 35 U.S.C. § 119 to China application number CN202410674568.5, filing date May 28, 2024; Ser. No. 18/957,829 is also a Continuation-In-Part application that claims the benefit of priority under 35 U.S.C. § 120 to a non-provisional application, application Ser. No. 18/925,089, filing date Oct. 24, 2024, which is a non-provisional application that claims priority under 35 U.S.C. § 119 to China application number CN202410674575.5, filing date May 28, 2024; this application is also a non-provisional application that claims priority under 35 U.S.C. § 119 to China application number CN202410674559.6, filing date May 28, 2024, wherein the entire content of which is expressly incorporated herein by reference.

BACKGROUND OF THE PRESENT INVENTION

Field of Invention

The present invention relates to the field of water test paper, and more particular to a multifunctional detection test kit.

Description of Related Arts

Most of the tap water on the market currently uses chlorine for disinfection, but if the chlorine content in the water exceeds the standard, it will have serious consequences, such as: 1. Water with excessive chlorine content is very harmful to the human body, it will irritate the eyes, nose, throat respiratory tract, cause acute pulmonary edema, paralyze the nerves in the respiratory area when the concentration is high, and long-term inhalation of low-concentration chlorine will cause chronic poisoning; 2. Water with excessive chlorine content will destroy the vitamins, minerals and other nutrients in vegetables, fruits and grains, and seriously affect the absorption of nutrients by the human body; 3. Bathing with water with excessive chlorine content will cause itching in mild cases and increase the risk of cancer in severe cases; 4. After boiling water with excessive chlorine content, the organic humus in the water will produce carcinogens such as chloroform, and the carcinogens in the human body will increase; 5. Long-term drinking of water with excessive chlorine content will cause heart disease, coronary atherosclerosis, anemia, bladder cancer, liver cancer, rectal cancer, hypertension and allergy symptoms. Therefore, if users want to avoid using water with excessive chlorine content, they need to check the water to detect the chlorine content in the water. Therefore, there is an urgent need to provide a preparation method of a chlorine detection test paper and a chlorine detection test paper on the market to help users quickly and accurately detect the chlorine content in water.

Currently, the water hardness value of water is different. We should also pay attention to it when choosing drinking water, because they have different effects on the health of our body. Hardness is an important monitoring indicator of water quality. The total hardness of water is about 8, which is more suitable. By monitoring the water hardness value, we can know whether it can be used in industrial production and daily life. For example, water with high hardness can cause soap precipitation and greatly reduce the effectiveness of detergents. In the textile industry, water with too high hardness makes textiles rough and difficult to dye; burning boilers is easy to block pipes and cause boiler explosion accidents; high-hardness water is hard to drink and has a bitter taste. After drinking, it even affects gastrointestinal function; feeding livestock can cause miscarriage in pregnant animals, etc. Since consumers need to frequently test the water hardness value of drinking water to know whether the drinking water used is beneficial to health, there is an urgent need to provide a water hardness test paper and its preparing method on the market for users to detect the water hardness value of drinking water.

Currently, most tap water on the market uses chlorine for disinfection, but if the chlorine content in the water exceeds the standard, it will have serious consequences, such as: 1. Water with excessive chlorine content is very harmful to the human body and can irritate the eyes, nose, It can cause acute pulmonary edema in the throat and respiratory tract. When the concentration is high, it will paralyze the nerves in the respiratory area. Long-term inhalation of low-concentration chlorine will cause chronic poisoning; 2. Water with excessive chlorine content will destroy the vitamins, minerals and other nutrients in vegetables, fruits, and grains, seriously affecting the body's absorption of nutrients; 3. Taking a bath with water containing excessive chlorine may cause itching in mild cases, and increase the risk of cancer in severe cases; 4. When water containing excessive chlorine is boiled, organic decay in the water will produce three Methyl chloride and other carcinogens will increase the body's carcinogens; 5. Long-term drinking of water with excessive chlorine content will cause symptoms of heart disease, coronary atherosclerosis, anemia, bladder cancer, liver cancer, rectal cancer, hypertension and allergies. Therefore, if users want to avoid using water with excessive chlorine content, they need to check the water to detect the chlorine content in the water. Therefore, there is an urgent need on the market to provide a preparation method of chlorine detection test paper and chlorine detection test paper to help users quickly and accurately detect the chlorine content in water.

In addition, with water, there are some other statistics of water that we should be concerned about, which can affect our health, such as total alkalinity, cyanuric acid, lead, iron, copper, nitrite, nitrate, MPS, nickel, phosphate, total coliform bacteria and so on. There is an urgent need to provide such a test paper and its preparing method on the market for users to detect more than one data of water at a time, whether the water is for daily drinking or domestic use.

SUMMARY OF THE PRESENT INVENTION

The invention is advantageous in that is to provide a multifunctional detection test paper which can detect more than one data of water at a time.

Another advantage of the present invention is to provide a multifunctional detection test paper which can detect more than one data of water in a short time.

Another advantage of the present invention is to provide a multifunctional detection test paper which is very easy to use.

Another advantage of the present invention is to provide a multifunctional detection test paper which can provide results for several different parameters at the same time without interfering with each other.

Additional advantages and features of the invention will become apparent from the description which follows, and may be realized by means of the instrumentalities and combinations particularly pointing out in the appended claims.

According to the present invention, the foregoing and other objects and advantages are attained by a multifunctional detection test paper, comprising:

a base; and a plurality of test modules, each of the test modules being configured to detect at least one of a combination of pH, total alkalinity, cyanuric acid, total chlorine, bromine, free chlorine and water hardness; wherein the test modules are attached to the base.

According to an embodiment, the base comprises a base layer and a hydrophobic layer, wherein the hydrophobic layer is coated on the base layer, and the test modules are spaced apart on the hydrophobic layer, thereby preventing color bleeding.

According to an embodiment, one of the test modules is configured to detect free chlorine and comprises a carrier and a detection substance provided on the carrier, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine.

According to an embodiment, one of the test modules is configured to detect water hardness and comprises a carrier and a detection substance provided on the carrier, wherein the detection substance is formed by immersing the carrier in an immersing solution containing a color developer and a buffer, wherein the color developer comprises one or more of calcium magnesium reagent, chrome black T, calcium carboxylic acid, azo arsine 1, and azo arsine 3, wherein the buffer comprises one or more of citric acid, disodium EDTA, sodium citrate, disodium EDTA, disodium hydrogen phosphate, sodium dihydrogen phosphate, TRIS, boric acid, borax, and sodium hydroxide.

According to an embodiment, one of the test modules is configured to detect pH and comprises a carrier and a detection substance provided on the carrier, wherein the detection substance is formed by mixing a color developer and a surfactant, wherein the color developer comprises one or more of phenol red, sodium phenol red, bromocresol green, sodium bromocresol green, bromophenol blue, bromothymol blue, cresol red, sodium cresol red, and xylenol orange, wherein the surfactant comprises one or more of Tween 20, Tween 80, Span 80, BRIJ 47, polyvinylpyrrolidone K30, polyvinylpyrrolidone K90, polyethylene glycol 4000, polyvinyl alcohol, fatty alcohol ethoxylate, isooctyl alcohol ethoxylate N, and N,N-dimethyloctadecylamine.

According to an embodiment, one of the test modules is configured to detect cyanuric acid and comprises a carrier and a detection substance provided on the carrier, wherein the detection substance is formed by mixing a color rendering agent, a surfactant and melamine, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, and isooctanol polyoxyethylene ether N,N-dimethyldioctadecylamine.

According to an embodiment, one of the test modules is configured to detect total alkalinity and comprises a carrier and a detection substance provided on the carrier, wherein the detection substance is formed by mixing a color rendering agent and a surfactant, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

According to an embodiment, one of the test modules is configured to detect total chlorine and comprises a carrier and a detection substance provided on the carrier, wherein the detection substance is formed by mixing a buffer, a surfactant and a color developer, wherein the buffer comprises one or more of citric acid, sodium citrate, disodium hydrogen phosphate, sodium dihydrogen phosphate, TBS, boric acid, borax, and sodium hydroxide, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine, wherein the color developer comprises one or more of DPD, tetramethylbenzidine, syringaldazine, and vanillin azine.

According to an embodiment, one of the test modules is configured to detect bromine and comprises a carrier and a detection substance provided on the carrier, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine.

According to an embodiment, the base layer is made of Polyethylene Terephthalate.

According to an embodiment, the hydrophobic layer is formed by coating a coating solution on the base layer, wherein the coating solution is mixed by a organosilicon compound, a modifying agent and a molding agent, wherein the organosilicon compound comprises one or more of silicon dioxide, dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises on e or more of sodium hydroxide, lithium hydroxide, ammonia, sodium bicarbonate, sodium acetate, sodium citrate, and potassium citrate.

According to the present invention, the foregoing and other objects and advantages are attained by a preparing method of a multifunctional detection test paper, comprising the following steps:

providing a base;

providing a plurality of test modules, each of the test modules being configured to detect at least one of a combination of PH, total alkalinity, cyanuric acid, total chlorine, bromine, free chlorine and water hardness; and Attaching the test modules to the base to obtain a multifunctional detection test paper.

According to an embodiment, the step of providing the base further comprises the following steps providing a base layer; and forming a hydrophobic layer with the base layer.

According to an embodiment, the step of forming the hydrophobic layer with the base layer further comprises the following steps:

providing a coating solution; and coating the coating solution on the base layer to form the base with the hydrophobic layer.

According to an embodiment, the coating solution is mixed by an organosilicon compound, a modifying agent and a molding agent, wherein the organosilicon compound comprises one or more of silicon dioxide, dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises on e or more of sodium hydroxide, lithium hydroxide, ammonia, sodium bicarbonate, sodium acetate, sodium citrate, and potassium citrate.

According to the present invention, the foregoing and other objects and advantages are attained by a multifunctional detection test paper which is prepared by a method comprising the following steps:

providing a base;

providing a plurality of test modules, each of the test modules being configured to detect at least one of a combination of PH, total alkalinity, cyanuric acid, total chlorine, bromine, free chlorine and water hardness; and Attaching the test modules to the base to obtain a multifunctional detection test paper.

According to an embodiment, the base comprises a base layer and a hydrophobic layer, wherein the hydrophobic layer is coated on the base layer, and the test modules are spaced apart on the hydrophobic layer, thereby preventing color bleeding.

According to an embodiment, the hydrophobic layer is formed by coating a coating solution on the base layer, wherein the coating solution is mixed by a organosilicon compound, a modifying agent and a molding agent, wherein the organosilicon compound comprises one or more of silicon dioxide, dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises on e or more of sodium hydroxide, lithium hydroxide, ammonia, sodium bicarbonate, sodium acetate, sodium citrate, and potassium citrate.

According to the present invention, the foregoing and other objects and advantages are attained by a method of testing water quality, comprising the following steps:

immersing a plurality of test modules of a multifunctional detection test paper into water, each of the test modules being configured to detect at least one of a combination of PH, total alkalinity, cyanuric acid, total chlorine, bromine, free chlorine and water hardness;

removing the multifunctional detection test paper from water and placing it horizontally for a predetermined period; and comparing the colors of the test modules of the multifunctional detection test paper with a color reference.

According to an embodiment, the method of testing water quality further comprises a step of:

preventing cross-contamination of colors between the respective test modules by using a hydrophobic layer as water flows along the multifunctional detection test paper to each of the test modules.

The present invention further provides a multifunctional detection test kit for water, comprising a multifunctional detection test paper which comprises a base and a plurality of test modules, wherein each of the test modules is configured to detect one of pH, total alkalinity, cyanuric acid, total chlorine, bromine, free chlorine water hardness, lead, iron, copper, nitrite, nitrate, MPS, nickel, and phosphate, wherein the test modules are attached to the base.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

In order to more clearly illustrate the technical solutions in the embodiments of the present invention, the drawings required for use in the description of the embodiments will be briefly introduced below. The drawings described below are only some embodiments of the present invention. For ordinary technicians in this field, other drawings can also be obtained based on these drawings without creative work.

The present invention is further described below in conjunction with the accompanying drawings and embodiments.

FIG. 1 is a schematic diagram of the overall process of a first preferred embodiment of the present invention.

FIG. 2 is another schematic diagram of the overall process of the first preferred embodiment of the present invention.

FIG. 7 is a schematic diagram illustrating the preparing method of a water hardness test paper according to a first preferred embodiment of the present invention.

FIG. 8 is another schematic diagram illustrating the preparing method of the water hardness test paper according to the above first preferred embodiment of the present invention.

FIG. 13 It is another overall flow diagram of the present invention.

FIG. 16 is a schematic diagram of the overall process of the present invention.

FIG. 22 is a schematic diagram of the overall process of the present invention.

DETAILED DESCRIPTION OF THE PREFERRED EMBODIMENT

Figure 3:
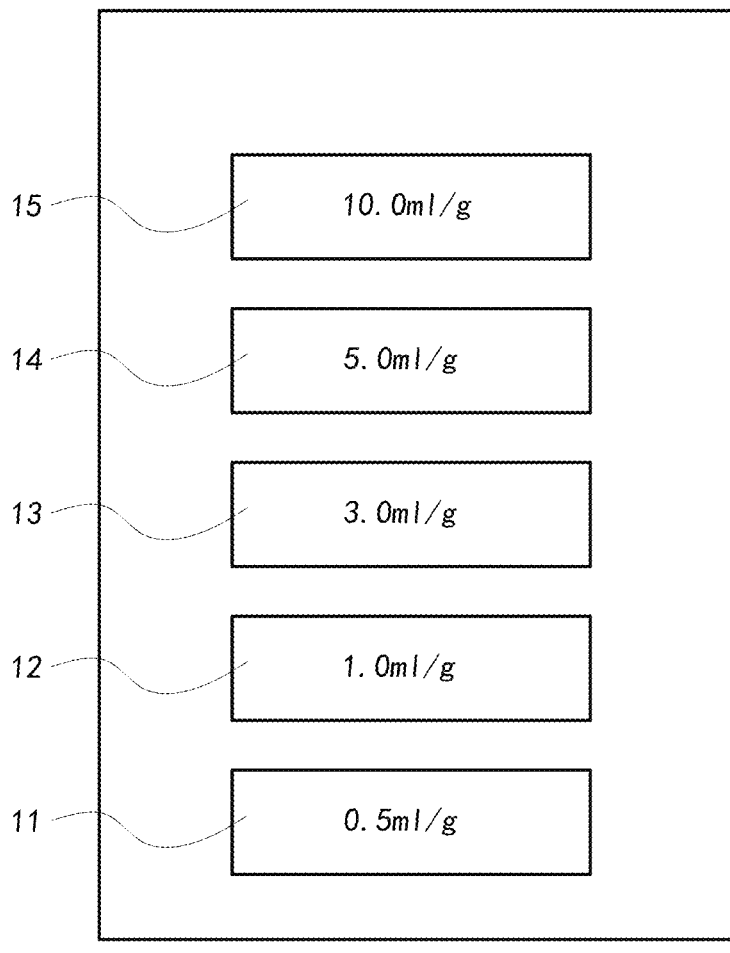
FIG. 3 is a schematic diagram of the structure of the comparison color card of the first preferred embodiment of the present invention.
Figure 4:
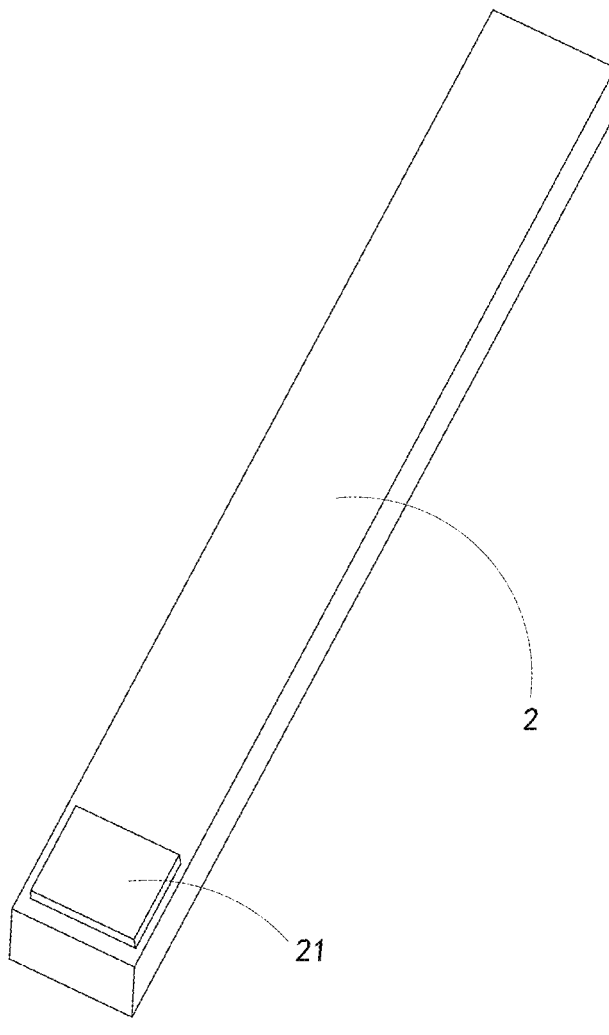
FIG. 4 is a perspective view illustrating the overall structure of a chlorine detection test paper of the first preferred embodiment of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

With reference to FIGS. 1 to 4, a method for preparing a free chlorine detection test paper comprises the following steps.

Step S10: Provide a buffer.

In this step, the buffer comprises one or more of citric acid, sodium citrate, disodium hydrogen phosphate, sodium dihydrogen phosphate, TBS (Tris Buffered Saline, trishydroxymethylaminomethane Buffered Saline), boric acid, borax, and sodium hydroxide. Through the above steps, the buffer can improve the color response of the color developer to free available chlorine, and provide a more stable color response, and the buffer can be complexed with the color developer to form a brighter and more gorgeous color, and stabilize the color.

Step S11: Provide a surfactant.

In this step, the surfactant is one or more of Tween 20, Tween 80, Span 80, BRIJ47 (polyoxyethylene), polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine. Through the above step, the surfactant helps the test sample to wet the carrier 2 without adversely affecting the color transition of the color-developing substance in response to free available chlorine. In addition, the surfactant can also improve the stability of the color transition of the color-developing substance.

Step S12: Dissolve the surfactant and the buffer in pure water and mix to form a first solution.

In this step, dissolve the surfactant and the buffer in water and mix to form a first solution, the amount of the buffer in 100 ml of water is in the range of 0.01 g-10 g, and the amount of the surfactant in 100 ml of water is in the range of 0.05 g-6 g. Specifically, the surfactant and the buffer are dissolved in 800 ml of water, the amount of the buffer added in each 100 ml of water is in the range of 0.01 g-10 g, and the amount of the surfactant added in each 100 ml of water is in the range of 0.05 g-6 g, and the mixture is mixed to form a first solution.

Step S13: Add anhydrous ethanol to the first solution, and the mixture is mixed to form a second solution.

In this step, 200 ml of anhydrous ethanol is added to the first solution, and the mixture is mixed to form a second solution.

Step S14: Provide a carrier 2 and immerse the carrier 2 in the second solution.

Step S15: Take out the carrier 2 from the second solution, and dry the carrier 2 to obtain a first test paper.

In this step, the carrier 2 is taken out from the second solution, and the carrier 2 is dried at 100 degrees Celsius to obtain a first test paper.

Step S16: Provide a color developer, which is one or more of DPD, tetramethylbenzidine, syringaldazine, and vanillin azine, and dissolving the color developer in anhydrous ethanol to form a third solution.

In this step, a color developer, which comprises one or more of DPD, tetramethylbenzidine, syringaldazine, and vanillin azine, is provided, and the color developer is dissolved in anhydrous ethanol, and the step of forming the third solution is: providing a coloring developer, which is DPD (N, N-diethyl-1,4-phenylenediamine sulfate, molecular formula: $NH_2$—$C_6H_4$—$N(C_2H_5)_2 \cdot H_2SO_4$), tetramethylbenzidine, syringaldazine, and vanillin azine, and dissolving the color developer in anhydrous ethanol, the amount of the color developer added to every 100 ml of anhydrous ethanol is in the range of 0.01 g-10 g, and mixing the mixture to form the third solution.

Step S17: Immerse the first test paper in the third solution.

Step S18: Take out the first test paper from the third solution, and dry the first test paper to obtain a chlorine detection test paper.

In this step, take out the first test paper from the third solution, and dry the first test paper at 80 degrees Celsius to obtain a chlorine detection test paper.

Through the above steps, the present invention provide a method for preparing a chlorine detection test paper, wherein the method comprises the following steps: providing a buffer; providing a surfactant; dissolving the surfactant and the buffer in pure water, mixing to form a first solution; adding anhydrous ethanol to the first solution, mixing to form a second solution; providing a carrier 2, immersing the carrier 2 in the second solution; taking out the carrier 2 from the second solution, and drying the carrier 2 to obtain a first test paper; providing a color developer, the color developer comprises one or more of DPD, tetramethylbenzidine, syringaldazine, and vanillinazine, dissolving the color developer in anhydrous ethanol to form a third solution; immersing the first test paper in the third solution; taking out the first test paper from the third solution, and drying the first test paper to obtain a chlorine detection test paper, so that a user can put the chlorine detection test paper into water for detection, and the color developer reacts with active chlorine in water to generate a purple-red compound, the color depth of which is proportional to the chlorine concentration, and it can be compared with a color card to accurately detect the chlorine content in water. The buffer can improve the color response of the color developer to free available chlorine and provide a more stable color response, and the buffer can be complexed with the color developer to form a brighter and more gorgeous color and stabilize the color. Specifically, the surfactant helps the test sample to wet the carrier without adversely affecting the color transition of the color developer in response to free available chlorine. In addition, the surfactant can also improve the stability of the color transition of the color developer. The comparison color card includes a first purple-red color block, a second purple-red color block, a third purple-red color block, a fourth purple-red color block, and a fifth purple-red color block, and the first purple-red color block, the second purple-red color block, the third purple-red color block, the fourth purple-red color block, and the fifth purple-red color block are arranged in sequence from bottom to top along the color card, and the color depth of the first purple-red color block, the second purple-red color block, the third purple-red color block, the fourth purple-red color block, and the fifth purple-red color block increases in sequence, wherein the detection result corresponding to the first purple-red color block is 0.5 mg/L, the detection result corresponding to the second purple-red color block is 1.0 mg/L, the detection result corresponding to the third purple-red color block is 3.0 mg/L, the detection result corresponding to the fourth purple-red color block is 5.0 mg/L, and the detection result corresponding to the fifth purple-red color block is 10 mg/L.

Referring to FIGS. 1 to 4, the present invention also provides a chlorine detection test paper comprising a carrier 2, a chlorine detection layer is provided on the carrier 2, and the chlorine detection layer is used to react with chlorine and develop color, and a filtering paper 21 is also provided on the carrier 2. The area of filtering paper 21 accounts for 4%-7% of the area of carrier 2. Specifically, the width range of carrier 2 is 3-7 mm, and the length range of carrier 2 is 60-110 mm. Further, the width range of filtering paper 21 is 3-7 mm, the length range of filtering paper 21 is 3-8 mm, and the thickness of filtering paper 21 is 0.1 mm-0.8 mm. Further, the chlorine detection layer is used to react with chlorine and develop color, and the chlorine detection layer is formed by mixing chlorine coloring matter, buffer and surfactant. Further, the chlorine coloring matter is a color developer comprises one or more of DPD, tetramethylbenzidine, syringaldehyde azine, and vanillin azine. Further, the buffer is one or more of citric acid, sodium citrate, disodium hydrogen phosphate, sodium dihydrogen phosphate, TRIS, boric acid, borax, and sodium hydroxide. Furthermore, the surfactant is one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine.

Through the above structure, the color developer reacts with the active chlorine in the water to generate a purple-red compound, the color depth of which is proportional to the chlorine concentration, and it can be compared with the color card to accurately detect the chlorine content in the water. Among them, the buffer can improve the color response of the color developer to free available chlorine and provide a more stable color response, and the buffer can complex with the color developer to form a brighter, more gorgeous color and stabilize the color. Specifically, the surfactant helps the test sample to wet the carrier 2 without adversely affecting the color change of the color developer in response to free available chlorine. In addition, the surfactant can also improve the stability of the color transition of the color developer. In addition, the size design of the above-mentioned carrier and filtering paper is reasonable, which is convenient for the production and packaging of pH test strips, and the color development effect is better.

Figure 5:
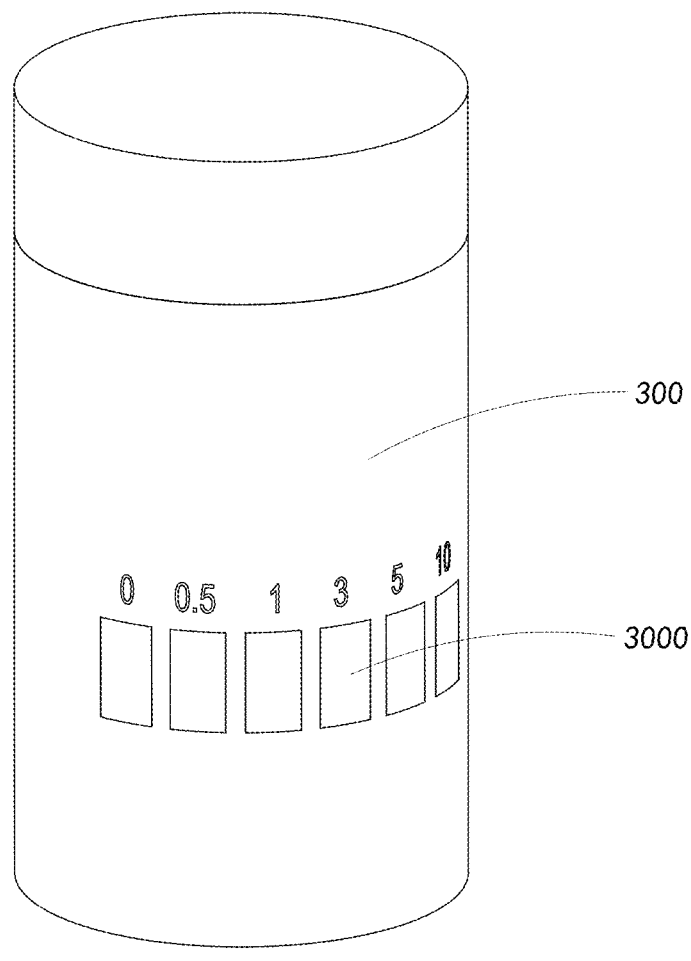
FIG. 5 is a perspective view illustrating a container storing the chlorine detection test paper of a second preferred embodiment of the present invention.
Figure 6:
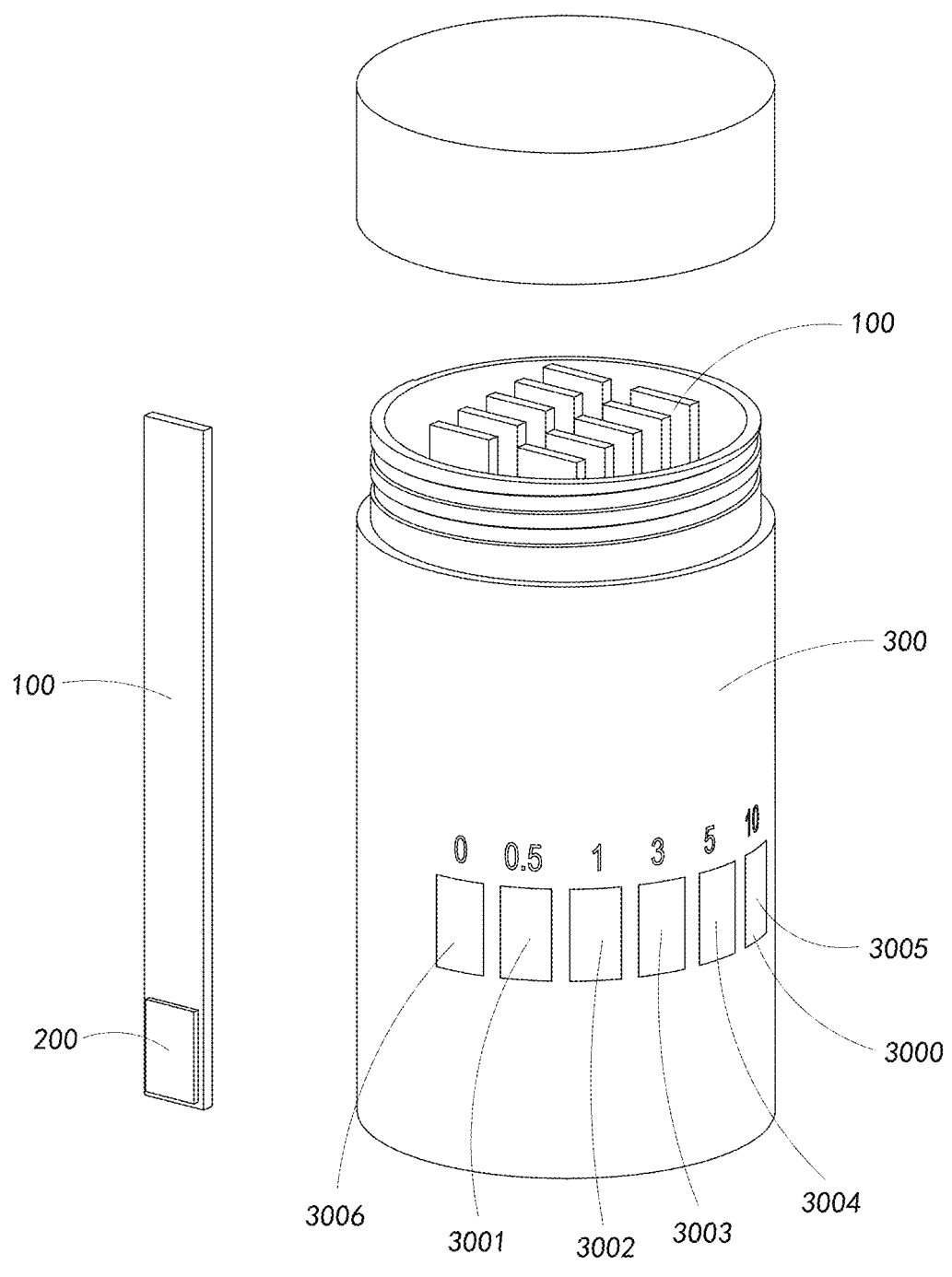
FIG. 6 is an exploded view illustrating the container storing with the chlorine detection test paper of the second preferred embodiment of the present invention.

Referring to FIGS. 5 to 6 of the drawings, a chlorine detection test paper according to a second preferred embodiment of the present invention is illustrated. The chlorine detection test paper comprises a base layer 100, and a carrier 200 attached to the base layer 100 for carrying a chlorine detection substance.

The chlorine detection test paper for water quality detection can be used in various applications, including domestic water, swimming pools, aquariums, and disinfection. This type of test paper is commonly employed to measure chlorine levels, ensuring water safety and cleanliness. Beyond these areas, chlorine detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100 is made of a polymer material such as PET (Polyethylene Terephthalate), PEN (Polyethylene Naphthalate), PP (Polypropylene), and PE (Polyethylene). In this embodiment, the base layer 100 is made of PET.

PET is known for its excellent mechanical strength, providing a robust and durable base layer that can withstand handling and environmental stress during use and storage. PET exhibits strong resistance to chemicals, including acids and bases. This characteristic ensures that the base layer 100 does not degrade or react when exposed to various substances, preserving the integrity of the chlorine detection test paper.

PET has low shrinkage and maintains its dimensions under different environmental conditions, such as changes in temperature and humidity. This stability is crucial for the consistent performance of the test paper. PET also offers excellent barrier properties against moisture and gases, protecting the chlorine detection substance from premature degradation due to exposure to air or moisture. This extends the shelf life and reliability of the test paper.

PET can be widely used in manufacturing due to its ease of processing. It can be easily extruded, laminated, or coated, making it a versatile material for creating a consistent and high-quality base layer 100.

The carrier 200 is used for being immersed in the immersing solutions to carry the chlorine detection substance. In this embodiment, the carrier 200 is made of a filtering paper. Accordingly, the filtering paper is designed to absorb liquids efficiently, ensuring that the immersing solution, which contains the chlorine detection substance, is evenly distributed across the carrier 200. This uniform absorption is crucial for consistent test results.

The filtering paper has a porous structure, which allows it to hold and distribute the chlorine detection substance effectively. The porosity ensures that the test paper has sufficient surface area for the chlorine in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the chlorine detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The chlorine detection substance on the carrier 200 comprises a color developer which comprises one or more of DPD, tetramethylbenzidine, syringaldehyde azine, and vanillin azine.

Preferably, the chlorine detection substance is formed by mixing chlorine color developer, buffer and surfactant, the chlorine color developer comprises one or more of DPD, tetramethylbenzidine, syringaldazine and vanillinazine; the buffer comprises one or more of citric acid, sodium citrate, disodium hydrogen phosphate, sodium dihydrogen phosphate, TRIS, boric acid, borax and sodium hydroxide; the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N,N-dimethyl n-octadecylamine.

The use of one or more developers like DPD, tetramethylbenzidine, syringaldazine, and vanillinazine ensures a sensitive and precise colorimetric response to chlorine. These developers produce distinct and easily observable color changes upon reacting with chlorine, allowing for accurate detection across a range of chlorine concentrations.

The inclusion of the buffer, comprising compounds such as citric acid, sodium citrate, disodium hydrogen phosphate, sodium dihydrogen phosphate, TRIS, boric acid, borax, and sodium hydroxide, is crucial for maintaining a stable pH environment. This stabilization ensures that the chlorine color developers react consistently, providing reliable and reproducible results. The buffer also helps to enhance the intensity and stability of the color change, making the detection process more robust.

The addition of surfactants like Tween 20, Tween 80, Span 80, BRIJ47, polyvinyl pyrrolidone (K30, K90), polyethylene glycol 4000, polyvinyl alcohol, fatty alcohol polyoxyethylene ether, isooctyl alcohol polyoxyethylene ether, and N,N-dimethyl n-octadecylamine aids in improving the wetting properties of the detection substance. These surfactant ensures that the chlorine detection substance is evenly distributed on the carrier 200, leading to consistent and uniform test results. The surfactant also helps in preventing the aggregation of the color developers, further enhancing the accuracy of the detection.

The use of carefully selected buffer and surfactant contributes to the overall stability of the chlorine detection substance. By preventing the degradation of the color developers and ensuring a stable pH environment, the formulation is protected against environmental factors such as temperature fluctuations and humidity. This leads to an extended shelf life, making the detection substance more reliable over time.

The present invention further provides a container 300 for storing a plurality of the chlorine detection test paper, and a plurality of color blocks 3000 are painted on an outer surface of the container 300 for indicating the concentration levels of chlorine.

In this embodiment, the plurality of color blocks 3000 comprises a first purple-red color block 3001, a second purple-red color block 3002, a third purple-red color block 3003, a fourth purple-red color block 3004, a fifth purple-red color block 3005, and a sixth purple-red color block 3006. The detection result corresponding to the sixth purple-red color block 3006 is 0 mg/L, the detection result corresponding to the first purple-red color block 3001 is 0.5 mg/L, the detection result corresponding to the second purple-red color block 3002 is 1.0 mg/L, the detection result corresponding to the third purple-red color block 3003 is 3.0 mg/L, the detection result corresponding to the fourth purple-red color block 3004 is 5.0 mg/L, and the detection result corresponding to the fifth purple-red color block 3005 is 10 mg/L.

The inclusion of color blocks 3000 directly on the container 300 provides an easy and immediate reference for users to compare the color change of the test paper with the standard color blocks. This feature simplifies the process of interpreting test results, as users can directly compare the test paper to the color blocks on the container without needing a separate reference card.

The color blocks 3000 being painted on the container 300 ensure that the reference guide is always available with the test papers. This design reduces the risk of misplacing or losing the color reference, making the test kit more user-friendly and accessible, especially in field conditions.

By incorporating a range of purple-red color blocks 3000 that correspond to specific chlorine concentration levels, the design offers clear visual differentiation between different concentrations. This clarity helps users more accurately determine chlorine levels, even in situations where precise readings are critical.

Since the color blocks 3000 are painted on the container 300, they are less likely to be damaged or worn compared to a separate paper reference card. This increases the durability of the test kit, ensuring that the reference guide remains intact and legible over time. The color blocks 300 may be painted on an outer surface of the container 300, or the color blocks 300 are painted on a paper sheet and the paper sheet is then attached on the container body of the container 300.

Combining the test paper storage and the color reference in one container makes the entire testing kit more compact and portable. Users can carry the container with them easily, knowing that they have everything needed for chlorine testing in one convenient package.

The present invention further provides a method for preparing the chlorine detection test paper, and the method comprises the steps of immersing the carrier 200 in a first immersing solution and immersing the carrier 200 in a second immersing solution.

In the step of immersing the carrier 200 in the first immersing solution the surfactant and the buffer are dissolved in water and mixed, and anhydrous ethanol is then added and mixed to obtain the first immersing solution, the amount of the buffer in 100 ml of water is in the range of 0.01 g-10 g, and the amount of the surfactant in 100 ml of water is in the range of 0.05 g-6 g, the volume of anhydrous ethanol is one fourth of the volume of water. The carrier 200 is then immersed in the first immersing solution, and is taken out from the first immersing solution, and dried the carrier at 100 degrees Celsius to obtain a first test paper.

In the step of immersing the carrier 200 in the second immersing solution, the color developer, which comprises one or more of DPD, tetramethylbenzidine, syringaldazine, and vanillin azine, is dissolved in anhydrous ethanol and heated to form a second immersing solution, the amount of the color developer added to every 100 ml of anhydrous ethanol is in the range of 0.01 g-10 g. And then the first test paper is immersed in the second immersing solution, and finally is taken ou from the second immersing solution and dried at 80 degrees Celsius to obtain the chlorine detection test paper.

In the manufacturing process of the chlorine detection test paper, an integral piece of the carriers 200 is immersed into the above two immersing solution and dried, and then is cut into small pieces and a piece of the carrier 200 can be attached to the base layer 100 to form the final product of the chlorine detection test paper.

As a first example, 4.05 g polyethylene glycol 4000, 1.98 g citric acid, 2.67 g sodium citrate are dissolved in 800 ml water and mixed, and then 200 ml anhydrous ethanol is added and mixed to obtain the first immersing solution. The second immersing solution is prepared by dissolving 3.25 g DPD in 1000 ml anhydrous ethanol.

As a second example, 6.86 g isooctyl alcohol polyoxy-ethylene ether, 1.22 g boric acid, and 7.89 g borax are dissolved in 800 ml water and mixed, and then 200 ml anhydrous ethanol is added and mixed to obtain the first immersing solution. The second immersing solution is prepared by dissolving 2.43 g tetramethylbenzidine in 1000 ml anhydrous ethanol.

As a third example, 0.523 g Tween 20, 1.57 g disodium hydrogen phosphate, and 2.26 g sodium dihydrogen phosphate are dissolved in 800 ml water and mixed, and then 200 ml anhydrous ethanol is added and mixed to obtain the first immersing solution. The second immersing solution is prepared by dissolving 0.385 g syringaldazine in 1000 ml anhydrous ethanol.

As a fourth example, 3.15 g N,N-dimethyl n-octadecylamine, 1.25 g TRIS are dissolved in 800 ml water and mixed, and then 200 ml anhydrous ethanol is added and mixed to obtain the first immersing solution. The second immersing solution is prepared by dissolving 6.01 g vanillin azine in 1000 ml anhydrous ethanol.

The above is one or more implementation methods provided in combination with the specific content, and it is not intended that the specific implementation of the present invention is limited to these descriptions. Anything similar to or identical to the method, structure, etc. of the present invention, or a number of technical deductions or substitutions made on the premise of the concept of the present invention, should be regarded as the scope of protection of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 9:
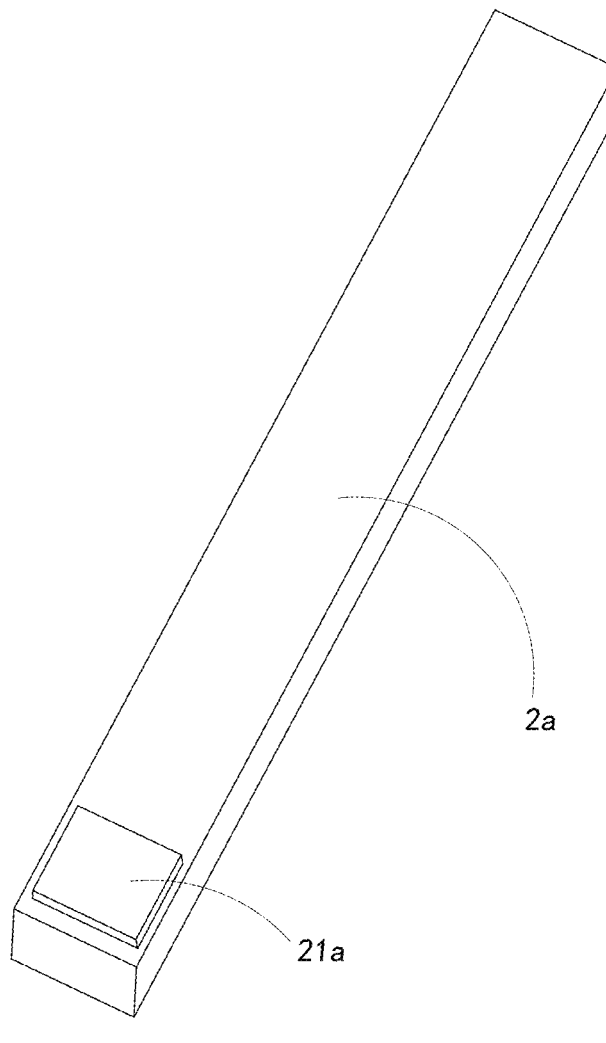
FIG. 9 is a perspective view of the water hardness test paper according to the above first preferred embodiment of the present invention.

With reference to FIGS. 7 to 9, a method for preparing a water hardness test paper comprises the following steps.

Step S20: Provide a color developing substance, the color developing substance comprises one or more of calcium magnesium reagent, chrome black T, calcium carboxylic acid, azo arsine 1, and azo arsine 3.

In this step, the color developing substance is provided, and the color developing substance comprises one or more of calcium magnesium reagent, chrome black T, calcium carboxylic acid, azo arsine 1, and azo arsine 3, and the amount of the color developing substance per 100 ml of water is in the range of 0.05 g-6 g.

Step S21: Provide a buffer;

In this step, the buffer comprises one or more of citric acid, sodium citrate, disodium hydrogen phosphate, sodium dihydrogen phosphate, TBS (Tris Buffered Saline, trishy-droxymethylaminomethane buffered saline), boric acid, borax, and sodium hydroxide. Through the above steps, the buffer can improve the color response of the color developing substance to water hardness and provide a more stable color response, and the buffer can be complexed with the color developing substance to form a brighter and more gorgeous color, and stabilize the color.

Step S22: Dissolve the buffer and the color developing substance in pure water, and mix to form a first solution.

In this step, dissolve the buffer and the color developing substance in pure water, and the amount of the buffer added to each 100 ml of water is in the range of 0.1 g-10 g, and mix to form the first solution; specifically, the buffer and the color developing substance are dissolved in 500 ml of pure water, and the amount of the buffer added to each 100 ml of water is in the range of 0.1 g-10 g, and mix to form the first solution.

Step S23: Add anhydrous ethanol to the first solution and mix to form a second solution; specifically, add 500 ml of anhydrous ethanol to the first solution and mix to form the second solution.

Step S24: Provide a carrier, and immerse the carrier in the second solution.

Step S25: Take out the carrier from the second solution and dry the carrier to obtain a water hardness test paper.

In this step, the carrier is taken out from the second solution, and the carrier is dried at 100 degrees Celsius to obtain a water hardness test paper.

Accordingly, the preparing method comprises the steps of: providing a color developing substance which comprises one or more of calcium magnesium reagent, chrome black T, calcium carboxylic acid, azo arsenic 1, and azo arsenic 3; providing a buffer; dissolving the buffer and the color developing substance in pure water, mixing to form a first solution; adding anhydrous ethanol to the first solution, mixing to form a second solution; providing a carrier, and immersing the carrier in the second solution; taking out the carrier from the second solution, and drying the carrier to obtain a water hardness test paper, so that the user can put the water hardness test paper into the water for detection, and when the color developing substance contacts solutions with different water hardness values, it shows its own structural changes with different colors, and the user is able to know the water hardness value of the current test solution by comparing it with the comparison color card. In addition, the buffer can improve the color response of the color developing substance to water hardness, and provide a more stable color response, and the buffer can be complexed with the color developing substance to form a brighter and more gorgeous color, and stabilize the color.

Referring to FIG. 9, a water hardness test paper is illustrated to comprises a carrier 2a which is provided with a water hardness detection substance for detecting the water hardness value and develop color, and a filtering paper 21a is also provided on the carrier 2a. The area of the filtering paper 21a accounts for 4%-7% of the area of the carrier 2a. Specifically, the width range of the carrier 2a is 3-7 mm, and the length range of the carrier 2a is 60-110 mm. Further, the width range of the filtering paper 21a is 3-7 mm, the length range of the filtering paper 21a is 3-8 mm, and the thickness of the filtering paper 21a is 0.1 mm-0.8 mm. Further, the water hardness detection layer is used to detect the water hardness value and develop color, and the water hardness detection layer is formed by mixing a color developing substance and a buffer. Further, the color developing substance comprises one or more of calcium magnesium reagent, chrome black T, calcium carboxylic acid, azo arsine 1, and azo arsine 3. Furthermore, the buffer comprises one or more of citric acid, sodium citrate, disodium hydrogen phosphate, sodium dihydrogen phosphate, TRIS, boric acid, borax, and sodium hydroxide.

Accordingly, the preparing method of the water hardness paper comprises the steps of: providing a color developing substance which comprises one or more of calcium magnesium reagent, chrome black T, calcium carboxylic acid, azo arsenic 1, and azo arsenic 3; providing a buffer; dissolving the buffer and the color developing substance in pure water, mixing to form a first solution; adding anhydrous ethanol to the first solution, mixing to form a second solution; providing a carrier, and immersing the carrier in the second solution; taking out the carrier from the second solution, and drying the carrier to obtain the water hardness test paper, so that the user can put the water hardness test paper into the water for detection, and when the color developing substance contacts solutions with different water hardness values, it shows its own structural changes with different colors, and the user is able to know the water hardness value of the current test solution comparing it with the comparison color card. In addition, the buffer can improve the color response of the color developing substance to water hardness, and provide a more stable color response, and the buffer can be complexed with the color developing substance to form a brighter and more gorgeous color, and stabilize the color. Moreover, the dimensions of the carrier and the filtering paper are reasonably designed, which is convenient for the production and packaging of water hardness test paper, and the color development effect is better.

Figure 10:
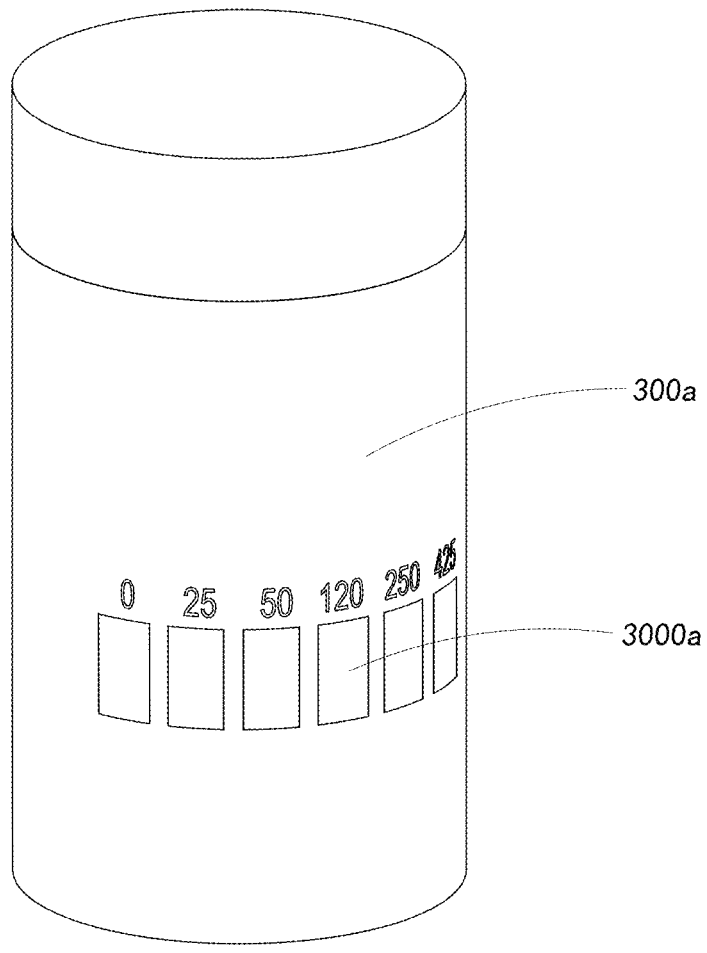
FIG. 10 is a perspective view illustrating a container storing the water hardness test paper of a second preferred embodiment of the present invention.
Figure 11:
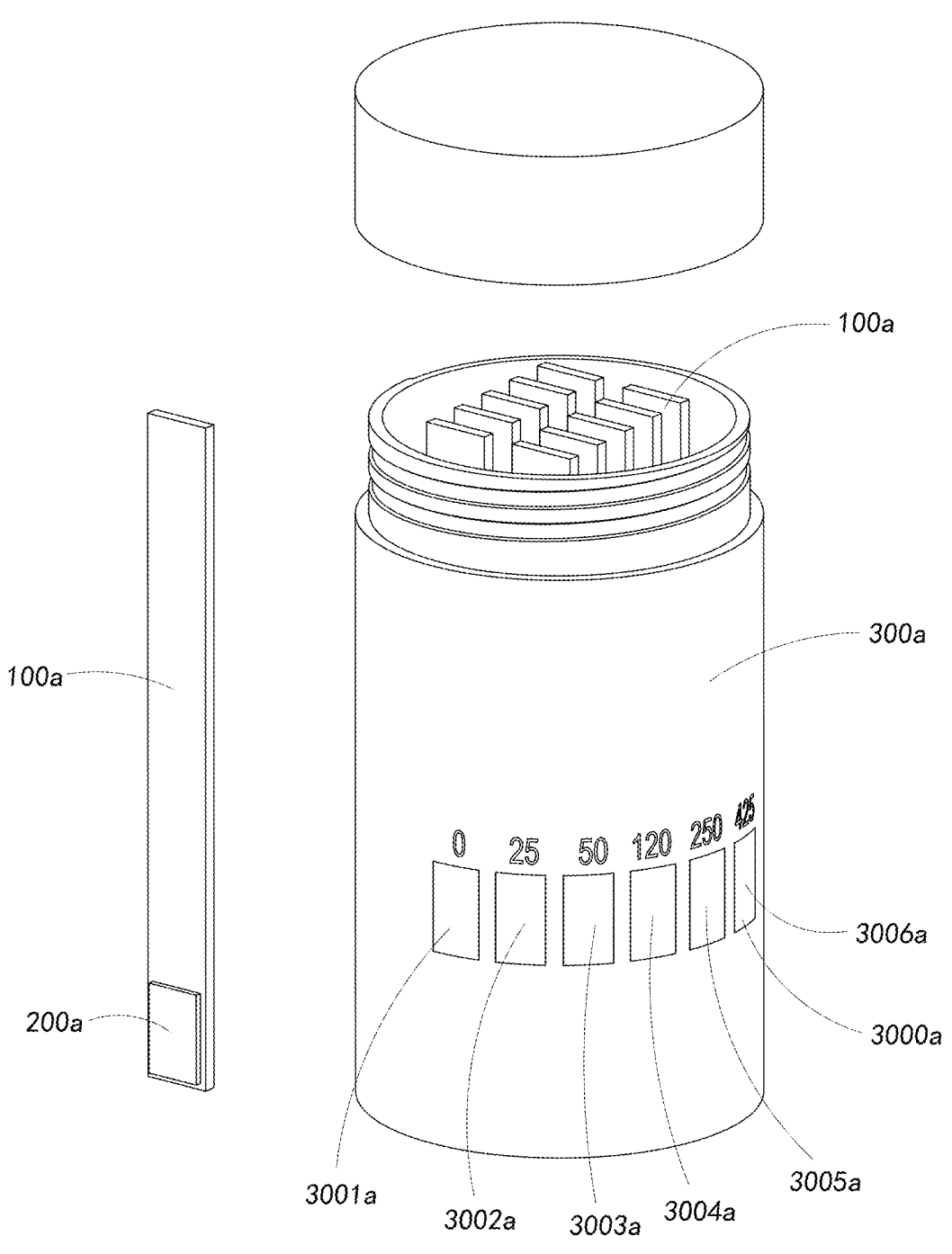
FIG. 11 is an exploded view illustrating the container storing with the water hardness test paper of the above second preferred embodiment of the present invention.

Referring to FIGS. 10 to 11 of the drawings, a water hardness test paper according to a second preferred embodiment of the present invention is illustrated. The water hardness test paper comprises a base layer 100a, and a carrier 200a attached to the base layer 100a for carrying a water hardness detection substance.

Water hardness generally refers to the concentration of calcium and magnesium ions present in the water, and it is a crucial indicator of water quality. The hardness level of water can significantly affect both industrial processes and personal health, making it important to monitor.

The water hardness test paper of the present invention can be applied into various occasions. It can ensures that the hardness of drinking water remains within safe and acceptable levels to avoid potential health issues such as gastrointestinal discomfort or kidney problems. Homeowners and consumers can use the water hardness test paper to monitor their drinking water and maintain health. Detecting hard water is important for protecting home appliances such as water heaters, washing machines, and dishwashers from limescale buildup, which can reduce their efficiency and lifespan. In addition, hard water affects the performance of soaps and detergents, leading to reduced cleaning efficiency in laundry and dishwashing. Regular testing helps adjust water softeners.

Monitoring water hardness is critical to prevent scale formation in industrial boilers and heating systems, which can lead to energy inefficiency, damage, and accidents. Soft water is essential in the textile industry for processes like washing, dyeing, and finishing to prevent fabric stiffness and ensure even color distribution. Consistent water hardness levels are necessary for maintaining product quality in brewing, dairy production, and food processing. Water hardness can also impact soil quality and plant health, especially in regions with hard water, making it important for farmers to monitor the water used in irrigation. High-hardness water can affect animal health, particularly in dairy and poultry farming, leading to decreased productivity and increased health risks. Hardness affects the pH balance and mineral content of water in aquariums and fish farms, influencing the health and growth of fish and aquatic plants In pharmaceutical manufacturing, water with controlled hardness is necessary to ensure the purity and effectiveness of medications. Water used in dialysis must have low hardness to prevent harm to patients, making constant monitoring essential.

The base layer 100a is made of a polymer material such as PET (Polyethylene Terephthalate), PEN (Polyethylene Naphthalate), PP (Polypropylene), and PE (Polyethylene). In this embodiment, the base layer 100 is made of PET.

PET is known for its excellent mechanical strength, providing a robust and durable base layer that can withstand handling and environmental stress during use and storage. PET exhibits strong resistance to chemicals, including acids and bases. This characteristic ensures that the base layer 100a does not degrade or react when exposed to various substances, preserving the integrity of the hardness detection test paper.

PET has low shrinkage and maintains its dimensions under different environmental conditions, such as changes in temperature and humidity. This stability is crucial for the consistent performance of the test paper. PET also offers excellent barrier properties against moisture and gases, protecting the water hardness detection substance from premature degradation due to exposure to air or moisture. This extends the shelf life and reliability of the test paper.

PET can be widely used in manufacturing due to its ease of processing. It can be easily extruded, laminated, or coated, making it a versatile material for creating a consistent and high-quality base layer 100a.

The carrier 200a is used for being immersed in the second solution to carry the water hardness detection substance. In this embodiment, the carrier 200a is made of a filtering paper. Accordingly, the filtering paper is designed to absorb liquids efficiently, ensuring that the immersing second solution, which contains the water hardness detection substance, is evenly distributed across the carrier 200a. This uniform absorption is crucial for consistent test results.

The filtering paper has a porous structure, which allows it to hold and distribute the water hardness detection substance effectively. The porosity ensures that the test paper has sufficient surface area for the calcium and magnesium ions in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the water hardness detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The water hardness detection substance on the carrier 200a comprises one or more of calcium magnesium reagent, chrome black T, calcium carboxylic acid, azo arsine 1, and azo arsine 3.

The calcium magnesium reagent is specifically formulated to detect the presence of both calcium and magnesium ions in water. These ions form complexes with the reagent, resulting in a color change that indicates hardness levels. It can simultaneously detect both calcium and magnesium ions, the primary causes of water hardness. It is beneficial in that it provides a clear color change, making it easy to visually assess water hardness without the need for complex equipment.

Chrome Black T is a complexometric indicator used to detect metal ions like calcium and magnesium. When used in water hardness detection, it changes color in the presence of these ions. It is very sensitive to calcium and magnesium ions, allowing for accurate detection even in low concentrations.

Calcium carboxylic acid reacts with calcium ions to form insoluble calcium salts, which can be detected through precipitation or color changes.

Azo arsine 1 is a reagent that reacts with metal ions, including calcium and magnesium, resulting in a color change that indicates the hardness level of the water. It can detect a broad range of metal ions, making it useful in testing various types of water with different hardness compositions. It also provides a strong and visible color change, making it easy to interpret results without specialized instrument.

Azo arsine 3, like Azo arsine 1, is used for detecting metal ions in water by producing a color change upon reaction with calcium and magnesium ions.

The buffer comprises one or more of citric acid, disodium EDTA, sodium citrate, disodium EDTA, disodium hydrogen phosphate, sodium dihydrogen phosphate, TRIS, boric acid, borax, and sodium hydroxide. The buffer in the water hardness detection system is critical for maintaining the pH at an optimal level for the reactions between the hardness detection reagents and the calcium and magnesium ions.

Accordingly, the buffer helps maintain a stable pH environment that is crucial for the optimal performance of the color developing substances. Color developing reactions, such as those involving calcium and magnesium reagents, are often highly pH-sensitive.

By stabilizing the pH at the optimal level for the specific reagents, the buffer ensures that the color developing substance reacts more sensitively to changes in water hardness. This leads to a quicker and more noticeable color change, improving the detection process.

Without a stable buffer, fluctuations in pH could lead to inconsistent color responses, making it difficult to accurately assess the hardness. The buffer minimizes this issue, leading to more reliable and reproducible results.

The buffer also ensures that the color developing reaction proceeds smoothly, maintaining consistent reaction conditions throughout the test. This results in a more stable and lasting color response.

Accordingly, a well-buffered system prevents the color from fading prematurely, allowing the test paper to display the results over a longer period. This stability is important for the user to interpret the results accurately, especially when immediate comparison to a color chart is required.

In addition, external factors like temperature and small impurities in the water can affect the pH. The buffer system helps mitigate these influences, ensuring the color response remains stable and reliable across different environments.

Furthermore, the buffer can also influence the intensity and brightness of the color produced by the reaction. It interacts with the color developing substances to create a clearer, more distinguishable color change. A brighter and more vibrant color makes the result easier to interpret by the naked eye. This is especially useful for test strips designed for consumer use, where precise interpretation of color change is key to assessing water hardness.

The buffer may complex with the color developing substance, producing colors that are not only brighter but also more visually appealing. This is particularly advantageous in tests where different levels of water hardness are represented by different color intensities, as it allows for better differentiation between hardness levels.

It is worth mentioning that the buffer also helps stabilize the color produced by the reaction, preventing color shifts or degradation over time. This ensures the color remains true to the actual hardness level for the duration of the test. Stabilizing the color ensures that the user can accurately interpret the test result without worrying about the color changing after the initial reaction. This is critical for consistency, especially when the test strip needs to be read after a set period. Stabilizing the color response also ensures that the test strips maintain their efficacy for longer periods, making them more reliable and extending their shelf life.

Citric acid is a weak organic acid commonly used in buffering systems to control the pH. It can be employed in the present invention to stabilize the pH in the slightly acidic range, which is necessary for hardness detection reagents to function properly. Citric acid can also chelate metal ions, helping to control their concentration in water samples and allowing for more accurate detection of calcium and magnesium.

Sodium citrate is the sodium salt of citric acid and is commonly used as a buffering agent to maintain a stable pH. It can work well with citric acid to create a buffer system that can maintain a consistent pH level. Sodium citrate does not interfere with the calcium and magnesium ions, allowing accurate hardness detection in the present invention.

Disodium EDTA can effectively bind with calcium and magnesium ions, which are the main contributors to water hardness. This chelation forms stable complexes with these ions, facilitating their detection in water samples. The ability of disodium EDTA to complex with these ions improves the precision and accuracy of the hardness measurement, ensuring a clear response from the color-developing substances used in the detection system.

Disodium hydrogen phosphate is a phosphate buffer that helps control pH in the slightly alkaline range. It can keep the pH stable in a slightly basic range, which is suitable for certain reagents like Chrome Black T to perform effectively. It also does not react with calcium or magnesium, preserving the integrity of hardness detection.

Sodium dihydrogen phosphate is another phosphate salt used for buffering in combination with disodium hydrogen phosphate. When used with disodium hydrogen phosphate, it creates a buffer system that can control pH in both acidic and slightly alkaline environments. It can allow for precise pH control across a broad pH range, accommodating different types of hardness detection reagents.

TRIS is a versatile buffering agent widely used in biochemical applications, especially for maintaining a stable pH in a slightly alkaline environment. It can be effective at maintaining pH around neutral or slightly alkaline, which is ideal for many water hardness detection reactions. It does not interfere with calcium or magnesium detection, ensuring accurate results.

Boric acid is a weak acid commonly used in buffering solutions to maintain a stable pH in mildly acidic conditions. It provides a gentle pH adjustment, which can be beneficial when detection reagents are sensitive to large pH fluctuations. Its use in water testing is well-established, making it reliable and effective.

Borax, or sodium tetraborate, is often used with boric acid to create a borate buffer system, providing pH stability in mildly alkaline conditions. Borax, when combined with boric acid, helps maintain a stable pH in the alkaline range, which is ideal for some of the water hardness detection reagents. It stabilizes the pH without interacting with hardness ions, preserving the integrity of the water hardness test.

Sodium hydroxide is a strong base used to adjust the pH to alkaline levels when necessary. It can quickly and effectively raise pH levels, allowing for rapid adjustment in cases where the water sample is too acidic.

The present invention further provides a container 300 for storing a plurality of the water hardness test paper, and a plurality of color blocks 3000 are painted on an outer surface of the container 300 for indicating the levels of water hardness.

In this embodiment, the plurality of color blocks 3000a comprises a first color block 3001a, a second color block 3002a, a third color block 3003a, a fourth color block 3004a, a fifth color block 3005a, and a sixth color block 3006a. The detection result corresponding to the first color block 3001a is 0 mg/L, the detection result corresponding to the second color block 3002a is 25 mg/L, the detection result corresponding to the third color block 3003a is 50 mg/L, the detection result corresponding to the fourth color block 3004a is 120 mg/L, and the detection result corresponding to the fifth color block 3005a is 250 mg/L, the detection result corresponding to the sixth color block 3006a is 425 mg/L.

The inclusion of color blocks 3000a directly on the container 300 provides an easy and immediate reference for users to compare the color change of the test paper with the standard color blocks. This feature simplifies the process of interpreting test results, as users can directly compare the test paper to the color blocks on the container without needing a separate reference card.

The color blocks 3000a being painted on the container 300a ensure that the reference guide is always available with the test papers. This design reduces the risk of misplacing or losing the color reference, making the test kit more user-friendly and accessible, especially in field conditions.

By incorporating a range of color blocks 3000a that correspond to specific water hardness concentration levels, the design offers clear visual differentiation between different concentrations. This clarity helps users more accurately determine water hardness levels, even in situations where precise readings are critical.

Since the color blocks 3000a are painted on the container 300a, they are less likely to be damaged or worn compared to a separate paper reference card. This increases the durability of the test kit, ensuring that the reference guide remains intact and legible over time. The color blocks 300a may be painted on an outer surface of the container 300a, or the color blocks 300a are painted on a paper sheet and the paper sheet is then attached on the container body of the container 300a.

Combining the test paper storage and the color reference in one container makes the entire testing kit more compact and portable. Users can carry the container with them easily, knowing that they have everything needed for water hardness testing in one convenient package.

The present invention further provides a method for preparing the water hardness test paper, and the method comprises the steps of providing an immersing solution and immersing the carrier 200a in the immersing solution.

In the step of providing the immersing solution, the buffer and the color developing substance are dissolved and mixed in pure water, and then anhydrous ethanol is added to obtain the immersing solution. In this step, the buffer and the color developing substance are dissolved in 500 ml of pure water, and the amount of the buffer added to each 100 ml of water is in the range of 0.1 g-10 g, the amount of the color developing substance added to each 100 ml of water is in the range of 0.05 g-6 g. Accordingly, 0.5 g-50 g buffer and 0.25 g-30 g color developing substance are added in the 500 ml of water. And then, 500 ml of anhydrous ethanol is added to the mixture to obtain the immersing solution.

In the step of immersing the carrier 200a in the immersing solution, the carrier is immersed in the above immersing solution and then is taken out from the immersing solution and dried to obtain the water hardness test paper.

In the manufacturing process of the water hardness test paper, an integral piece of the carriers 200a is immersed into the above immersing solution and dried, and then is cut into small pieces and a piece of the carrier 200a can be attached to the base layer 100 to form the final product of the water hardness test paper.

As a first example, 0.35 g calcium magnesium reagent, 0.7 g citric acid, 0.423 g disodium EDTA and 2.8 g sodium hydroxide are added and mixed in 500 ml water, and then 500 ml of anhydrous ethanol is added to the mixture to obtain the immersing solution. Under alkaline conditions, the calcium magnesium reagent undergoes a complexation reaction with calcium and magnesium ions to display a pink color.

As a second example, 0.462 g Chrome Black T, 1.01 g disodium hydrogen phosphate, and 1.41 g sodium dihydrogen phosphate are dissolved and mixed in 500 ml water, and then 500 ml of anhydrous ethanol is added to the mixture to obtain the immersing solution. When Chrome Black T binds to calcium or magnesium ions in hard water, it changes to a red or wine color, signaling the presence of hardness causing ions. In the absence of calcium and magnesium ions, Chrome Black T typically displays a blue or purple color.

As a third example, 0.862 g calcium carboxylic acid, 1.42 g citric acid and 0.526 g sodium citrate are added and mixed in 500 ml water, and then 500 ml of anhydrous ethanol is added to the mixture to obtain the immersing solution. When used in the detection of water hardness, calcium carboxylic acids typically form insoluble precipitates when they encounter high concentrations of calcium or magnesium ions. This leads to visual changes, as calcium carboxylic acids may result in cloudiness, precipitate formation, or other physical changes that can indicate water hardness.

As a fourth example, 0.348 g azo arsenic acid 1, 0.76 g boric acid, and 4.93 g borax are added and mixed in 500 ml water, and then 500 ml of anhydrous ethanol is added to the mixture to obtain the immersing solution. When Azo Arsenic Acid 1 is used in water hardness detection, it typically forms a complex with calcium or magnesium ions, which results in a color change. The color displayed by this reagent can vary depending on the concentration of calcium or magnesium ions present in the water. In low concentration of Calcium/Magnesium Ions, a light pink can be displayed while in a high concentration of Calcium/Magnesium Ions, upon binding with calcium or magnesium ions, Azo Arsenic Acid 1 typically displays a purple or violet color.

Figure 12:
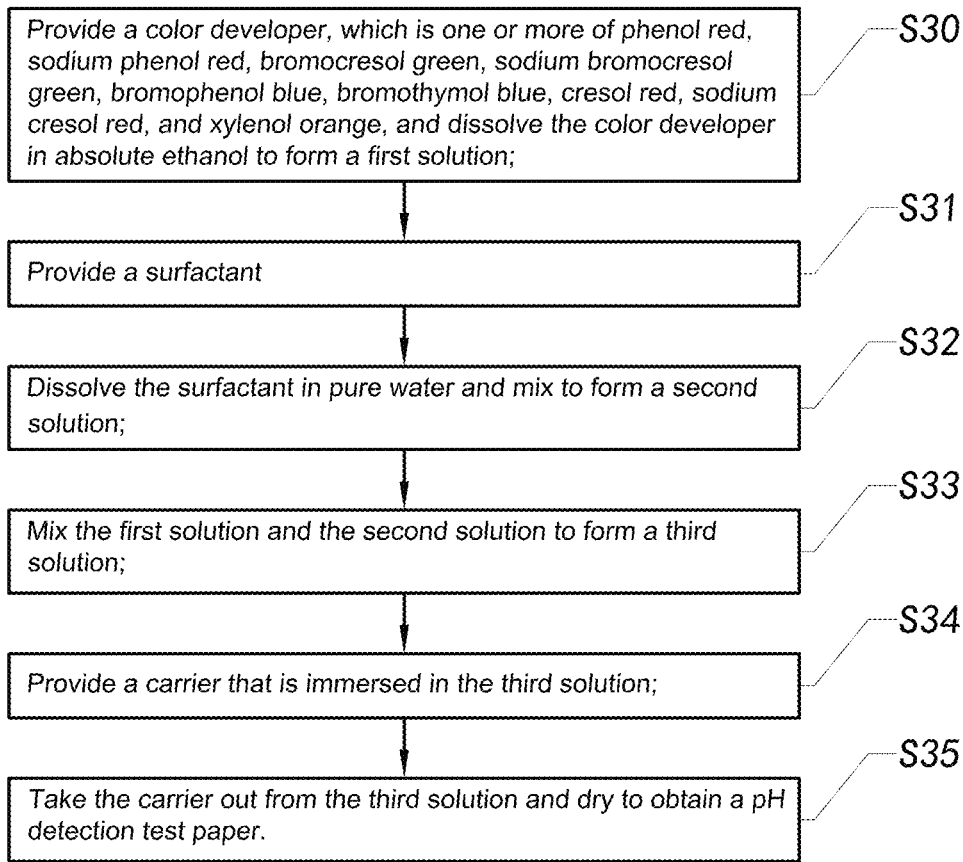
FIG. 12 is a schematic diagram of the overall process of the present invention.

Reference FIG. 12 to FIG. 13, a preparation method of pH detection test paper comprises the following steps.

Step S30: provide a color developer, the color developer is one or more of phenol red, sodium phenol red, bromocresol green, sodium bromocresol green, bromophenol blue, bromothymol blue, cresol red, sodium cresol red, and xylenol orange, and dissolve the color developer in absolute ethanol to form a first solution;

In this step, a color developer is provided, which is one or more of phenol red, phenol red sodium, bromocresol green, bromocresol green sodium, bromophenol blue, bromothymol blue, cresol red, cresol red sodium, and dimethylphenol orange, the color developer is dissolved in absolute ethanol, and the added amount of the color developer per 100 ml of absolute ethanol ranges from 0.03 g to 5 g to form a first solution. Specifically, the color developer is provided, and the color developer is one or more of phenol red, sodium phenol red, bromocresol green, sodium bromocresol green, bromophenol blue, bromothymol blue, cresol red, sodium cresol red, dimethyl phenol orange, the color developer is dissolved in 600 ml of absolute ethanol, and the amount of the color developer added per 100 ml of absolute ethanol ranges from 0.03 g to 5 g to form the first solution.

Step S31: Provide a surfactant;

In this step, the surfactants are one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.

Step S32: Dissolve the surfactant in pure water and mix to form a second solution;

In this step, the surfactant is dissolved in water, the amount of surfactant added per 100 ml of water ranges from 0.05 g to 6 g, and mixed to form a second solution. Specifically, the surfactant is dissolved in 400 ml of water, the amount of surfactant added per 100 ml of water ranges from 0.05 g to 6 g, and mixed to form a second solution. Through the above steps, the surfactant contributes to the wetting of the carrier by the test sample without adversely affecting the color transition of the chromogen in response to pH. In addition, the surfactants can also improve the stability of the color transition of the chromogen.

Step S33: Mix the first solution and the second solution to form a third solution; Step S34: Provide a carrier, and immerse the carrier in the third solution;

Step S35: Take out the carrier from the third solution and dry the carrier to obtain pH detection test paper.

In this step, the carrier is taken out from the third solution, and the carrier is dried at 100 degrees Celsius to obtain a pH detection test paper Through the above steps, the method comprises: providing a color developer, which is one or more of phenol red, sodium phenol red, bromocresol green, sodium bromocresol green, bromophenol blue, bromothymol blue, cresol red, cresol red sodium, and dimethylphenol orange, dissolving phenol red in absolute ethanol to form a first solution; providing a surfactant; dissolving the surfactant in pure water, and mixing to form a second solution; mixing the first solution and the second solution to form a third solution; providing a carrier, and the carrier is immersed in the third solution; taking out the carrier from the third solution, and drying the carrier to obtain a pH detection test paper, so that the user can put the pH detection test paper into Testing is carried out in water. When the color developer comes into contact with solutions of different pH values, it will show its own structural changes and display different colors. The pH value of the current test solution can be known by comparing it with the comparison color card. Furthermore, the surfactant facilitates wetting of the test sample to the carrier without adversely affecting the color transition of the chromogen in response to pH. In addition, surfactants can also improve the stability of the color transition of chromophores.

Figure 14:
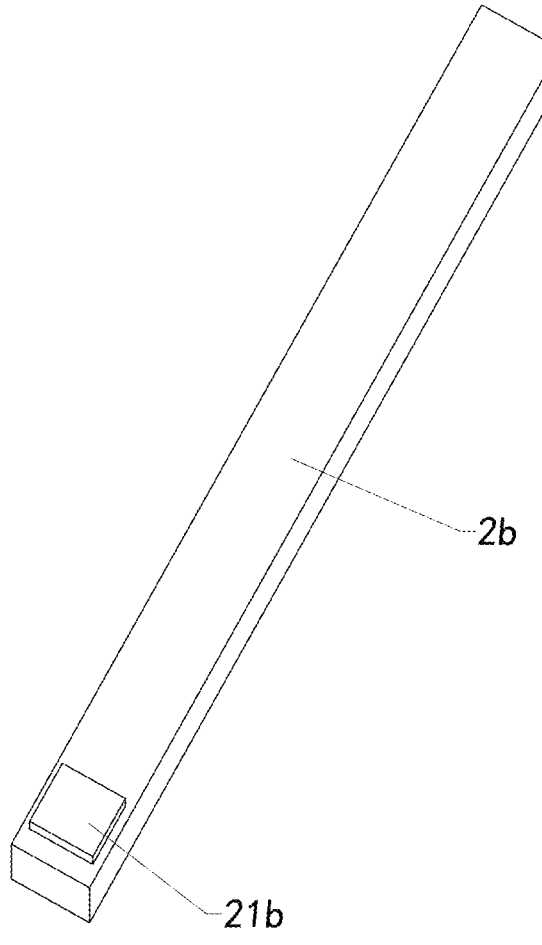
FIG. 14 is a perspective view illustrating the overall structure of a pH detection test paper of a preferred embodiment of the present invention.

Reference FIG. 14, a pH detection test paper is illustrated to comprise a carrier 2b, the carrier 2b is covered with a pH detection layer, the pH detection layer is used to detect the pH value and develop color, and the carrier 2b is also provided with a filtering paper 21b. The area of the filtering paper 21b accounts for 4%-7% of the area of the carrier 2b. Specifically, the width of the carrier 2b ranges from 3 to 7 mm, and the length of the carrier 2b ranges from 60 to 110 mm. Further, the width of the filtering paper 21b ranges from 3 to 7 mm, the length of the filtering paper 21b ranges from 3 to 8 mm, and the thickness of the filtering paper 21b ranges from 0.1 mm to 0.8 mm. Furthermore, the pH detection layer is used to detect the pH value and develop color. The pH detection layer is formed by mixing a pH color developing substance and a surface active substance. Furthermore, the pH chromogens are one or more of phenol red, sodium phenol red, bromocresol green, sodium bromocresol green, bromophenol blue, bromothymol blue, cresol red, cresol red sodium, and dimethylphenol orange. Furthermore, the surfactant is one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctanol polyoxyethylene ether, and N, N-dimethyl n-octadecylamine. Through the above structure, since it includes: providing color developers, the color developers are one or more of phenol red, phenol red sodium, bromocresol green, bromocresol green sodium, bromophenol blue, bromothymol blue, cresol red, cresol red sodium, and dimethylphenol orange, dissolving phenol red in absolute ethanol to form a first solution; providing a surfactant; dissolving the surfactant in pure water, and mixing to form a second solution; mixing the first solution and the second solution to form a third solution; provide a carrier, and the carrier is immersed in the third solution; takin out the carrier from the third solution, and drying the carrier to obtain a pH detection test paper, so that the user can put the pH detection test paper into Testing is carried out in water. When the color developer comes into contact with solutions of different pH values, it will show its own structural changes and display different colors. The pH value of the current test solution can be known by comparing it with the comparison color card. Furthermore, the surfactant facilitates wetting of the test sample to the carrier without adversely affecting the color transition of the chromogen in response to pH. In addition, the surfactants can also improve the stability of the color transition of chromophores. Moreover, the size of the above-mentioned carrier and filtering paper is designed reasonably, which facilitates the production and packaging of pH detection test paper, and has better color development effect.

Figure 15:
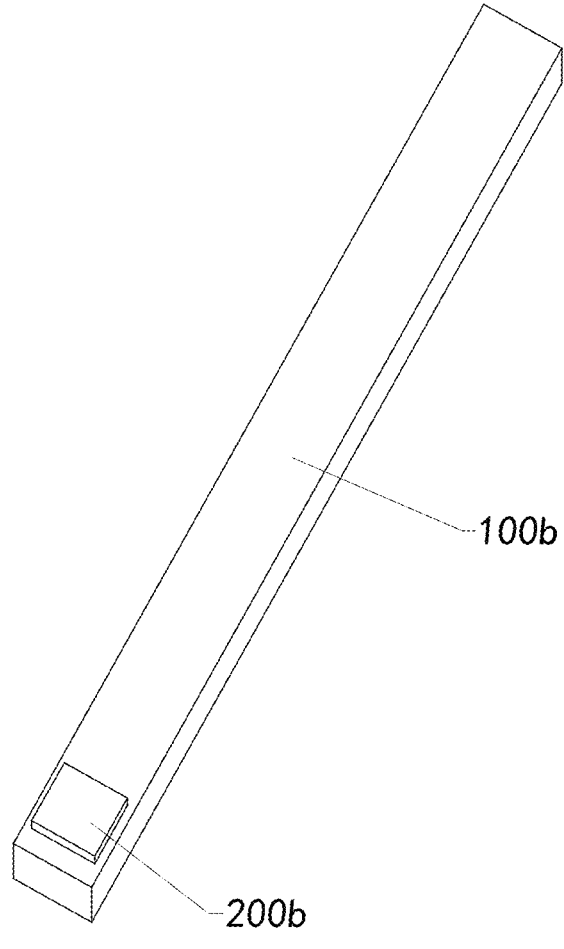
FIG. 15 is a perspective view illustrating the overall structure of a pH detection test paper of a second preferred embodiment of the present invention.

Referring to FIG. 15 of the drawings, a pH detection test paper according to a second preferred embodiment of the present invention is illustrated. The pH detection test paper comprises a base layer 100b, and a carrier 200b attached to the base layer 100b for carrying a pH detection substance.

The pH detection test paper for water quality detection can be used in various applications, including domestic water, swimming pools, aquariums, and disinfection. This type of test paper is commonly employed to measure pH levels, ensuring water safety and cleanliness. Beyond these areas, pH detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100b is made of a polymer material such as PET (Polyethylene Terephthalate), PEN (Polyethylene Naphthalate), PP (Polypropylene), and PE (Polyethylene). In this embodiment, the base layer 100 is made of PET.

The carrier 200b is used for being immersed in the immersing solutions to carry the pH detection substance. In this embodiment, the carrier 200b is made of a filtering paper. Accordingly, the filtering paper is designed to absorb liquids efficiently, ensuring that the immersing solution, which contains the pH detection substance, is evenly distributed across the carrier 200b. This uniform absorption is crucial for consistent test results.

The filtering paper has a porous structure, which allows it to hold and distribute the pH detection substance effectively. The porosity ensures that the test paper has sufficient surface area for the pH in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the pH detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The pH detection substance on the carrier 200b comprises a color developer which comprises one or more of phenol red, phenol red sodium, bromocresol green, bromocresol green sodium, bromophenol blue, bromothymol blue, cresol red, cresol red sodium, and dimethylphenol orange.

Preferably, the pH detection substance is formed by mixing the color developer and the surfactant, the pH color developer comprises one or more of phenol red, phenol red sodium, bromocresol green, bromocresol green sodium, bromophenol blue, bromothymol blue, cresol red, cresol red sodium, and dimethylphenol orange; the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.

The use of one or more color developers like phenol red, phenol red sodium, and bromocresol green ensures a sensitive and precise colorimetric response to pH. These developers produce distinct and easily observable color changes upon reacting with pH, allowing for accurate detection across a range of pH concentrations.

The addition of surfactants like Tween 20, Tween 80, Span 80, BRIJ47, polyvinyl pyrrolidone (K30, K90), polyethylene glycol 4000, polyvinyl alcohol, fatty alcohol polyoxyethylene ether, isooctyl alcohol polyoxyethylene ether, and N,N-dimethyl n-octadecylamine aids in improving the wetting properties of the detection substance. These surfactant ensures that the pH detection substance is evenly distributed on the carrier 200, leading to consistent and uniform test results. The surfactant also helps in preventing the aggregation of the color developers, further enhancing the accuracy of the detection.

The use of carefully selected buffer and surfactant contributes to the overall stability of the pH detection substance. By preventing the degradation of the color developers and ensuring a stable pH environment, the formulation is protected against environmental factors such as temperature fluctuations and humidity. This leads to an extended shelf life, making the detection substance more reliable over time.

The present invention further provides a method for preparing the pH detection test paper, and the method comprises the steps of immersing the carrier 200b in a first immersing solution and immersing the carrier 200b in a second immersing solution.

As a first example, 0.18 g phenol red is dissolved in 600 ml anhydrous ethanol to obtain the first solution, and 0.05 g Tween 20 is dissolved in 400 ml water to obtain the second solution. The first solution and the second solution are mixed to the third solution.

As a second example, 15 g bromophenol blue is dissolved in 600 ml anhydrous ethanol to obtain the first solution, and 24 g Span 80 is dissolved in 400 ml water to obtain the second solution. The first solution and the second solution are mixed to the third solution.

As a third example, 1 g bromothymol blue is dissolved in 600 ml anhydrous ethanol to obtain the first solution, and 2 g Tween 80 is dissolved in 400 ml water to obtain the second solution. The first solution and the second solution are mixed to the third solution.

The above is one or more implementation methods provided in combination with the specific content, and it is not intended that the specific implementation of the present invention is limited to these descriptions. Anything similar to or identical to the method, structure, etc. of the present invention, or a number of technical deductions or substitutions made on the premise of the concept of the present invention, should be regarded as the scope of protection of the present invention.

The above is one or more embodiments provided in conjunction with specific content, and it does not mean that the specific implementation of the present invention is limited to these descriptions. Anything that is similar or identical to the methods, structures, etc. of the present invention, or some technical deductions or substitutions based on the concept of the present invention, shall be regarded as within the protection scope of the present invention.

Figure 17:
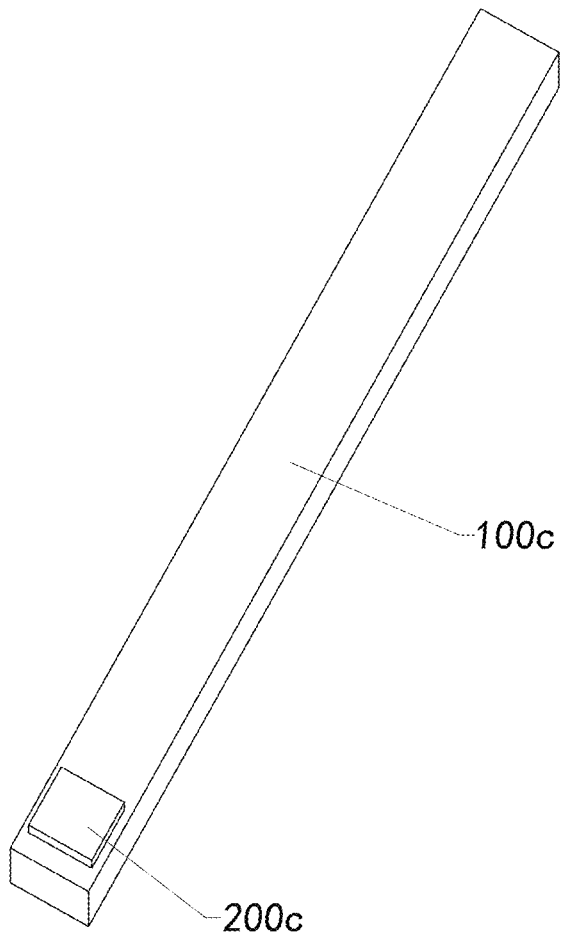
FIG. 17 is a perspective view illustrating the overall structure of a cyanuric acid detection test paper of a preferred embodiment of the present invention.

Referring FIG. 16 to FIG. 17, a preparation method of cyanuric acid detection test paper comprises the following steps.

Step S40: Provide a color rendering agent, the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

In this step, the color rendering agent is provided, and the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

Step S41: Provide a surfactant;

In this step, the surfactant can comprise one or more of cationic, anionic, and nonionic surfactant. Specially, the surfactant can include but not limit to one or more of Tween 20, Tween 80, Span 80, BRIJ47 (polyoxyethylene), polyvinylpyrrolidone K30, polyvinylpyrrolidone K90, polyethylene glycol 4000, polyvinyl alcohol, aliphatic alcohol polyoxyethylene ether, isooctanol polyoxyethylene ether and N,N-dimethyldioctadecylamine.

Step S42: Dissolve the color rendering agent and the surfactant in ethanol and mix to form a first solution;

In this step, the color rendering agent and the surfactant are dissolved in ethanol. The amount of surfactant added per 100 ml of ethanol ranges from 0.002 g to 0.8 g. The amount of color rendering agent added per 100 ml of ethanol ranges from 0.008 g to 2 g. Mix to form the first solution.

In this step, the color rendering agent can be dissolved in ethanol independently without the surfactant.

Step S43: Dissolve melamine $C_3H_6N_6$ in water to form a second solution;

In this step, the melamine is dissolved in water, such as pure water. The amount of melamine added per 100 ml of water ranges from 0.05 g-1 g.

In this step, the surfactant can be dissolved with the melamine in water to form the second solution.

The surfactant can be selected to be dissolved in the first solution or in the second solution based on its solubility.

Step S44: Provide a carrier 200c to immerse in the first solution and take out the carrier 200c from the first solution to dry.

Step S45: Immerse the carrier 200c in the second solution and take out the carrier from the second solution to dry to obtain a third test paper.

Step S46: Attach the carrier 200c to the base layer 100c to form the final product of the cyanuric acid detection test paper.

Reference to FIG. 17, a cyanuric acid detection test paper according to a preferred embodiment of the present invention is illustrated. The cyanuric acid detection test paper comprises the base layer 100c, and the carrier 200c attached to the base layer 100c for carrying a cyanuric acid detection substance.

The cyanuric acid detection test paper for water quality detection can be used in various applications, including domestic water, swimming pools, aquariums, and disinfection. This type of test paper is commonly employed to measure cyanuric acid levels, ensuring water safety and cleanliness. Beyond these areas, cyanuric acid detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100c is made of a polymer material such as PET (Polyethylene Terephthalate), PEN (Polyethylene Naphthalate), PP (Polypropylene), and PE (Polyethylene). In this embodiment, the base layer 100 is made of PET.

The carrier 200c is used for being immersed in the immersing solutions to carry the cyanuric acid detection substance. In this embodiment, the carrier 200c is made of a filtering paper. Accordingly, the filtering paper is designed to absorb liquids efficiently, ensuring that the immersing solution, which contains the cyanuric acid detection substance, is evenly distributed across the carrier 200c. This uniform absorption is crucial for consistent test results.

The filtering paper has a porous structure, which allows it to hold and distribute the cyanuric acid detection substance effectively. The porosity ensures that the test paper has sufficient surface area for the cyanuric acid in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the cyanuric acid detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The cyanuric acid detection substance on the carrier 200*c* comprises a color rendering agent wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

Preferably, the cyanuric acid detection substance is formed by mixing the color rendering agent, the surfactant and the melamine, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether and N,N-dimethyldioctadecylamine.

The use of one or more color developers ensure a sensitive and precise colorimetric response to cyanuric acid. These developers produce distinct and easily observable color changes upon reacting with cyanuric acid, allowing for accurate detection across a range of cyanuric acid concentrations.

The addition of the surfactant like Tween 20, Tween 80, Span 80, BRIJ47, polyvinyl pyrrolidone (K30, K90), polyethylene glycol 4000, polyvinyl alcohol, fatty n-octadecylamine aids in improving the wetting properties of the detection substance. These surfactant ensures that the cyanuric acid detection substance is evenly distributed on the carrier 200*c*, leading to consistent and uniform test results. The surfactant also helps in preventing the aggregation of the color developers, further enhancing the accuracy of the detection.

As a first example, 0.5 g phenol red is dissolved in 500 ml ethanol to form the first solution. 0.8 g melamine and 0.08 g polyethylene glycol 4000 are dissolved in 500 ml water to form the second solution. The carrier 200 is immersed into the first solution and then immersed into the second solution after drying. Take out the carrier 200 from the second solution to dry the carrier 200 and attach the dried carrier 200 to the base layer 100 to form the final product of the cyanuric acid detection test paper.

As a second example, 0.8 g bromocresol purple and 2.0 g isooctanol polyoxyethylene ether are dissolved in 500 ml ethanol to form the first solution. 1.0 g melamine is dissolved in 500 ml water to form the second solution. The carrier 200 is immersed into the first solution and then immersed into the second solution after drying. Take out the carrier 200 from the second solution to dry the carrier 200 and attach the dried carrier 200 to the base layer 100 to form the final product of the cyanuric acid detection test paper.

As a third example, 0.002 g sodium cresol red and 0.008 g N,N-dimethyloctadecylamine are dissolved in 500 ml ethanol to form the first solution. 0.05 g melamine is dissolved in 500 ml water to form the second solution. The carrier 3 is immersed into the first solution and then immersed into the second solution after drying. Take out the carrier 3 from the second solution to dry the carrier 3 and attach the dried carrier 3 to the base layer 100 to form the final product of the cyanuric acid detection test paper.

Figure 18:
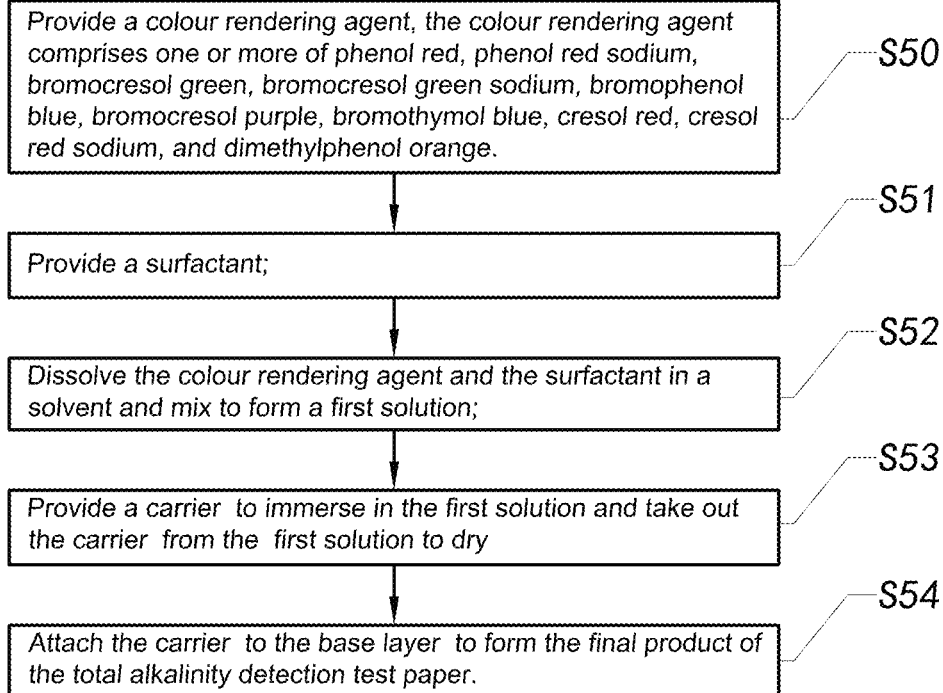
FIG. 18 is a schematic diagram of the overall process of the present invention.

Reference FIG. 18, a preparation method of total alkalinity detection test paper comprises the following steps.

Step S50: Provide a color rendering agent, the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

In this step, the color rendering agent is provided, and the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

Step S51: Provide a surfactant;

In this step, the surfactants can include cationic, anionic, and nonionic surfactants. Specially, the surfactants can include but not limit to one or more of Tween 20, Tween 80, Span 80, BRIJ47 (polyoxyethylene), polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

Step S52: dissolve the color rendering agent and the surfactant in a solvent and mix to form a first solution;

In this step, the solvent can be water, alcohol or other soluble substances. For example, the color rendering agent and the surfactant are dissolved in water. The amount of surfactant added per 100 ml of solvent ranges from 0.1 g to 3.0 g. The amount of color rendering agent added per 100 ml of solvent ranges from 0.002 g to 0.9 g. Mix to form the first solution.

Step S53: Provide a carrier 200*d* to immerse in the first solution and take out the carrier 4 from the first solution to dry to obtain a total alkalinity detection test paper.

Step S54: Attach the carrier 200*d* to the base layer 100 to form the final product of the total alkalinity detection test paper.

Figure 19:
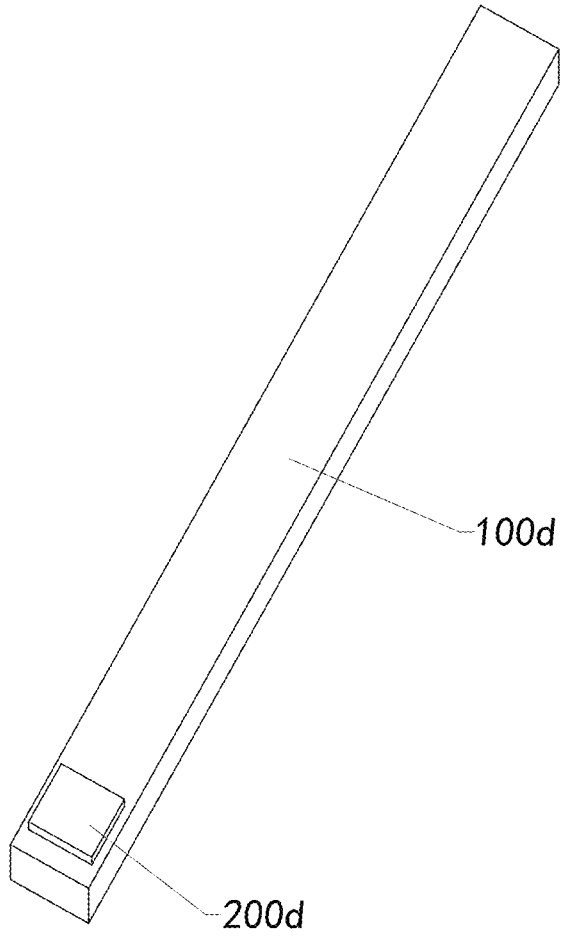
FIG. 19 is a perspective view illustrating the overall structure of a total alkalinity detection test paper of a preferred embodiment of the present invention.

Reference to FIG. 19, a total alkalinity detection test paper according to a preferred embodiment of the present invention is illustrated. The total alkalinity detection test paper comprises the base layer 100*d*, and the carrier 200*d* attached to the base layer 100*d* for carrying a total alkalinity detection substance.

The total alkalinity detection test paper for water quality detection can be used in various applications, including domestic water, swimming pools, aquariums, and disinfection. This type of test paper is commonly employed to measure total alkalinity levels, ensuring water safety and cleanliness. Beyond these areas, total alkalinity detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100*d* is made of a polymer material such as PET (Polyethylene Terephthalate), PEN (Polyethylene Naphthalate), PP (Polypropylene), and PE (Polyethylene). In this embodiment, the base layer 100*d* is made of PET.

The carrier 200*d* is used for being immersed in the immersing solutions to carry the total alkalinity detection substance. In this embodiment, the carrier 200*d* is made of a filtering paper. Accordingly, the filtering paper is designed to absorb liquids efficiently, ensuring that the immersing solution, which contains the total alkalinity detection substance, is evenly distributed across the carrier 200*d*. This uniform absorption is crucial for consistent test results.

The filtering paper has a porous structure, which allows it to hold and distribute the total alkalinity detection substance effectively. The porosity ensures that the test paper has sufficient surface area for the total alkalinity in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the total alkalinity detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The total alkalinity detection substance on the carrier 200d comprises a color rendering agent wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

Preferably, the total alkalinity detection substance is formed by mixing the color rendering agent, the surfactant and the melamine, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol ether, polyoxyethylene and N,N-dimethyldioctadecylamine.

The use of one or more color developers ensure a sensitive and precise colorimetric response to total alkalinity. These developers produce distinct and easily observable color changes upon reacting with total alkalinity, allowing for accurate detection across a range of total alkalinity concentrations.

The addition of the surfactant like Tween 20, Tween 80, Span 80, BRIJ47, polyvinyl pyrrolidone (K30, K90), polyethylene glycol 4000, polyvinyl alcohol, fatty n-octadecylamine aids in improving the wetting properties of the detection substance. These surfactant ensures that the total alkalinity detection substance is evenly distributed on the carrier 200d, leading to consistent and uniform test results. The surfactant also helps in preventing the aggregation of the color developers, further enhancing the accuracy of the detection.

As a first example, 0.6 g bromophenol blue, 0.25 g bromothymol blue, 0.008 g bromocresol violet and 1.0 g polyvinyl alcohol is are dissolved in 1000 ml water to form the first solution. The carrier 200d is immersed into the first solution and then take out the carrier 200d from the first solution to dry.

Attach the dried carrier 200d to the base layer 100d to form the final product of the total alkalinity detection test paper.

As a second example, 0.2 g bromophenol blue and 5 g N,N-dimethyloctadecylamine are dissolved in 1000 ml water to form the first solution. The carrier 200d is immersed into the first solution and then take out the carrier 200d from the first solution to dry. Attach the dried carrier 200d to the base layer 100d to form the final product of the total alkalinity detection test paper.

As a third example, 5.0 g cresol orange, 4.0 g bromothymol blue and 1.0 g polyvinyl alcohol is are dissolved in 1000 ml water to form the first solution. The carrier 200d is immersed into the first solution and then take out the carrier 200d from the first solution to dry.

Attach the dried carrier 200d to the base layer 100d to form the final product of the total alkalinity detection test paper.

Figure 20:
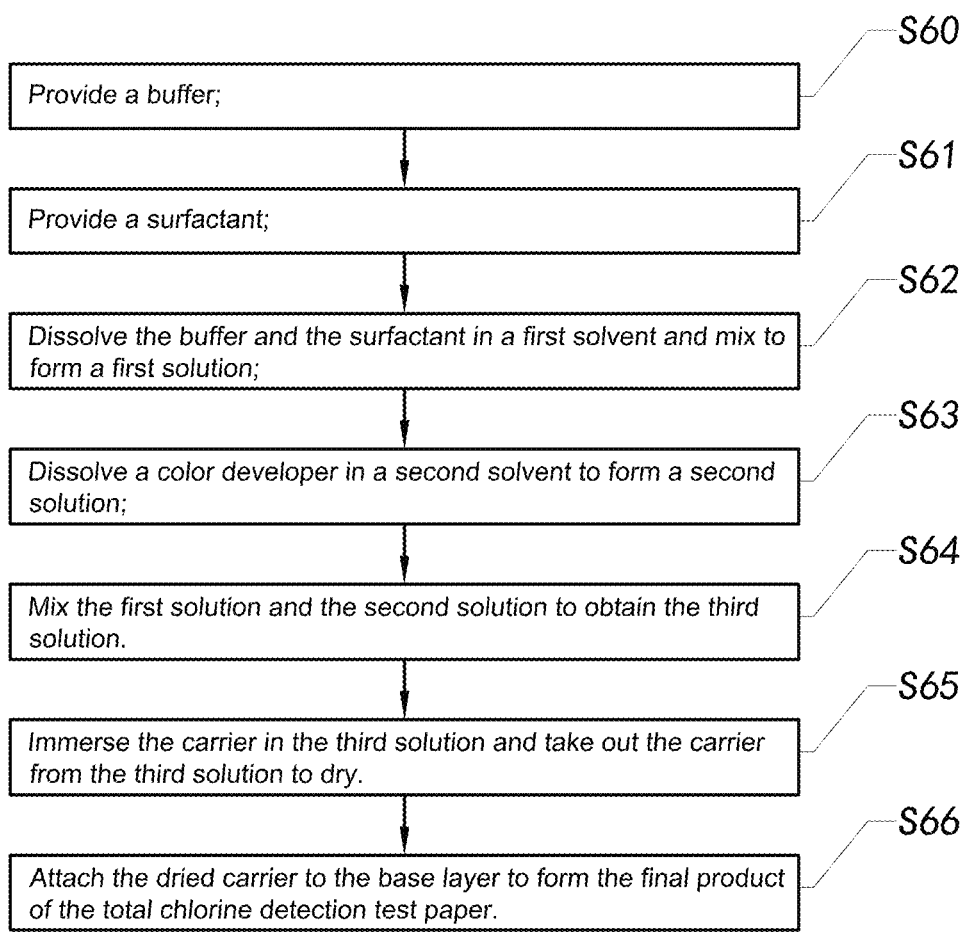
FIG. 20 is a schematic diagram of the overall process of the present invention.

Reference FIG. 20, a preparation method of a total chlorine detection test paper comprises the following steps.

Step S60: Provide a buffer;

In this step, the buffer comprises one or more of citric acid, sodium citrate, disodium hydrogen phosphate, sodium dihydrogen phosphate, TBS (English name: Tris Buffered Saline, Chinese name: Tris Buffered Saline), boric acid, borax, and sodium hydroxide. Through the above steps, the buffer can improve the color response of the chromogen to free available chlorine and provide a more stable color response, and the buffer can complex with the chromogen agent to form a brighter, more brilliant color and stabilize color.

Step S61: Provide a surfactant;

In this step, the surfactant can comprise cationic, anionic, and nonionic surfactants. Specially, the surfactant can include but not limit to one or more of Tween 20, Tween 80, Span 80, BRIJ47 (polyoxyethylene), polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

Step S62: dissolve the buffer and the surfactant in a first solvent and mix to form a first solution;

In this step, the buffer and the surfactant are dissolved in pure water. The amount of surfactant added per 100 ml of solvent ranges from 0.05 g to 3.0 g. The amount of buffer added per 100 ml of solvent ranges from 0.05 g to 6 g. Mix to form the first solution. The first solvent can be water, alcohols or other.

Step S63: dissolve a color developer in a second solvent to form a second solution;

In this step, the second solvent can be water, alcohols or other. The color developer can be. The color developer can be dissolved in ethanol. The amount of color developer added per 100 ml of solvent ranges from 0.01 g-10 g. The color developer comprises one or more of DPD, tetramethylbenzidine, syringaldazine, and vanillin azine.

Step S64: Mix the first solution and the second solution to obtain the third solution.

Step S65: Immerse the carrier 200e in the third solution and take out the carrier 200e from the third solution to dry to obtain a third test paper.

Step S66: Attach the dried carrier 200e to the base layer 100e to form the final product of the total chlorine detection test paper.

Figure 21:
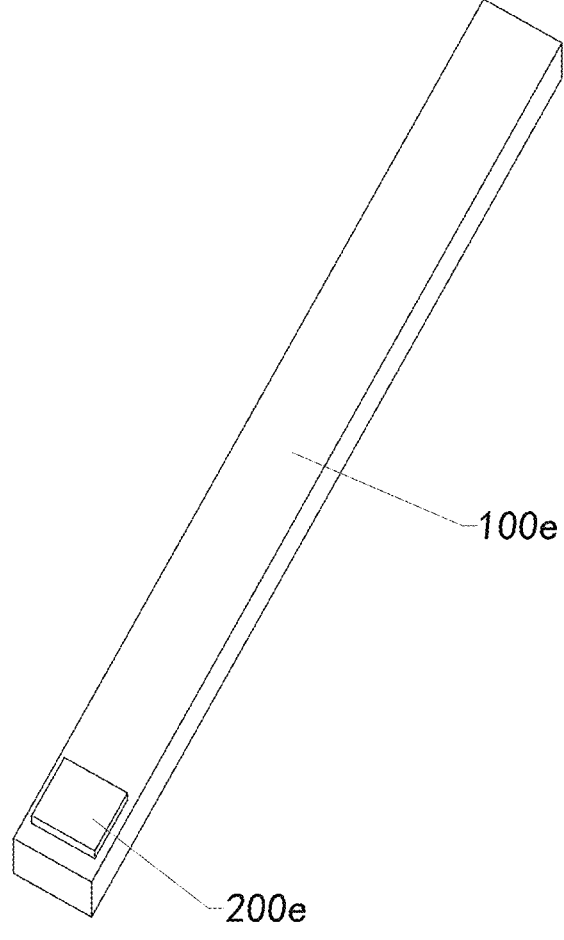
FIG. 21 is a perspective view illustrating the overall structure of a total chlorine detection test paper of a preferred embodiment of the present invention.

Referring to FIG. 21, a total chlorine detection test paper according to a preferred embodiment of the present invention is illustrated. The total chlorine detection test paper comprises the base layer 100e, and the carrier 200e attached to the base layer 100e for carrying a total chlorine detection substance.

The total chlorine detection test paper for water quality detection can be used in various applications, including domestic water, swimming pools, aquariums, and disinfection. This type of test paper is commonly employed to measure total chlorine levels, ensuring water safety and cleanliness. Beyond these areas, total chlorine detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100e is made of a polymer material such as PET (Polyethylene Terephthalate), PEN (Polyethylene Naphthalate), PP (Polypropylene), and PE (Polyethylene). In this embodiment, the base layer 100 is made of PET.

The carrier 200e is used for being immersed in the immersing solutions to carry the total chlorine detection substance. In this embodiment, the carrier 200e is made of a filtering paper. Accordingly, the filtering paper is designed to absorb liquids efficiently, ensuring that the immersing solution, which contains the total chlorine detection substance, is evenly distributed across the carrier 200e. This uniform absorption is crucial for consistent test results.

The filtering paper has a porous structure, which allows it to hold and distribute the total chlorine detection substance effectively. The porosity ensures that the test paper has sufficient surface area for the total chlorine in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the total chlorine detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The total chlorine detection substance on the carrier 200e comprises a color developer wherein the color developer comprises one or more of DPD, tetramethylbenzidine, syringaldazine, and vanillin azine.

Preferably, the total chlorine detection substance is formed by mixing the color developer, the surfactant and the buffer, wherein the buffer comprises one or more of citric acid, sodium citrate, disodium hydrogen phosphate, sodium dihydrogen phosphate, TBS, boric acid, borax, and sodium hydroxide, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

The use of one or more color developers like DPD, tetramethylbenzidine, syringaldazine, and vanillin azine ensure a sensitive and precise colorimetric response to total chlorine. These developers produce distinct and easily observable color changes upon reacting with total chlorine, allowing for accurate detection across a range of total chlorine concentrations.

The addition of the surfactant like Tween 20, Tween 80, Span 80, BRIJ47, polyvinyl pyrrolidone (K30, K90), polyethylene glycol 4000, polyvinyl alcohol, fatty alcohol polyoxyethylene ether, isooctyl alcohol polyoxyethylene ether, and N,N-dimethyl n-octadecylamine aids in improving the wetting properties of the detection substance. These surfactant ensures that the total chlorine detection substance is evenly distributed on the carrier 200e, leading to consistent and uniform test results. The surfactant also helps in preventing the aggregation of the color developers, further enhancing the accuracy of the detection.

As a first example, 4 g citric acid, 0.16 g sodium citrate, and 0.012 g BRIJ47 are dissolved in 500 ml water to form the first solution. 0.36 g tetramethylbenzidine is dissolved in 500 ml ethanol to form the second solution. The first solution and the second solution are mixed to form the third solution. The carrier 200e is immersed into the third solution. Take out the carrier 200e from the third solution to dry the carrier 200e and attach the dried carrier 200e to the base layer 100e to form the final product of the total chlorine detection test paper.

As a second example, 0.05 g TRIS and 0.05 g fatty alcohol polyoxyethylene ether are dissolved in 500 ml water to form the first solution. 0.01 g syringaldazine is dissolved in 500 ml ethanol to form the second solution. The first solution and the second solution are mixed to form the third solution. The carrier 200e is immersed into the third solution. Take out the carrier 200e from the third solution to dry the carrier 200e and attach the dried carrier 200e to the base layer 100e to form the final product of the total chlorine detection test paper.

As a third example, 6 g sodium dihydrogen phosphate and 3 g polyvinyl alcohol are dissolved in 500 ml water to form the first solution. 10 g DPD is dissolved in 500 ml water to form the second solution. The first solution and the second solution are mixed to form the third solution. The carrier 200e is immersed into the third solution. Take out the carrier 200e from the third solution to dry the carrier 200e and attach the dried carrier 200e to the base layer 100e to form the final product of the total chlorine detection test paper.

With reference to FIG. 22, a method for preparing a free bromine detection test paper comprises the following steps.

Step S70: Provide a buffer.

In this step, the buffer comprises one or more of citric acid, sodium citrate, disodium hydrogen phosphate, sodium dihydrogen phosphate, TBS (Tris Buffered Saline, trishydroxymethylaminomethane Buffered Saline), boric acid, borax, and sodium hydroxide. Through the above steps, the buffer can improve the color response of the color developer to free available bromine, and provide a more stable color response, and the buffer can be complexed with the color developer to form a brighter and more gorgeous color, and stabilize the color.

Step S71: Provide a surfactant.

In this step, the surfactant is one or more of Tween 20, Tween 80, Span 80, BRIJ47 (polyoxyethylene), polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine. Through the above step, the surfactant helps the test sample to wet the carrier without adversely affecting the color transition of the color-developing substance in response to free available bromine. In addition, the surfactant can also improve the stability of the color transition of the color-developing substance.

Step S72: Dissolve the surfactant and the buffer in pure water and mix to form a first solution.

In this step, dissolve the surfactant and the buffer in water and mix to form a first solution, the amount of the buffer in 100 ml of water is in the range of 0.01 g-10 g, and the amount of the surfactant in 100 ml of water is in the range of 0.05 g-6 g. Specifically, the surfactant and the buffer are dissolved in 800 ml of water, the amount of the buffer added in each 100 ml of water is in the range of 0.01 g-10 g, and the amount of the surfactant added in each 100 ml of water is in the range of 0.05 g-6 g, and the mixture is mixed to form a first solution.

Step S73: Add anhydrous ethanol to the first solution, and the mixture is mixed to form a second solution.

In this step, 200 ml of anhydrous ethanol is added to the first solution, and the mixture is mixed to form a second solution.

Step S74: Provide a carrier and immerse the carrier in the second solution.

Step S75: Take out the carrier from the second solution, and dry the carrier to obtain a first test paper.

In this step, the carrier is taken out from the second solution, and the carrier is dried at 100 degrees Celsius to obtain a first test paper.

Step S76: Provide a color developer, which is one or more of DPD, tetramethylbenzidine, syringaldazine, and vanillin azine, and dissolving the color developer in anhydrous ethanol to form a third solution.

In this step, a color developer, which comprises one or more of DPD, tetramethylbenzidine, syringaldazine, and vanillin azine, is provided, and the color developer is dissolved in anhydrous ethanol, and the step of forming the third solution is: providing a coloring developer, which is DPD (N, N-diethyl-1,4-phenylenediamine sulfate, molecular formula: $NH_2$—$C_6H_4$—$N(C_2H_5)2·H_2SO_4$), tetramethylbenzidine, syringaldazine, and vanillin azine, and dissolving the color developer in anhydrous ethanol, the amount of the color developer added to every 100 ml of anhydrous ethanol is in the range of 0.01 g-10 g, and mixing the mixture to form the third solution.

Step S77: Immerse the first test paper in the third solution.

Step S78: Take out the first test paper from the third solution, and dry the first test paper to obtain a bromine detection test paper.

In this step, take out the first test paper from the third solution, and dry the first test paper at 80 degrees Celsius to obtain a bromine detection test paper.

Through the above steps, the present invention provide a method for preparing a bromine detection test paper, wherein the method comprises the following steps: providing a buffer; providing a surfactant; dissolving the surfactant and the buffer in pure water, mixing to form a first solution; adding anhydrous ethanol to the first solution, mixing to form a second solution; providing a carrier, immersing the carrier in the second solution; taking out the carrier from the second solution, and drying the carrier to obtain a first test paper; providing a color developer, the color developer comprises one or more of DPD, tetramethylbenzidine, syringaldazine, and vanillinazine, dissolving the color developer in anhydrous ethanol to form a third solution; immersing the first test paper in the third solution; taking out the first test paper from the third solution, and drying the first test paper to obtain a bromine detection test paper, so that a user can put the bromine detection test paper into water for detection, and the color developer reacts with active bromine in water to generate a purple-red compound, the color depth of which is proportional to the bromine concentration, and it can be compared with a color card to accurately detect the bromine content in water. The buffer can improve the color response of the color developer to free available bromine and provide a more stable color response, and the buffer can be complexed with the color developer to form a brighter and more gorgeous color and stabilize the color. Specifically, the surfactant helps the test sample to wet the carrier without adversely affecting the color transition of the color developer in response to free available bromine. In addition, the surfactant can also improve the stability of the color transition of the color developer. The comparison color card includes a first purple-red color block, a second purple-red color block, a third purple-red color block, a fourth purple-red color block, and a fifth purple-red color block, and the first purple-red color block, the second purple-red color block, the third purple-red color block, the fourth purple-red color block, and the fifth purple-red color block are arranged in sequence from bottom to top along the color card, and the color depth of the first purple-red color block, the second purple-red color block, the third purple-red color block, the fourth purple-red color block, and the fifth purple-red color block increases in sequence, wherein the detection result corresponding to the first purple-red color block is 0.5 mg/L, the detection result corresponding to the second purple-red color block is 1.0 mg/L, the detection result corresponding to the third purple-red color block is 3.0 mg/L, the detection result corresponding to the fourth purple-red color block is 5.0 mg/L, and the detection result corresponding to the fifth purple-red color block is 10 mg/L.

Figure 23:
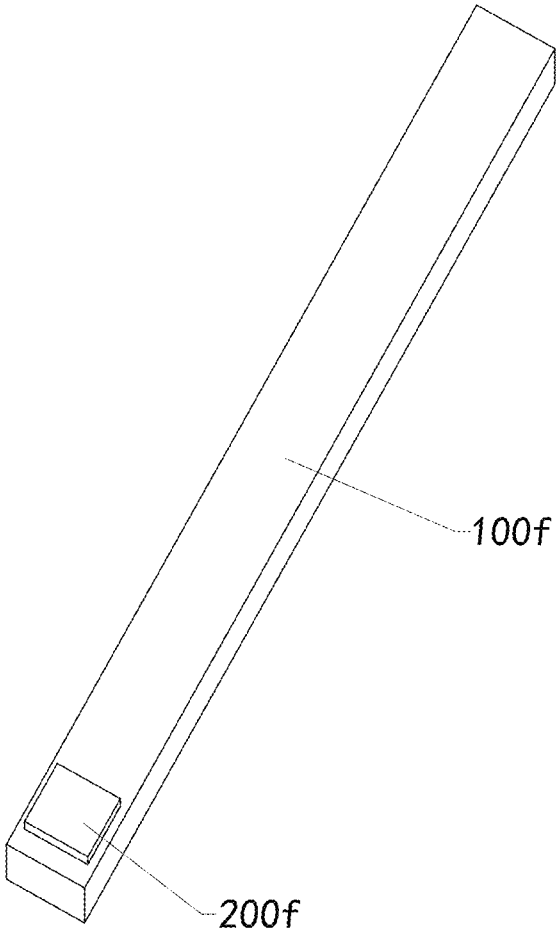
FIG. 23 is a perspective view illustrating the overall structure of a bromine detection test paper of the first preferred embodiment of the present invention.

Referring to FIG. 23 of the drawing, a bromine detection test paper according to a preferred embodiment of the present invention is illustrated. The bromine detection test paper comprises a base layer 100f, and a carrier 200f attached to the base layer 100f for carrying a bromine detection substance.

The bromine detection test paper for water quality detection can be used in various applications, including domestic water, swimming pools, aquariums, and disinfection. This type of test paper is commonly employed to measure bromine levels, ensuring water safety and cleanliness. Beyond these areas, bromine detection test paper can also be extended to environmental monitoring, where it can be used to check the quality of drinking water in public water systems, groundwater testing, and even wastewater management. Additionally, it has potential applications in the food and beverage industry, where water quality is crucial for production, and in laboratory research, where precise measurements of water composition are required for experiments.

The base layer 100f is made of a polymer material such as PET (Polyethylene Terephthalate), PEN (Polyethylene Naphthalate), PP (Polypropylene), and PE (Polyethylene). In this embodiment, the base layer 100f is made of PET.

PET is known for its excellent mechanical strength, providing a robust and durable base layer that can withstand handling and environmental stress during use and storage. PET exhibits strong resistance to chemicals, including acids and bases. This characteristic ensures that the base layer 100f does not degrade or react when exposed to various substances, preserving the integrity of the bromine detection test paper.

PET has low shrinkage and maintains its dimensions under different environmental conditions, such as changes in temperature and humidity. This stability is crucial for the consistent performance of the test paper. PET also offers excellent barrier properties against moisture and gases, protecting the bromine detection substance from premature degradation due to exposure to air or moisture. This extends the shelf life and reliability of the test paper.

PET can be widely used in manufacturing due to its ease of processing. It can be easily extruded, laminated, or coated, making it a versatile material for creating a consistent and high-quality base layer 100f.

The carrier 200f is used for being immersed in the immersing solutions to carry the bromine detection substance. In this embodiment, the carrier 200f is made of a filtering paper. Accordingly, the filtering paper is designed to absorb liquids efficiently, ensuring that the immersing solution, which contains the bromine detection substance, is evenly distributed across the carrier 200*f*. This uniform absorption is crucial for consistent test results.

The filtering paper has a porous structure, which allows it to hold and distribute the bromine detection substance effectively. The porosity ensures that the test paper has sufficient surface area for the bromine in the water to react with the detection substance, leading to a more accurate color change. The filtering paper is flexible and easy to handle, making it ideal for manufacturing processes where the carrier needs to be immersed, dried, and further processed. Its flexibility also allows it to conform to different shapes or sizes as needed.

Since filtering paper is chemically inert and does not react with the bromine detection substance, it minimizes any potential interference in the color reaction, ensuring that the test results are reliable and accurate.

As a biodegradable material, the filtering paper also contributes to the environmental sustainability of the product, particularly when compared to synthetic alternatives. This can be an important factor for consumers and industries focused on eco-friendly solutions.

The bromine detection substance on the carrier 200*f* comprises a color developer which comprises one or more of DPD, tetramethylbenzidine, syringaldehyde azine, and vanillin azine.

Preferably, the bromine detection substance is formed by mixing bromine color developer, buffer and surfactant, the bromine color developer comprises one or more of DPD, tetramethylbenzidine, syringaldazine and vanillinazine; the buffer comprises one or more of citric acid, sodium citrate, disodium hydrogen phosphate, sodium dihydrogen phosphate, TRIS, boric acid, borax and sodium hydroxide; the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.

The use of one or more developers like DPD, tetramethylbenzidine, syringaldazine, and vanillinazine ensures a sensitive and precise colorimetric response to bromine. These developers produce distinct and easily observable color changes upon reacting with bromine, allowing for accurate detection across a range of bromine concentrations.

The inclusion of the buffer, comprising compounds such as citric acid, sodium citrate, disodium hydrogen phosphate, sodium dihydrogen phosphate, TRIS, boric acid, borax, and sodium hydroxide, is crucial for maintaining a stable pH environment. This stabilization ensures that the bromine color developers react consistently, providing reliable and reproducible results. The buffer also helps to enhance the intensity and stability of the color change, making the detection process more robust.

The addition of surfactants like Tween 20, Tween 80, Span 80, BRIJ47, polyvinyl pyrrolidone (K30, K90), polyethylene glycol 4000, polyvinyl alcohol, fatty alcohol polyoxyethylene ether, isooctyl alcohol polyoxyethylene ether, and N,N-dimethyl n-octadecylamine aids in improving the wetting properties of the detection substance. These surfactant ensures that the bromine detection substance is evenly distributed on the carrier 200*f*, leading to consistent and uniform test results. The surfactant also helps in preventing the aggregation of the color developers, further enhancing the accuracy of the detection.

The use of carefully selected buffer and surfactant contributes to the overall stability of the bromine detection substance. By preventing the degradation of the color developers and ensuring a stable pH environment, the formulation is protected against environmental factors such as temperature fluctuations and humidity. This leads to an extended shelf life, making the detection substance more reliable over time.

The present invention further provides a method for preparing the bromine detection test paper, and the method comprises the steps of immersing the carrier 200*f* in a first immersing solution and immersing the carrier 200*f* in a second immersing solution.

In the step of immersing the carrier 200*f* in the first immersing solution the surfactant and the buffer are dissolved in water and mixed, and anhydrous ethanol is then added and mixed to obtain the first immersing solution, the amount of the buffer in 100 fml of water is in the range of 0.01 g-10 g, and the amount of the surfactant in 100 fml of water is in the range of 0.05 g-6 g, the volume of anhydrous ethanol is one fourth of the volume of water. The carrier 200*f* is then immersed in the first immersing solution, and is taken out from the first immersing solution, and dried the carrier at 100*f* degrees Celsius to obtain a first test paper.

In the step of immersing the carrier 200*f* in the second immersing solution, the color developer, which comprises one or more of DPD, tetramethylbenzidine, syringaldazine, and vanillin azine, is dissolved in anhydrous ethanol and heated to form a second immersing solution, the amount of the color developer added to every 100 fml of anhydrous ethanol is in the range of 0.01 g-10 g. And then the first test paper is immersed in the second immersing solution, and finally is taken ou from the second immersing solution and dried at 80 degrees Celsius to obtain the bromine detection test paper.

In the manufacturing process of the bromine detection test paper, an integral piece of the carriers 200*f* is immersed into the above two immersing solution and dried, and then is cut into small pieces and a piece of the carrier 200*f* can be attached to the base layer 100*f* to form the final product of the bromine detection test paper.

As a first example, 4.05 g polyethylene glycol 4000, 1.98 g citric acid, 2.67 g sodium citrate are dissolved in 800 ml water and mixed, and then 200 ml anhydrous ethanol is added and mixed to obtain the first immersing solution. The second immersing solution is prepared by dissolving 3.25 g DPD in 1000 ml anhydrous ethanol.

As a second example, 6.86 g isooctyl alcohol polyoxyethylene ether, 1.22 g boric acid, and 7.89 g borax are dissolved in 800 ml water and mixed, and then 200 ml anhydrous ethanol is added and mixed to obtain the first immersing solution. The second immersing solution is prepared by dissolving 2.43 g tetramethylbenzidine in 1000 ml anhydrous ethanol.

As a third example, 0.523 g Tween 20, 1.57 g disodium hydrogen phosphate, and 2.26 g sodium dihydrogen phosphate are dissolved in 800 ml water and mixed, and then 200 ml anhydrous ethanol is added and mixed to obtain the first immersing solution. The second immersing solution is prepared by dissolving 0.385 g syringaldazine in 1000 ml anhydrous ethanol.

As a fourth example, 3.15 g N,N-dimethyl n-octadecylamine, 1.25 g TRIS are dissolved in 800 ml water and mixed, and then 200 ml anhydrous ethanol is added and mixed to obtain the first immersing solution. The second immersing solution is prepared by dissolving 6.01 g vanillin azine in 1000 ml anhydrous ethanol.

The above is one or more implementation methods provided in combination with the specific content, and it is not intended that the specific implementation of the present invention is limited to these descriptions. Anything similar to or identical to the method, structure, etc. of the present invention, or a number of technical deductions or substitutions made on the premise of the concept of the present invention, should be regarded as the scope of protection of the present invention.

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 24:
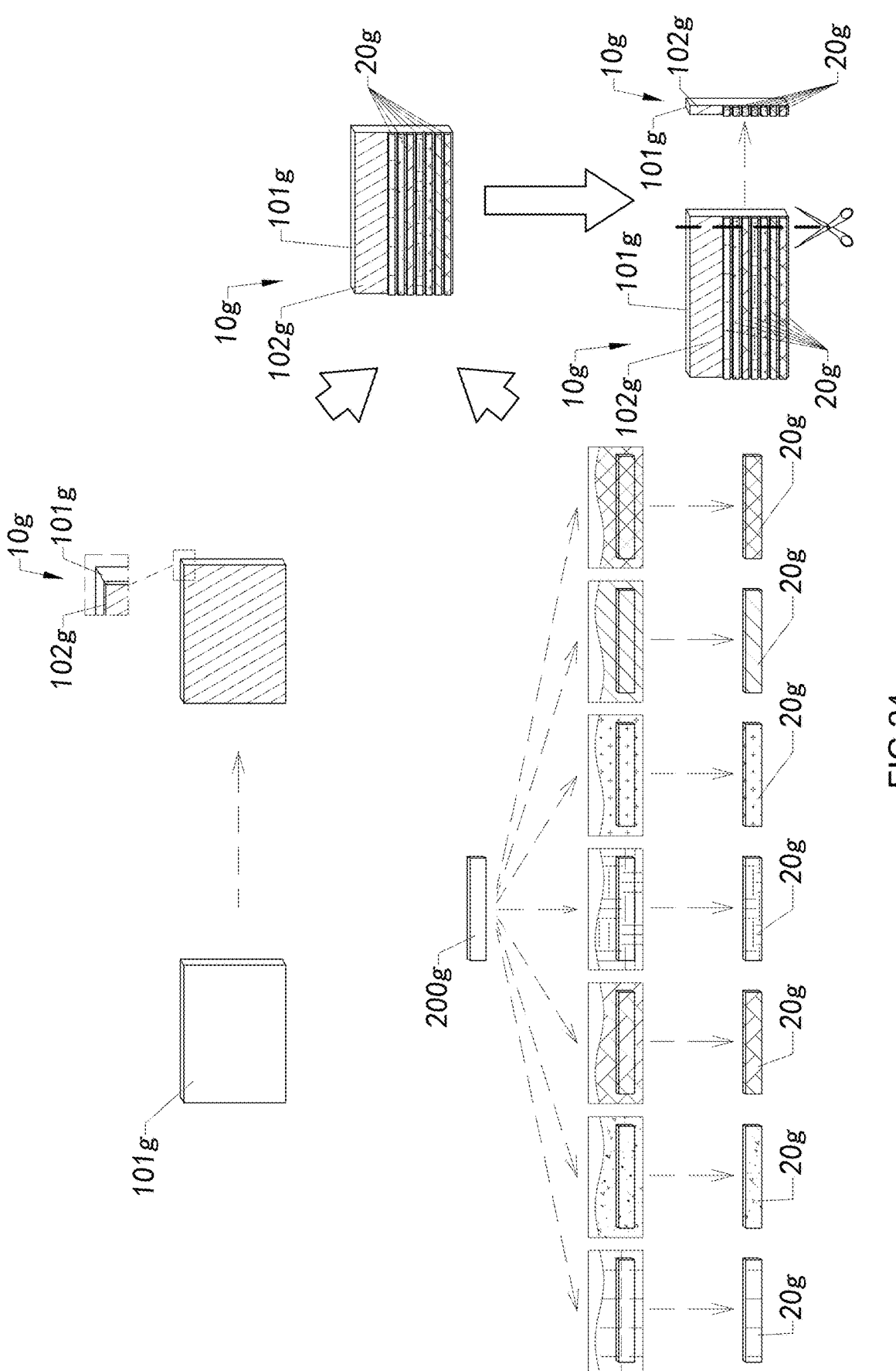
FIG. 24 is a perspective view illustrating a method of preparing a multifunctional detection test paper of a preferred embodiment of the present invention.
Figure 25:
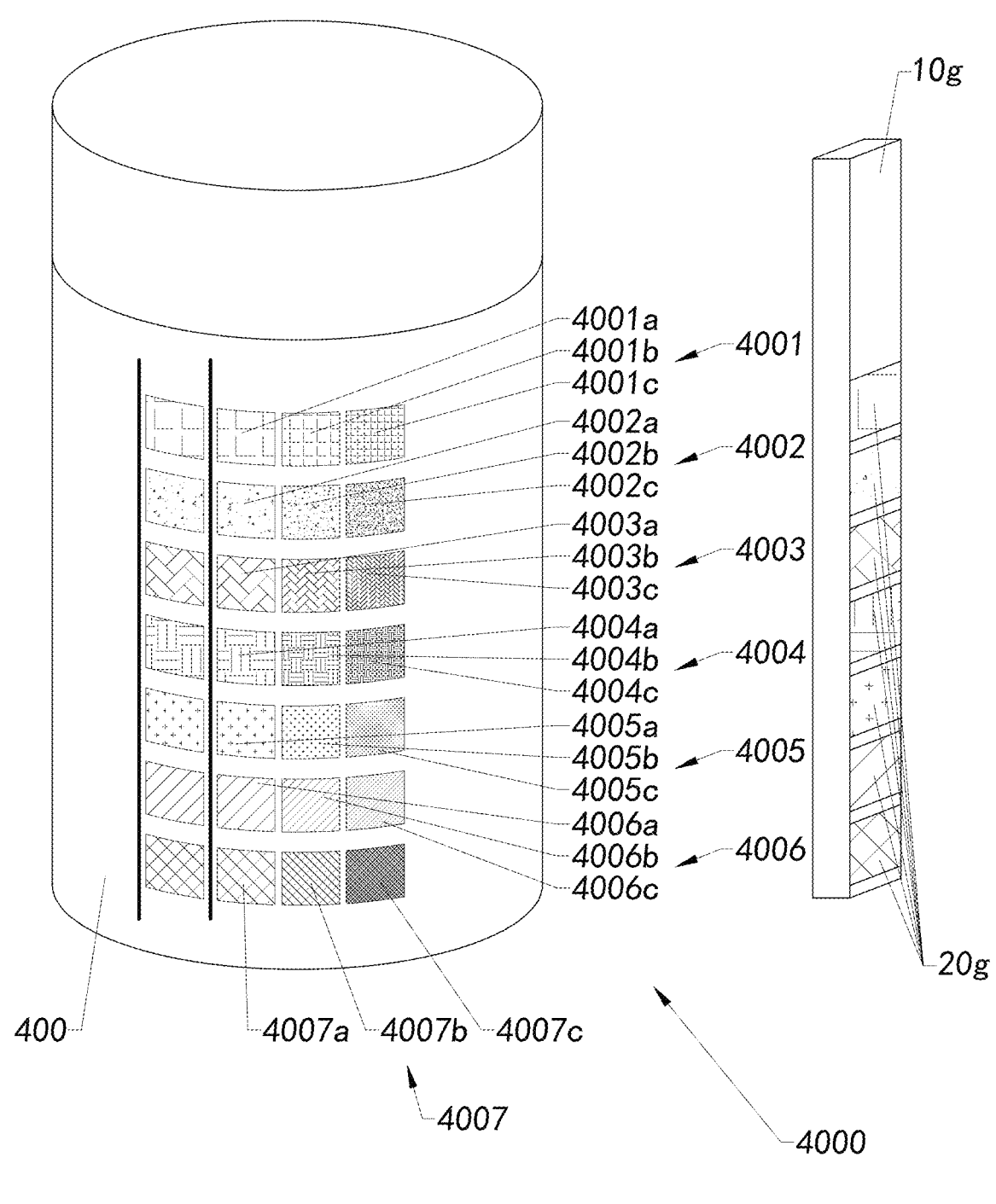
FIG. 25 is a perspective view illustrating a container storing with the multifunctional detection test paper of a preferred embodiment of the present invention.

Referring to FIG. 24, a multifunctional detection test paper according to a preferred embodiment of the present invention is illustrated. The multifunctional detection test paper comprises a base 10g; and a plurality of test modules 20g, each of the test modules 20g being configured to detect at least one of a combination of pH, total alkalinity, cyanuric acid, total chlorine, bromine, free chlorine and water hardness; wherein the test modules 20g are attached to the base 10g.

Moreover, the base 10g comprises a base layer 101g and a hydrophobic layer 102g, wherein the hydrophobic layer 102g is coated on the base layer 101g, and the test modules 20g are spaced apart on the hydrophobic layer 101g, thereby preventing color bleeding. Each of the test modules 20g comprises a carrier 200g and a detection substance provided on the carrier 200g, wherein the carrier 200g is for carrying the detection substance. The test modules 20g can detect pH, total alkalinity, cyanuric acid, total chlorine, bromine, free chlorine or water hardness.

The prevention of cross-contamination between test zones formed by the test modules 20g is not an inherent property of the base layer 101g itself. Instead, it is achieved through an additional manufacturing step, whereby a proprietary hydrophobic coating solution is uniformly applied to the base layer 101g and then dried. This hydrophobic treatment on the base layer 101g minimizes the risk of dye migration or cross-contamination between adjacent test zones on the multifunctional detection test paper. Our invention represents an improvement over standard methods and addresses common issues associated with cross-zone interference in multi-analyte test strips.

One of the test modules 20g is configured to detect free chlorine and comprises a carrier 200g and a detection substance provided on the carrier 200g, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine.

One of the test modules 20g is configured to detect water hardness and comprises a carrier 200g and a detection substance provided on the carrier 200g, wherein the detection substance is formed by immersing the carrier 200g in an immersing solution containing a color developer and a buffer, wherein the color developer comprises one or more of calcium magnesium reagent, chrome black T, calcium carboxylic acid, azo arsine 1, and azo arsine 3, wherein the buffer comprises one or more of citric acid, disodium EDTA, sodium citrate, disodium EDTA, disodium hydrogen phosphate, sodium dihydrogen phosphate, TRIS, boric acid, borax, and sodium hydroxide.

One of the test modules 20g is configured to detect pH and comprises a carrier 200g and a detection substance provided on the carrier 200g, wherein the detection substance is formed by mixing a color developer and a surfactant, wherein the color developer comprises one or more of phenol red, sodium phenol red, bromocresol green, sodium bromocresol green, bromophenol blue, bromothymol blue, cresol red, sodium cresol red, and xylenol orange, wherein the surfactant comprises one or more of Tween 20, Tween 80, Span 80, BRIJ 47, polyvinylpyrrolidone K30, polyvinylpyrrolidone K90, polyethylene glycol 4000, polyvinyl alcohol, fatty alcohol ethoxylate, isooctyl alcohol ethoxylate N, and N,N-dimethyloctadecylamine.

One of the test modules 20g is configured to detect cyanuric acid and comprises a carrier 200g and a detection substance provided on the carrier 200g, wherein the detection substance is formed by mixing a color rendering agent, a surfactant and melamine, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, and isooctanol polyoxyethylene ether and N,N-dimethyldiocta-decylamine.

One of the test modules 20g is configured to detect total alkalinity and comprises a carrier 200g and a detection substance provided on the carrier 200g, wherein the detection substance is formed by mixing a color rendering agent and a surfactant, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

One of the test modules 20g is configured to detect total chlorine and comprises a carrier 200g and a detection substance provided on the carrier 200g, wherein the detection substance is formed by mixing a buffer, a surfactant and a color developer, wherein the buffer comprises one or more of citric acid, sodium citrate, disodium hydrogen phosphate, sodium dihydrogen phosphate, TBS, boric acid, borax, and sodium hydroxide, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine, wherein the color developer comprises one or more of DPD, tetramethylbenzidine, syringaldazine, and vanillin azine.

One of the test modules 20g is configured to detect bromine and comprises a carrier 200g and a detection substance provided on the carrier 200g, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.

As a preferred embodiment of the invention, the hydrophobic layer 102g is formed by coating a coating solution on the base layer 101g, wherein the coating solution is mixed by a organosilicon compound, a modifying agent and a molding agent, wherein the organosilicon compound comprises one or more of silicon dioxide, dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises one or more of sodium hydroxide, lithium hydroxide, ammonia, sodium bicarbonate, sodium acetate, sodium citrate, and potassium citrate.

With reference to FIG. 24, a preparation method of multifunctional detection test paper comprises the following steps.

Step S81: Provide a base 10g;

The step of providing the base further comprises the following steps:

Provide a base layer 101g, and

Form a hydrophobic layer 102g with the base layer 101g.

In this step, the base layer 101g is made of a polymer material such as PET (Polyethylene Terephthalate), PEN (Polyethylene Naphthalate), PP (Polypropylene), and PE (Polyethylene). In this embodiment, the base layer 101g is made of PET. PET is known for its excellent mechanical strength, providing a robust and durable base layer 101g that can withstand handling and environmental stress during use and storage. PET exhibits strong resistance to chemicals, including acids and bases. This characteristic ensures that the base layer 101g does not degrade or react when exposed to various substances, preserving the integrity of the multifunction detection test paper.

The step of forming the hydrophobic layer 102g comprises the following steps:

Provide a coating solution 102g; and

Coat the coating solution on the base layer 101g to form the base 10g with a hydrophobic layer 102g.

In this step, the coating solution 102g can be mixed by a silicone containing organic compound, a modifying agent and a molding agent.

The silicone containing organic compound can be, but is not limited to, silicon dioxide, dodecylsilane, tetradecylsilane, cetyltrimethoxysilane, octadecylsilane, dimethyloctadecylchlorosilane, methacryloxypropylsilane.

The modifying agent can be, but is not limited to, hydrochloric acid, sulfuric acid, nitric acid, phosphoric acid, acetic acid, oxalic acid, citric acid, salicylic acid.

The molding agent can be, but is not limited to, sodium hydroxide, lithium hydroxide, ammonia, sodium bicarbonate, sodium acetate, sodium citrate, potassium citrate.

As a first example, silicon dioxide 0.02 g, trimethoxysilane 0.06 g, salicylic acid 0.1 g, glacial acetic acid 100 ml, and sodium citrate 0.6 g are dissolved in 1000 ml water. Stir the mixed solution until it is in suspension to obtain the coating solution.

As a second example, octadecylsilane 0.002 g, HCl 10 ml, and NaOH 0.06 g are dissolved in 1000 ml water. Stir the mixed solution until it is in suspension to obtain the coating solution.

As a third example, silicon dioxide 2 g, glacial acetic acid 200 ml, and sodium acetate 2 g are dissolved in 1000 ml water. Stir the mixed solution until it is in suspension to obtain the coating solution.

Further, before coating, the base layer 101g can be preheated, and then the coating solution is evenly coated to the base layer 101g. The hydrophobic layer 102g is formed with the base layer 101g and can be dried to obtain the final base 10g.

The base layer 101g with the hydrophobic layer 102g reduces color mixing.

In this step, in the manufacturing process, both the base layer 101g (such as PET film) and the coating solution are positioned in designated locations within an apparatus. Once positioned, the machine is activated, including its heating mechanisms, to begin the process. Following a preheating phase, the base layer 101g is advanced through the system by a traction mechanism, ensuring consistent movement through each stage.

As the base layer 101g moves, the coating mechanism applies an even layer of the coating solution across the entire surface of the base layer 101g. This coating process ensures a uniform distribution, which is essential for the desired hydrophobic properties of the final product. Immediately following the application of the coating solution, the base layer 101g is conveyed through a heating unit, where the coating layer is subjected to rapid drying. This drying phase is completed in a short period, allowing the coating layer to solidify and adhere securely to the base layer 101g surface without impairing its structural integrity.

After passing through the heating unit, the coated base layer 101g is collected and wound by the traction mechanism, forming a roll of the completed product ready for subsequent processing or cutting. This method yields a coated substrate with optimal hydrophobic characteristics and high uniformity, providing enhanced performance in end-use applications.

Step S82: Provide a multiplicity of test modules 20g, each test module 20g can detect at least one or more of PH, cyanuric acid, bromine, total alkalinity, total chlorine, free chlorine and total hardness.

In this step, the carriers 200g are immersed into different detection substance to obtain the test modules 20g.

Step S83: Attach the test modules 20g to the base to obtain a multifunctional detection test paper.

The final product, once coated and dried, can be cut or trimmed to predetermined dimensions and sizes according to specific requirements.

The present invention further provides a container 400 for storing a plurality of the multifunctional detection test papers, and a plurality of color blocks 4000 are painted on an outer surface of the container 400 for indicating the concentration levels of corresponding substance.

In this embodiment, the plurality of color blocks 4000 comprises a set of total hardness color blocks 4001, a set of free chlorine color blocks 4002, a set of bromine color blocks 4003, a set of total chlorine color blocks 4004, a set of cyanuric acid color blocks 4005, a set of total alkalinity color blocks 4006 and a set of pH color blocks 4007.

The total hardness color blocks 4001, the free chlorine color blocks 4002, the bromine color blocks 4003, the total chlorine color blocks 4004, the cyanuric acid color blocks 4005, the total alkalinity color blocks 4006 and the pH color blocks 4007 are arranged in order in a vertical row, corresponding to the multiple detection areas on the multifunctional detection test paper.

Each color blocks (4001, 4002, 4003, 4004, 4005, 4006, 4007) include multiple color blocks arranged laterally, with colors gradually shifting to represent variations in concentration levels.

For example, the total hardness color blocks 4001 comprises a first purple-red color block 4001*a*, a second purple-red color block 4001*b*, and a third purple-red color block 4001*c*. The detection result corresponding to the first purple-red color block 4001*a* is 0.5 mg/L, the detection result corresponding to the second purple-red color block 4001*b* is 1.0 mg/L, the detection result corresponding to the third purple-red color block 4001*c* is 3.0 mg/L. The number of color blocks is provided as an example only and may be increased as needed to allow for finer gradation in concentration levels.

For example, the free chlorine color blocks 4002 comprises a first blue color block 4002*a*, a second blue color block 4002*b*, and a third blue color block 4002*c*. The detection result corresponding to the first blue color block 4002*a* is 0.5 mg/L, the detection result corresponding to the second blue color block 4002*b* is 1.0 mg/L, the detection result corresponding to the third blue color block 4002*c* is 3.0 mg/L. The number of color blocks is provided as an example only and may be increased as needed to allow for finer gradation in concentration levels.

For example, the bromine color blocks 4003 comprises a first green color block 4003*a*, a second green color block 4003*b*, and a third green color block 4003*c*. The detection result corresponding to the first green color block 4003*a* is 0.5 mg/L, the detection result corresponding to the second green color block 4003*b* is 1.0 mg/L, the detection result corresponding to the third green color block 4003*c* is 3.0 mg/L. The number of color blocks is provided as an example only and may be increased as needed to allow for finer gradation in concentration levels.

For example, the total chlorine color blocks 4004 comprises a first gray color block 4004*a*, a second gray color block 4004*b*, and a third gray color block 4004*c*. The detection result corresponding to the first gray color block 4004*a* is 0.5 mg/L, the detection result corresponding to the second gray color block 4004*b* is 1.0 mg/L, the detection result corresponding to the third gray color block 4004*c* is 3.0 mg/L. The number of color blocks is provided as an example only and may be increased as needed to allow for finer gradation in concentration levels.

For example, the cyanuric acid color blocks 4005 comprises a first orange color block 4005*a*, a second orange color block 4005*b*, and a third orange color block 4005*c*. The detection result corresponding to the first orange color block 4005*a* is 0.5 mg/L, the detection result corresponding to the second orange color block 4005*b* is 1.0 mg/L, the detection result corresponding to the third orange color block 4005*c* is 3.0 mg/L. The number of color blocks is provided as an example only and may be increased as needed to allow for finer gradation in concentration levels.

For example, the total alkalinity color blocks 4006 comprises a first rose-red color block 4006*a*, a second rose-red color block 4006*b*, and a third rose-red color block 4006*c*. The detection result corresponding to the first rose-red color block 4006*a* is 0.5 mg/L, the detection result corresponding to the second rose-red color block 4006*b* is 1.0 mg/L, the detection result corresponding to the third rose-red color block 4006*c* is 3.0 mg/L. The number of color blocks is provided as an example only and may be increased as needed to allow for finer gradation in concentration levels.

For example, the pH color blocks 4007 comprises a first yellowish-brown color block 4007*a*, a second yellowish-brown color block 4007*b*, and a third yellowish-brown color block 4007*c*. The detection result corresponding to the first yellowish-brown color block 4007*a* is 6.8, the detection result corresponding to the second yellowish-brown color block 4007*b* is 7.2 mg/L, the detection result corresponding to the third yellowish-brown color block 4007*c* is 7.6 mg/L. The number of color blocks is provided as an example only and may be increased as needed to allow for finer gradation in concentration levels.

The inclusion of color blocks 4000 directly on the container 400 provides an easy and immediate reference for users to compare the color change of the test paper with the standard color blocks. This feature simplifies the process of interpreting test results, as users can directly compare the test paper to the color blocks on the container 400 without needing a separate reference card.

The color blocks 4000 being painted on the container 400 ensure that the reference guide is always available with the test papers. This design reduces the risk of misplacing or losing the color reference, making the test kit more user-friendly and accessible, especially in field conditions.

Since the color blocks 4000 are painted on the container 400, they are less likely to be damaged or worn compared to a separate paper reference card. This increases the durability of the test kit, ensuring that the reference guide remains intact and legible over time. The color blocks 400 may be painted on an outer surface of the container 400, or the color blocks 400 are painted on a paper sheet and the paper sheet is then attached on the container body of the container 400.

Combining the test paper storage and the color reference in one container makes the entire testing kit more compact and portable. Users can carry the container with them easily, knowing that they have everything needed for water quality testing in one convenient package.

Figure 26:
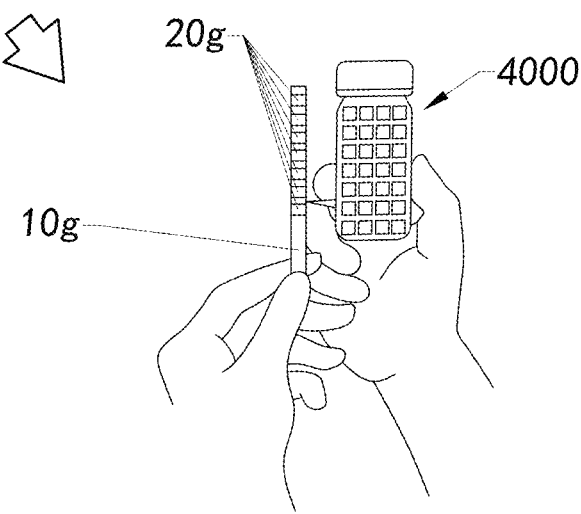
FIG. 26 is a perspective view illustrating a method of testing water quality of a preferred embodiment of the present invention.

Referring to FIG. 26, a method of testing water quality comprises the following steps.

Immersing a plurality of test modules 20*g* of a multifunctional detection test paper into water, each of the test modules 20*g* being configured to detect at least one of a combination of pH, total alkalinity, cyanuric acid, total chlorine, bromine, free chlorine and water hardness;

Removing the multifunctional detection test paper from water and placing it horizontally for a predetermined period; and Comparing the colors of the test modules 20*g* of the multifunctional detection test paper with a color reference.

The method further comprises a step of preventing cross-contamination of colors between the respective test modules 20*g* by using a hydrophobic layer as water flows along the multifunctional detection test paper to each of the test modules 20*g*.

Figure 27:
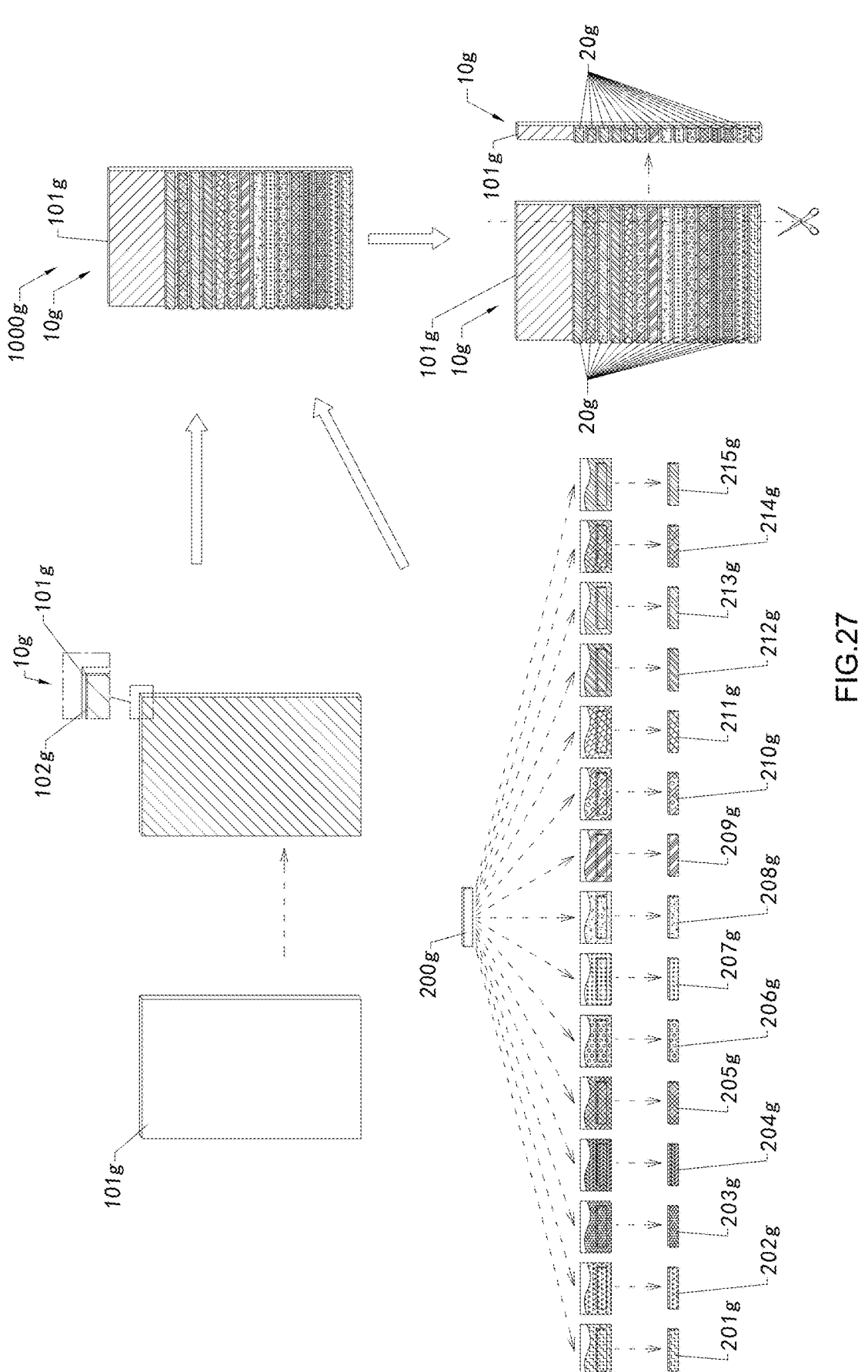
FIG. 27 is a perspective view illustrating a method of preparing a multifunctional detection test paper of a multifunctional detection test kit of another preferred embodiment of the present invention.
Figure 28:
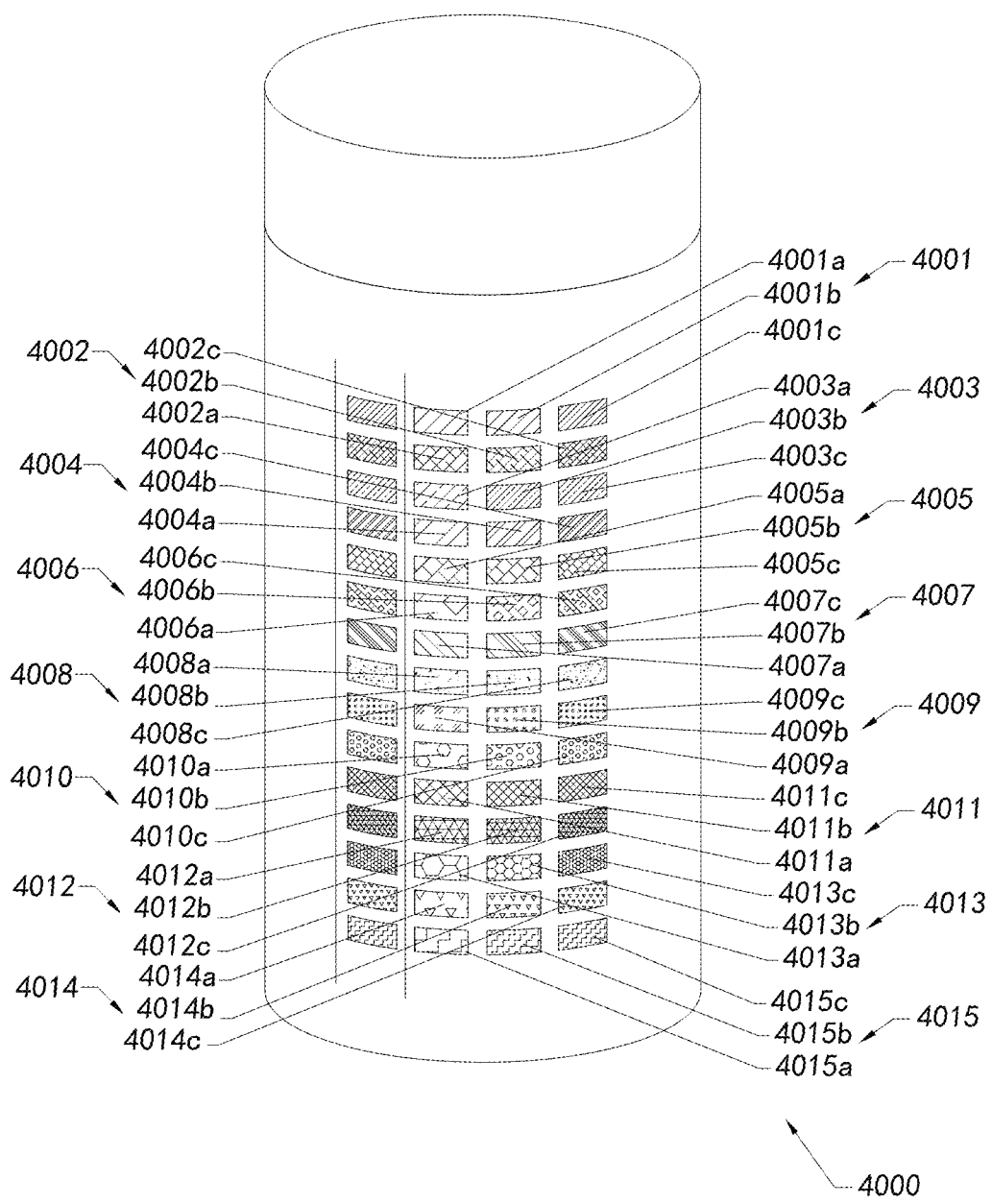
FIG. 28 is a perspective view illustrating a container storing with the multifunctional detection test paper according to the above another preferred embodiment of the present invention.
Figure 29:
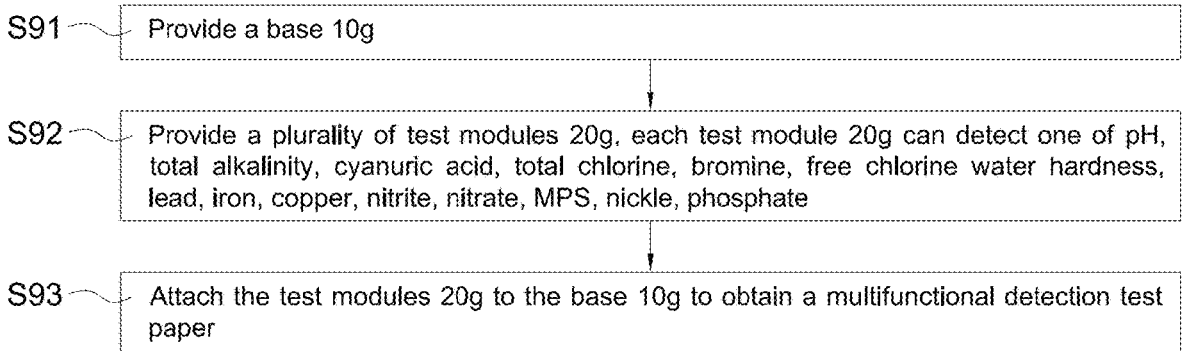
FIG. 29 is a perspective view illustrating a method of testing water quality according to the above another preferred embodiment of the present invention.

Referring to FIG. 27 to FIG. 29, a multifunctional detection test kit according to a preferred embodiment of the present invention is illustrated. The multifunctional detection test paper comprises a multifunctional detection test paper 1000*g* which comprises a base 10*g*; and a plurality of test modules 20*g* attached on the base 10*g*, each of the test modules 20*g* being configured to detect at least one of pH, total alkalinity, cyanuric acid, total chlorine, bromine, free chlorine water hardness, lead, iron, copper, nitrite, nitrate, MPS, nickel, phosphate; wherein the test modules 20g can be attached to the base 10g by a glue.

Moreover, the base 10g comprises a base layer 100g and a hydrophobic layer 101g, wherein the hydrophobic layer 101g is coated on the base layer 100g, and the test modules 20g are spaced apart on the hydrophobic layer 101g, thereby preventing color bleeding. Each of the test modules 20g comprises a carrier 200g and a detection substance provided on the carrier 200g, wherein the carrier 200g is arranged for carrying the detection substance. The test modules 20g can detect one or more of pH, total alkalinity, cyanuric acid, total chlorine, bromine, free chlorine, water hardness, lead, iron, copper, nitrite, nitrate, MPS, nickel, phosphate.

The prevention of cross-contamination between test zones formed by the test modules 20g is not an inherent property of the base layer 100g itself. Instead, it is achieved through an additional manufacturing step, whereby a proprietary hydrophobic coating solution is uniformly applied to the base layer 100g and then dried. This hydrophobic treatment on the base layer 100g minimizes the risk of dye migration or cross-contamination between adjacent test zones on the multifunctional detection test paper. Our invention represents an improvement over standard methods and addresses common issues associated with cross-zone interference in multi-analyte test strips.

As a preferred embodiment of the invention, the hydrophobic layer 101g is formed by coating a coating solution on the base layer 100g, wherein the coating solution is mixed by an organosilicon compound, a modifying agent and a molding agent, wherein the organosilicon compound comprises one or more of silicon dioxide, dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises one or more of sodium hydroxide, lithium hydroxide, ammonia, sodium bicarbonate, sodium acetate, sodium citrate, and potassium citrate.

The test modules 20g comprises a first test modules 201g which is configured to detect free chlorine and comprises a carrier 200g and a detection substance provided on the carrier 200g, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine.

The test modules 20g comprises a second test modules 202g which is configured to detect water hardness and comprises a carrier 200g and a detection substance provided on the carrier 200g, wherein the detection substance is formed by immersing the carrier 200g in an immersing solution containing a color developer and a buffer, wherein the color developer comprises one or more of calcium magnesium reagent, chrome black T, calcium carboxylic acid, azo arsine 1, and azo arsine 3, wherein the buffer comprises one or more of citric acid, disodium EDTA, sodium citrate, disodium EDTA, disodium hydrogen phosphate, sodium dihydrogen phosphate, TRIS, boric acid, borax, and sodium hydroxide.

The test modules 20g comprises a third test modules 203g which is configured to detect pH and comprises a carrier 200g and a detection substance provided on the carrier 200g, wherein the detection substance is formed by mixing a color developer and a surfactant, wherein the color developer comprises one or more of phenol red, sodium phenol red, bromocresol green, sodium bromocresol green, bromophenol blue, bromothymol blue, cresol red, sodium cresol red, and xylenol orange, wherein the surfactant comprises one or more of Tween 20, Tween 80, Span 80, BRIJ 47, polyvinylpyrrolidone K30, polyvinylpyrrolidone K90, polyethylene glycol 4000, polyvinyl alcohol, fatty alcohol ethoxylate, isooctyl alcohol ethoxylate N, and N,N-dimethyloctadecylamine.

The test modules 20g comprises a fourth test modules 204g which is configured to detect cyanuric acid and comprises a carrier 200g and a detection substance provided on the carrier 200g, wherein the detection substance is formed by mixing a color rendering agent, a surfactant and melamine, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, and isooctanol polyoxyethylene ether and N,N-dimethyldioctadecylamine.

The test modules 20g comprises a fifth test modules 205g which is configured to detect total alkalinity and comprises a carrier 200g and a detection substance provided on the carrier 200g, wherein the detection substance is formed by mixing a color rendering agent and a surfactant, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine.

The test modules 20g comprises a sixth test modules 206g which is configured to detect total chlorine and comprises a carrier 200g and a detection substance provided on the carrier 200g, wherein the detection substance is formed by mixing a buffer, a surfactant and a color developer, wherein the buffer comprises one or more of citric acid, sodium citrate, disodium hydrogen phosphate, sodium dihydrogen phosphate, TBS, boric acid, borax, and sodium hydroxide, wherein the surfactant comprises one or more of Tween 20, Tween 80, Span 80, BRIJ47, polyvinylpyrrolidone K30, polyvinylpyrrolidone K90, polyethylene glycol 4000, polyvinyl alcohol, aliphatic alcohol polyoxyethylene ether, isooctanol polyoxyethylene ether, and N,N-dimethyldioctadecylamine, wherein the color developer comprises one or more of DPD, tetramethylbenzidine, syringaldazine, and vanillin azine.

The test modules 20g comprises a seventh test modules 207g which is configured to detect bromine and comprises a carrier 200g and a detection substance provided on the carrier 200g, wherein the detection substance is formed by mixing a color developer, a buffer and a surfactant, wherein the color developer comprises one or more of DPD, tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide, wherein the surfactant comprises one or more of Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether and N, N-dimethyl n-octadecylamine.

The test modules 20g comprises an eighth test modules 208g which is configured to detect lead and comprises a carrier 200g and a detection substance provided on the carrier 200g, wherein the detection substance is formed by mixing a color developer and a buffer, wherein the color developer is xylenol orange, the buffer comprises one or more of citric acid, sodium citrate, glycine, sodium hydroxide. The eight test module 208g can be made by immersing the carrier 200g which is a filtering paper into an immersing solution which is prepared by mixing the color developer and the buffer into a solvent such as ethanol solution and then dry the filtering paper. As a first example of the immersing solution, 1000 ml 50% anhydrous ethanol solution is added with 2.6 g citric acid, 4.3 g sodium citrate, and 1 g xylenol orange. As a second example, 1000 ml 50% anhydrous ethanol solution is added with 1.2 g glycine and 1.5 g xylenol orange. As a third example, 1000 ml 50% anhydrous ethanol solution is added with 1.5 g citric acid, 0.4 g sodium hydroxide and 1.2 g xylenol orange.

The test modules 20g comprises a ninth test modules 209g which is configured to detect iron and comprises a carrier 200g and a detection substance provided on the carrier 200g, wherein the detection substance is formed by mixing a color developer, a reducing agent and a buffer, wherein the color developer is ammonium thiocyanate, the reducing agent comprises one or more of metal elements, phenol, and ascorbic acid, the buffer may comprise citric acid and sodium citrate. The color development principle is that ammonium thiocyanate reacts with divalent iron ions and trivalent iron ions under the catalysis of a reducing agent to generate colored substances. The ninth test module 209g can be made by immersing the carrier 200g which is a filtering paper into an immersing solution which is prepared by mixing the color developer, the reducing agent and the buffer into a solvent and then dry the filtering paper. As a first example of the immersing solution, 3 g citric acid, 10 g sodium citrate, 1 g ammonium thiocyanate, and 1 g of ascorbic acid are added into 500 ml of pure water, and then 500 ml of anhydrous ethanol is added into the mixture. As a second example of the immersing solution, 4 g citric acid, 11 g sodium citrate, 2 g ammonium thiocyanate, and 0.8 g phenol are added into 500 ml pure water, and then 500 ml anhydrous ethanol is added into the mixture.

The test modules 20g comprises a tenth test modules 210g which is configured to detect copper and comprises a carrier 200g and a detection substance provided on the carrier 200g, wherein the detection substance is formed by mixing a color developer, and a buffer, wherein the color developer is 4-(2-pyridyl azo) resorcinol, the buffer may comprise one or more of citric acid, sodium citrate, disodium hydrogen phosphate, sodium dihydrogen phosphate, TRIS, boric acid, borax, sodium hydroxide, hydrochloric acid, nitric acid, sulfuric acid. The tenth test module 210g can be made by immersing the carrier 200g which is a filtering paper into an immersing solution which is prepared by mixing the color developer and the buffer into a solvent and then dry the filtering paper, the color developer is added in an amount of 0.002 g-0.12 g per 100 ml. As a first example of the immersing solution, 0.03 g 4-(2-pyridyl azo) resorcinol is added into 500 ml of ethanol, and then add 400 ml of pure water, and adjust the pH to 4.7 with hydrochloric acid. As a second example of the immersing solution, 0.06 g 4-(2-pyridyl azo) resorcinol is added into 1000 ml of ethanol, and then add 800 ml of pure water, and adjust the pH to 4.8 with citric acid and sodium citrate. As a third example of the immersing solution, 0.03 g 4-(2-pyridyl azo) resorcinol is added into 500 ml of ethanol, and then add 400 ml of pure water, and adjust the pH to 5.0 with disodium hydrogen phosphate, sodium dihydrogen phosphate.

Alternatively, an individual copper test module 210g also can be prepared by the following steps. Prepare a first solution: dissolve 1.0 g of 4-(2-pyridyl azo) resorcinol in 1000 ml of ethanol. Prepare a second solution: dissolve 1.6 g citric acid and 0.3 g sodium citrate in 1000 ml 50% ethanol solution. Immerse the filtering paper in the first solution, and then immerse the filtering pater in the second solution, and finally dry the filtering paper to obtain the finished product.

The test modules 20g comprises an eleventh test modules 211g which is configured to detect nitrite and comprises a carrier 200g and a detection substance provided on the carrier 200g, wherein the detection substance is formed by mixing a color developer, a buffer and a surfactant, wherein the color developer comprises p-aminobenzenesulfonic acid and substances with similar structures or chemical properties, and N-1-naphthylethylenediamine hydrochloride or other similar coupling reagents, the buffer may comprise one or more of citric acid, sodium citrate, disodium hydrogen phosphate, sodium dihydrogen phosphate, TRIS, boric acid, borax, sodium hydroxide. The surfactant may comprise one or more of cationic, anionic, and nonionic surfactants including but not limited to Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine. The color development principle is diazotization coupling reaction, nitrite ions first react with ammonia substances such as p-aminobenzenesulfonic acid to produce diazotization reaction, and then the diazo compound reacts with the color developer to produce color change. The eleventh test module 211g can be made by subsequently immersing the carrier 200g which is a filtering paper into a first solution and a second solution and then dry the filtering paper. As a first example, the first solution is prepared by dissolving 67.56 g citric acid and 20.34 g sodium citrate in 1000 ml 50% anhydrous ethanol, the second solution is prepared by dissolving 6.3 g p-aminobenzenesulfonic acid and 0.56 g N-1-naphthylethylenediamine hydrochloride in 1000 ml 65% anhydrous ethanol. As a second example, the first solution is prepared by dissolving 49.6 g sodium hydrogen phosphate, 62.2 g sodium dihydrogen phosphate in 1000 ml 50% anhydrous ethanol, the second solution is prepared by dissolving 6.5 g p-aminobenzenesulfonic acid 0.6 g N-1-naphthylethylenediamine hydrochloride, and 2 g Tween 20 in 1000 ml 65% anhydrous ethanol.

It is worth mentioning that the addition amount of p-aminobenzenesulfonic acid in the second solution is 1-20 g per 1000 ml, and the addition amount of N-1-naphthylethylenediamine hydrochloride in the second solution is 0.006 g-1.56 g per 1000 m.

The test modules 20g comprises a twelfth test modules 212g which is configured to detect nitrate and comprises a carrier 200g and a detection substance provided on the carrier 200g, wherein the detection substance is formed by mixing a reducing agent and one or more additives, wherein the reducing agent comprises microorganism, enzyme, metal, and organic reducing agent, the additive, which helps the reducing agent to adhere to the carrier 200g, can be but not limited to pure water, anhydrous ethanol, glycerol, gelatin, dimethyl sulfone, gum arabic, Tween 20, Tween 80, Span 80, BRIJ47, polyvinyl pyrrolidone K30, polyvinyl pyrrolidone K90, polyethylene glycol 4000, polyvinyl alcohol, fatty alcohol polyoxyethylene ether, isooctyl alcohol polyoxyethylene ether N, N-dimethyl n-octadecylamine. Based on the nitrite color development principle, an additional step is added in the present invention, a reducing agent is adopted to reduce nitrate to nitrite for detection. The twelfth test module 212g can be made by immersing the carrier 200g which is a filtering paper into an immersing solution and then dry the filtering paper. As a first example of the immersing solution, 3.6 g nitrate reductase and 10 g gelatin are dissolved in 1000 ml water. As a second example of the immersing solution, 10 g zinc powder is dissolved in 1000 ml 50% dimethyl sulfone solution. As a second example of the immersing solution, 68.6 g ascorbic acid is dissolved in 1000 ml water.

The test modules 20g comprises a thirteenth test modules 213g which is configured to detect microplastics (MPS) and comprises a carrier 200g and a detection substance provided on the carrier 200g, wherein the detection substance is formed by mixing a color developer and a buffer, wherein the color developer is N,N-diethyl-p-phenylenediamine (DPD), the buffer comprises boric acid and borax. The thirteenth test module 213g can be made by immersing the carrier 200g which is a filtering paper into an immersing solution and then dry the filtering paper. As an example of the immersing solution, 6.8 g boric acid, 1.2 g borax and 2.2 g DPD are dissolved in 1000 ml 50% anhydrous ethanol solution.

The test modules 20g comprises a fourteenth test modules 214g which is configured to detect nickel and comprises a carrier 200g and a detection substance provided on the carrier 200g, wherein the detection substance is formed by mixing a color developer, a buffer and an oxidant, wherein the color developer is dimethylglyoxime, the buffer includes but not limited to citric acid, sodium citrate, disodium hydrogen phosphate, sodium dihydrogen phosphate, TRIS, boric acid, borax, sodium hydroxidea, and the oxidant comprises one or more of manganese dioxide, potassium dichromate, ferric chloride. The color development principle is that the color developer dimethylglyoxime reacts with oxidizing substances under alkaline conditions to produce colored substances. The fourteenth test module 214g can be made by immersing the carrier 200g which is a filtering paper into an immersing solution and then dry the filtering paper. As an example of the immersing solution, 16.8 g TRIS and 0.15 g manganese dioxide are dissolved in 300 ml pure water to provide a first solution, 0.192 g dimethylglyoxime is dissolved in 700 ml of anhydrous ethanol to provide a second solution, the first solution is then mixed with the second solution to provide the immersing solution. In the present invention, the added amount of the color developer is 0.16 g-3.25 g per 100 ml.

The test modules 20g comprises a fifteenth test modules 215g which is configured to detect phosphate and comprises a carrier 200g and a detection substance provided on the carrier 200g, wherein the detection substance is formed by mixing a color developer, and a reducing agent, wherein the color developer is ammonium molybdate, the reducing agent includes but not limited to microorganisms, enzymes, metals, and organic reducing agents. The color development principle is that in the presence of the reducing agent, orthophosphate reacts with molybdate to produce a blue substance. The fifteenth test module 215g can be made by immersing the carrier 200g which is a filtering paper into an immersing solution and then dry the filtering paper. As an example of the immersing solution, 0.75 g ammonium molybdate and 10.8 g zinc powder are dissolved in in 1000 ml water, the added amount of the reducing agent is 0.6 g-1.78 g per 100 ml.

With reference to FIG. 29, a preparation method of multifunctional detection test paper 1000g comprises the following steps.

Step S91: Provide a base 10g;

The step of providing the base further comprises the following steps:

Provide a base layer 100g, and Form a hydrophobic layer 101g with the base layer 100g.

In this step, the base layer 100g is made of a polymer material such as PET (Polyethylene Terephthalate), PEN (Polyethylene Naphthalate), PP (Polypropylene), and PE (Polyethylene). In this embodiment, the base layer 100g is made of PET. PET is known for its excellent mechanical strength, providing a robust and durable base layer 100g that can withstand handling and environmental stress during use and storage. PET exhibits strong resistance to chemicals, including acids and bases. This characteristic ensures that the base layer 100g does not degrade or react when exposed to various substances, preserving the integrity of the multifunctional detection test paper.

The step of forming the hydrophobic layer 101g comprises the following steps:

Provide a coating solution 102g; and

Coat the coating solution 102g on the base layer 100g to form the base 10g with a hydrophobic layer 101g.

In this step, the coating solution can be mixed by a silicone containing organic compound, a modifying agent and a molding agent.

The silicone containing organic compound can be, but is not limited to, silicon dioxide, dodecylsilane, tetradecylsilane, cetyltrimethoxysilane, octadecylsilane, dimethyloctadecylchlorosilane, methacryloxypropylsilane.

The modifying agent can be, but is not limited to, hydrochloric acid, sulfuric acid, nitric acid, phosphoric acid, acetic acid, oxalic acid, citric acid, salicylic acid.

The molding agent can be, but is not limited to, sodium hydroxide, lithium hydroxide, ammonia, sodium bicarbonate, sodium acetate, sodium citrate, potassium citrate.

As a first example, 0.02 g silicon dioxide, 0.06 g trimethoxysilane, 0.1 g salicylic acid, 100 ml glacial acetic acid, and 0.6 g sodium citrate are dissolved in 1000 ml water. Stir the mixed solution until it is in suspension to obtain the coating solution.

As a second example, 0.002 g octadecylsilane, 10 ml HCl, and 0.06 g NaOH are dissolved in 1000 ml water. Stir the mixed solution until it is in suspension to obtain the coating solution.

As a third example, 2 g silicon dioxide, 200 ml glacial acetic acid, and 2 g sodium acetate are dissolved in 1000 ml water. Stir the mixed solution until it is in suspension to obtain the coating solution.

Further, before coating, the base layer 100g can be preheated, and then the coating solution is evenly coated to the base layer 100g. The hydrophobic layer 101g is formed with the base layer 100g and can be dried to obtain the final base 10g.

The base layer 100g with the hydrophobic layer 101g reduces color mixing.

In this step, in the manufacturing process, both the base layer 100g (such as PET film) and the coating solution are positioned in designated locations within an apparatus. Once positioned, the machine is activated, including its heating mechanism, to begin the process. Following a preheating phase, the base layer 100g is advanced through the system by a traction mechanism, ensuring consistent movement through each stage.

As the base layer 100g moves, the coating mechanism applies an even layer of the coating solution across the entire surface of the base layer 100g. This coating process ensures a uniform distribution, which is essential for the desired hydrophobic properties of the final product. Immediately following the application of the coating solution, the base layer 100g is conveyed through a heating unit, where the coating layer is subjected to rapid drying. This drying phase is completed in a short period, allowing the coating layer to solidify and adhere securely to the base layer 100g surface without impairing its structural integrity.

After passing through the heating unit, the coated base layer 100g is collected and wound by the traction mechanism, forming a roll of the completed product ready for subsequent processing or cutting. This method yields a coated substrate with optimal hydrophobic characteristics and high uniformity, providing enhanced performance in end-use applications.

Step S92: Provide the plurality of test modules 20g, each test module 20g can detect one of pH, total alkalinity, cyanuric acid, total chlorine, bromine, free chlorine water hardness, lead, iron, copper, nitrite, nitrate, MPS, nickle, phosphate.

In this step, the carriers 200g are immersed into different immersing solutions with the corresponding detection substance to obtain the test modules 20g.

Step S93: Attach the test modules 20g to the base 10g to obtain a multifunctional detection test paper.

The final product, once coated and dried, can be cut or trimmed to predetermined dimensions and sizes according to specific requirements.

The present invention further provides a container 400 for storing a plurality of the multifunctional detection test papers, and a plurality of color blocks 4000 are painted on an outer surface of the container 400 for indicating the concentration levels of corresponding substance, as shown in FIG. 28.

In this embodiment, the plurality of color blocks 4000 comprises a set of total hardness color blocks 4001, a set of free chlorine color blocks 4002, a set of bromine color blocks 4003, a set of total chlorine color blocks 4004, a set of cyanuric acid color blocks 4005, a set of total alkalinity color blocks 4006, a set of pH color blocks 4007, a set of lead color blocks 4008, a set of iron color blocks 4009, a set of copper color blocks 4010, a set of nitrite color blocks 4011, a set of nitrate blocks 4012, a set of PMS color blocks 4013, a set of nickel color blocks 4014 and a set of phosphate color blocks 4015.

The total hardness color blocks 4001, the free chlorine color blocks 4002, the bromine color blocks 4003, the total chlorine color blocks 4004, the cyanuric acid color blocks 4005, the total alkalinity color blocks 4006, the pH color blocks 4007, the lead color blocks 4008, the iron color blocks 4009, the copper color blocks 4010, the nitrite color blocks 4011, the nitrate blocks 4012, the PMS color blocks 4013, the nickel color blocks 4014 and the phosphate color blocks 4015 are arranged in order in a vertical row, corresponding to the multiple detection areas on the multifunctional detection test paper.

Each color blocks (4001, 4002, 4003, 4004, 4005, 4006, 4007, 4008, 4009, 4010, 4011, 4012, 4013, 4014 and 4015) include multiple color blocks arranged laterally, with colors gradually shifting to represent variations in concentration levels.

For example, the total hardness color blocks 4001 comprises a first purple-red color block 4001a, a second purple-red color block 4001b, and a third purple-red color block 4001c. The detection result corresponding to the first purple-red color block 4001a is 0.5 mg/L, the detection result corresponding to the second purple-red color block 4001b is 1.0 mg/L, the detection result corresponding to the third purple-red color block 4001c is 3.0 mg/L. The number of color blocks is provided as an example only and may be increased as needed to allow for finer gradation in concentration levels.

For example, the free chlorine color blocks 4002 comprises a first blue color block 4002a, a second blue color block 4002b, and a third blue color block 4002c. The detection result corresponding to the first blue color block 4002a is 0.5 mg/L, the detection result corresponding to the second blue color block 4002b is 1.0 mg/L, the detection result corresponding to the third blue color block 4002c is 3.0 mg/L. The number of color blocks is provided as an example only and may be increased as needed to allow for finer gradation in concentration levels.

For example, the bromine color blocks 4003 comprises a first green color block 4003a, a second green color block 4003b, and a third green color block 4003c. The detection result corresponding to the first green color block 4003a is 0.5 mg/L, the detection result corresponding to the second green color block 4003b is 1.0 mg/L, the detection result corresponding to the third green color block 4003c is 3.0 mg/L. The number of color blocks is provided as an example only and may be increased as needed to allow for finer gradation in concentration levels.

For example, the total chlorine color blocks 4004 comprises a first gray color block 4004a, a second gray color block 4004b, and a third gray color block 4004c. The detection result corresponding to the first gray color block 4004a is 0.5 mg/L, the detection result corresponding to the second gray color block 4004b is 1.0 mg/L, the detection result corresponding to the third gray color block 4004c is 3.0 mg/L. The number of color blocks is provided as an example only and may be increased as needed to allow for finer gradation in concentration levels.

For example, the cyanuric acid color blocks 4005 comprises a first orange color block 4005a, a second orange color block 4005b, and a third orange color block 4005c. The detection result corresponding to the first orange color block 4005a is 0.5 mg/L, the detection result corresponding to the second orange color block 4005b is 1.0 mg/L, the detection result corresponding to the third orange color block 4005c is 3.0 mg/L. The number of color blocks is provided as an example only and may be increased as needed to allow for finer gradation in concentration levels.

For example, the total alkalinity color blocks 4006 comprises a first rose-red color block 4006a, a second rose-red color block 4006b, and a third rose-red color block 4006c. The detection result corresponding to the first rose-red color block 4006a is 0.5 mg/L, the detection result corresponding to the second rose-red color block 4006b is 1.0 mg/L, the detection result corresponding to the third rose-red color block 4006c is 3.0 mg/L. The number of color blocks is provided as an example only and may be increased as needed to allow for finer gradation in concentration levels.

For example, the pH color blocks 4007 comprises a first yellowish-brown color block 4007a, a second yellowish-brown color block 4007b, and a third yellowish-brown color block 4007c. The detection result corresponding to the first yellowish-brown color block 4007a is 6.8, the detection result corresponding to the second yellowish-brown color block 4007b is 7.2 mg/L, the detection result corresponding to the third yellowish-brown color block 4007c is 7.6 mg/L. The number of color blocks is provided as an example only and may be increased as needed to allow for finer gradation in concentration levels.

For example, the lead color blocks 4008 comprises a first color block 4008a, a second color block 4008b, and a third color block 4008c. The detection result corresponding to the first color block 4008a is 20 mg/L, the detection result corresponding to the second color block 4008b is 50 mg/L, the detection result corresponding to the third color block 4008c is 100 mg/L. The number of color blocks is provided as an example only and may be increased as needed to allow for finer gradation in concentration levels.

For example, the iron color blocks 4009 comprises a first color block 4009a, a second color block 4009b, and a third color block 4009c. The detection result corresponding to the first color block 4009a is 2 mg/L, the detection result corresponding to the second color block 4009b is 5 mg/L, the detection result corresponding to the third color block 4009c is 10 mg/L. The number of color blocks is provided as an example only and may be increased as needed to allow for finer gradation in concentration levels.

For example, the copper color blocks 4010 comprises a first color block 4010a, a second color block 4010b, and a third color block 4010c. The detection result corresponding to the first color block 4010a is 0.5 mg/L, the detection result corresponding to the second color block 4010b is 1 mg/L, the detection result corresponding to the third color block 4010c is 3 mg/L. The number of color blocks is provided as an example only and may be increased as needed to allow for finer gradation in concentration levels.

For example, the nitrite color blocks 4011 comprises a first color block 4011a, a second color block 4011b, and a third color block 4011c. The detection result corresponding to the first color block 4011a is 5 mg/L, the detection result corresponding to the second color block 4011b is 10 mg/L, the detection result corresponding to the third color block 4011c is 40 mg/L. The number of color blocks is provided as an example only and may be increased as needed to allow for finer gradation in concentration levels.

For example, the nitrate color blocks 4012 comprises a first color block 4012a, a second color block 4012b, and a third color block 4012c. The detection result corresponding to the first color block 4012a is 10 mg/L, the detection result corresponding to the second color block 4012b is 50 mg/L, the detection result corresponding to the third color block 4012c is 250 mg/L. The number of color blocks is provided as an example only and may be increased as needed to allow for finer gradation in concentration levels.

For example, the MPS color blocks 4013 comprises a first color block 4013a, a second color block 4013b, and a third color block 4013c. The detection result corresponding to the first color block 4013a is 1 mg/L, the detection result corresponding to the second color block 4013b is 6 mg/L, the detection result corresponding to the third color block 4013c is 10 mg/L. The number of color blocks is provided as an example only and may be increased as needed to allow for finer gradation in concentration levels.

For example, the nickel color blocks 4014 comprises a first color block 4014a, a second color block 4014b, and a third color block 4014c. The detection result corresponding to the first color block 4014a is 10 mg/L, the detection result corresponding to the second color block 4014b is 50 mg/L, the detection result corresponding to the third color block 4014c is 100 mg/L. The number of color blocks is provided as an example only and may be increased as needed to allow for finer gradation in concentration levels.

For example, the phosphate color blocks 4015 comprises a first color block 4015a, a second color block 4015b, and a third color block 4015c. The detection result corresponding to the first color block 4015a is 10 mg/L, the detection result corresponding to the second color block 4015b is 50 mg/L, the detection result corresponding to the third color block 4015c is 100 mg/L. The number of color blocks is provided as an example only and may be increased as needed to allow for finer gradation in concentration levels The inclusion of color blocks 4000 directly on the container 400 provides an easy and immediate reference for users to compare the color change of the test paper with the standard color blocks. This feature simplifies the process of interpreting test results, as users can directly compare the test paper to the color blocks on the container 400 without needing a separate reference card.

The color blocks 4000 being painted on the container 400 ensure that the reference guide is always available with the test papers. This design reduces the risk of misplacing or losing the color reference, making the test kit more user-friendly and accessible, especially in field conditions.

Since the color blocks 4000 are painted on the container 400, they are less likely to be damaged or worn compared to a separate paper reference card. This increases the durability of the test kit, ensuring that the reference guide remains intact and legible over time. The color blocks 400 may be painted on an outer surface of the container 400, or the color blocks 400 are painted on a paper sheet and the paper sheet is then attached on the container body of the container 400.

Combining the test paper storage and the color reference in one container makes the entire testing kit more compact and portable. Users can carry the container with them easily, knowing that they have everything needed for water quality testing in one convenient package.

A method of testing water quality can be carried out by a the steps illustrated in FIG. 26, by immersing a plurality of the test modules 20g of a multifunctional detection test paper into water, each of the test modules 20g being configured to detect at least one of a combination of pH, total alkalinity, cyanuric acid, total chlorine, bromine, free chlorine, water hardness, lead, iron, copper, nitrite, nitrate, MPS, nickle, and phosphate.

Figure 30:
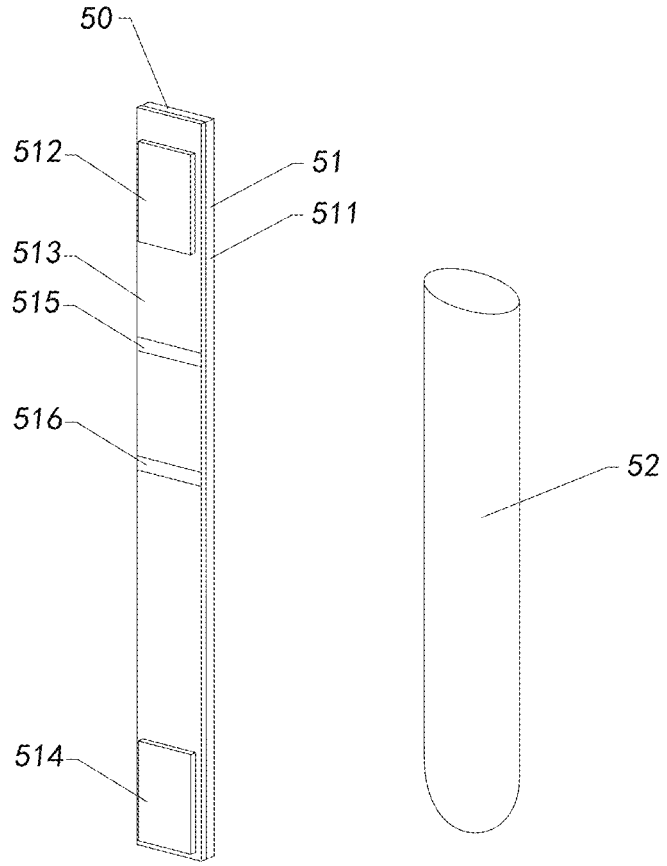
FIG. 30 is a perspective view illustrating a lead detecting unit of the multifunctional detection test kit of according to the above another preferred embodiment of the present invention.

In this embodiment, as shown in FIG. 30, the multifunctional detection test kit comprises a lead detection unit 50 which comprises a lead detection card 51 and a reaction tube 52, the lead detection card 51 comprises a base plate 511 which is made of PVT or PS plastic, a gold label pad 512, a nitrocellulose membrane 513, and an water absorbent paper 514. The base plate 511 is pasted with the nitrocellulose membrane 513, one end of the nitrocellulose membrane 513 is pasted with the gold label pad 512, and the other end is pasted with the water absorbent paper 514. The nitrocellulose membrane 513 is provided with a test strip 515 and a quality control strip 516; the test strip 515 is coated with a lead detection antigen, and the quality control strip 516 is coated with goat anti-mouse IgG. The gold label pad 512 is coated with colloidal gold labeled with a lead monoclonal antibody.

The reaction tube 52 is equipped with a chelating agent, which includes but is not limited to ethylenediaminetetraacetic acid, disodium ethylenediaminetetraacetic acid, dipotassium ethylenediaminetetraacetic acid, benzyl ethylenediaminetetraacetic acid, diethylenetriaminepentaacetic acid or a combination thereof. The amount added to each reaction tube 52 is 10 μl-300 μl (concentration 0.01-0.1 mmol/L).

In the preparation of colloidal gold labeled with lead monoclonal antibody, AuNPs (Gold nanoparticle) are prepared using a reducing agent known to those skilled in the art. In this example, ascorbic acid is used. More specifically, chloroauric acid is dissolved in double distilled water to a final concentration of 0.003% to 0.6%, and 0.25 to 3.5 mL 1% ascorbic acid solution is added to the above solution and mixed evenly. Lead monoclonal antibody is added to colloidal gold to a final concentration of 1-10 μg/ml, and the remaining active sites are blocked by protein. The protein is casein, bovine serum albumin, soy protein, or a combination thereof, and the addition amount is 1% to 10%.

In the preparation of the gold label pad 512, the glass cellulose membrane needs to be immersed in a treatment solution known to those skilled in the art in advance for treatment and dried. Then the colloidal gold solution or its dilution labeled with lead monoclonal antibody is sprayed on the treated glass cellulose membrane and dried to obtain the gold label pad 512.

In the process of nitrocellulose membrane coating, the prepared test strip 515 and the quality control strip 516 are streaked on the nitrocellulose membrane 513. As an example, in the order from left to right, the test strip 515 and the quality control strip 516 are arranged, and set aside after drying; the test strip 515 is lead antigen, prepared with 0.01M buffer to a concentration of 0.3-3.5 mg/ml (the buffer can be tris or phosphate); the quality control strip 516 is goat anti-mouse IgG, with a concentration of 0.2-5 mg/ml.

During assembly of the test strip 515, cut the prepared gold label pad 512, the nitrocellulose membrane 513 and the water absorbent paper 514 into rectangles of different widths and assemble them in an overlapping manner. The gold label pad 512 and the water absorbent paper 514 should press the nitrocellulose membrane 513 for about 2-3 mm each.

In the lead detection process, the water sample is added into the reaction tube 52 which is added with the chelating agent to react to obtain a sample solution. After the sample solution is added to the sample application well of the lead detection paper 51, the heavy metal lead in the sample solution binds to the gold-labeled antibody, preventing the gold-labeled antibody from binding to the heavy metal lead conjugate on the nitrocellulose membrane 513.

If the heavy metal lead content in the sample solution exceeds the detection limit, the test line corresponding to the position of the test strip 515 does not show color or appears significantly lighter than the control line corresponding to the position of the quality control strip 516.

If the heavy metal lead content in the sample solution is below the detection limit, the test line corresponding to the position of the test strip 515 appears darker than the control line corresponding to the position of the quality control strip 516.

Figure 31:
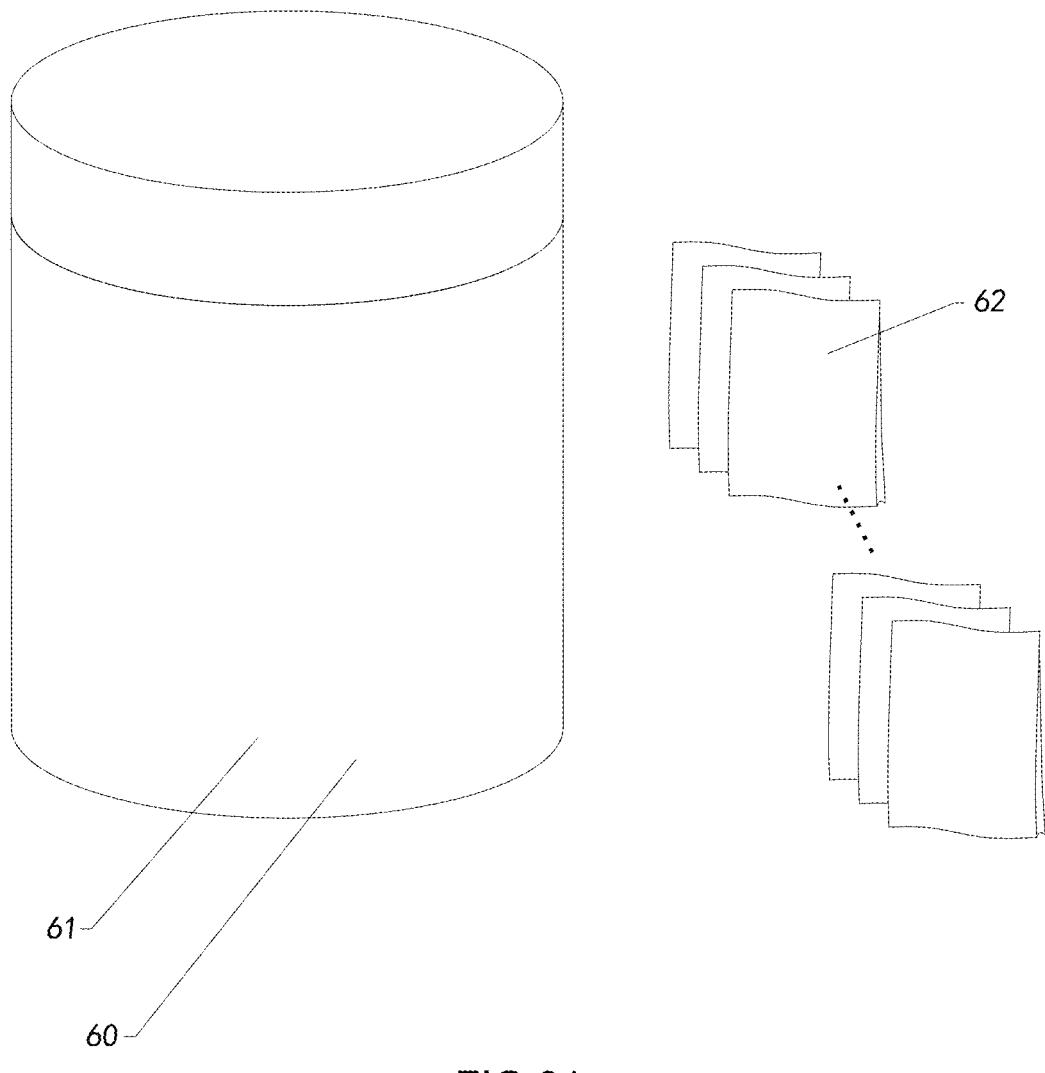
FIG. 31 is a perspective view illustrating a total coliform bacteria detection unit of the multifunctional detection test kit of according to the above another preferred embodiment of the present invention.

In this embodiment, as shown in FIG. 31, the multifunctional detection test kit further comprises a total coliform bacteria detection unit 60 which comprises a storing container 61, a plurality of dosage containers 62 stored in the storing container 61 for storing the detection substance.

Total coliform bacteria are cultured at 36° C.±1° C. for 24 hours to ferment lactose to produce acid and gas which can be detected. Detection of total coliform bacteria requires nutrients, chemical buffers, indicators. The nutrients comprises but not limited to glucose, maltose, lactose, corn starch, potato starch, wheat starch, hydrolyzed fatty acids, sodium acetate, ammonium sulfate, sodium nitrate, peanut cake powder, soybean cake powder, cottonseed cake powder, corn steep liquor, yeast powder, fish meal, silkworm pupa powder, and peptone. The buffer comprises one or more of sodium chloride, potassium chloride, ammonium chlorides. The indicator comprises one or more of bromocresol purple, bromophenol red, chlorophenol red, phenol red, phenol red sodium, bromocresol green, bromocresol green sodium, bromophenol blue, bromothymol blue, cresol red, cresol red sodium, and xylenol orange.

As an example, 15 g peanut powder, 3 g fishmeal, 8.9 g sodium chloride and 35 mg bromophenol blue ethanol solution are evenly mixed and then is packed into one hundred dosage container 62 to provide one hundred testing elements. According to the present invention, the added amount of the nutrients is 1.2 g-18 g for the one hundred testing elements, the added amount of the buffer is 1.6 g-28 g for the one hundred testing elements, and the added amount of the indicator is 0.002 g to 0.16 g for the one hundred testing elements.

The above is one or more implementation methods provided in combination with the specific content, and it is not intended that the specific implementation of the present invention is limited to these descriptions. Anything similar to or identical to the method, structure, etc. of the present invention, or a number of technical deductions or substitutions made on the premise of the concept of the present invention, should be regarded as the scope of protection of the present invention.

What is claimed is:

1. A multifunctional detection test kit for water, comprising:

a multifunctional detection test paper which comprises a base and a plurality of test modules, wherein the base comprises a base layer and a hydrophobic layer formed on a surface of the base layer, wherein the hydrophobic layer has a plurality of test zones spaced apart from each other;

wherein the test modules are provided on the test zones of the hydrophobic layer respectively to separate the test modules from the base layer;

wherein the test modules are configured to detect at least one of pH value, total alkalinity, cyanuric acid, total chlorine, bromine, free chlorine water hardness, lead, iron, copper, nitrite, nitrate, microplastics, nickel, and phosphate;

wherein the base layer is made of Polyethylene Terephthalate;

wherein the hydrophobic layer is formed by coating a coating solution on the base layer, wherein the coating solution is a mixture of an organosilicon compound, a modifying agent and a molding agent, wherein the organosilicon compound comprises one or more of dodecylsilane, tetradecylsilane, cetyltrimethoxysilane, octadecylsilane, dimethyloctadecylchlorosilane, and methacryloxypropylsilane, wherein the modifying agent comprises one or more of hydrochloric acid, sulfuric acid, nitric acid, phosphoric acid, acetic acid, oxalic acid, citric acid, and salicylic acid, wherein the molding agent comprises one or more of sodium hydroxide, lithium hydroxide, ammonia, sodium bicarbonate, sodium acetate, sodium citrate, and potassium citrate.

2. The multifunctional detection test kit, as recited in claim 1, wherein one of the test modules is configured to detect free chlorine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises one or more of DPD (N, N-diethyl-p-phenylenediamine), tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide.

3. The multifunctional detection test kit, as recited in claim 2, wherein one of the test modules is configured to detect total alkalinity and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color rendering agent and a surfactant for immersing the carrier and then drying the carrier, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

4. The multifunctional detection test kit, as recited in claim 1, wherein one of the test modules is configured to detect water hardness and comprises a carrier attached onto one of the test zones of the hydrophobic layer and a detection substance immersed into the carrier in order to carry the detection substance on the hydrophobic layer and to separate the detection substance from the base layer, wherein the detection substance is formed by immersing the carrier in an immersing solution containing a color developer and a buffer and then drying the carrier, wherein the color developer comprises one or more of calcium magnesium reagent, chrome black T, calcium carboxylic acid, azo arsine 1, and azo arsine 3, wherein the buffer comprises one or more of citric acid, disodium EDTA, sodium citrate, disodium hydrogen phosphate, sodium dihydrogen phosphate, TRIS, boric acid, borax, and sodium hydroxide.

5. The multifunctional detection test kit, as recited in claim 1, wherein one of the test modules is configured to detect pH value and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a surfactant for immersing the carrier and then drying the carrier, wherein the color developer comprises one or more of phenol red, sodium phenol red, bromocresol green, sodium bromocresol green, bromophenol blue, bromothymol blue, cresol red, sodium cresol red, and xylenol orange.

6. The multifunctional detection test kit, as recited in claim 1, wherein one of the test modules is configured to detect cyanuric acid and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color rendering agent, a surfactant and melamine for immersing the carrier and then drying the carrier, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange.

7. The multifunctional detection test kit, as recited in claim 1, wherein one of the test modules is configured to detect total chlorine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a buffer, a surfactant and a color developer for immersing the carrier and then drying the carrier, wherein the buffer comprises one or more of citric acid, sodium citrate, disodium hydrogen phosphate, sodium dihydrogen phosphate, TBS, boric acid, borax, and sodium hydroxide, wherein the color developer comprises one or more of DPD (N, N-diethyl-p-phenylenediamine), tetramethylbenzidine, syringaldazine, and vanillin azine.

8. The multifunctional detection test kit, as recited in claim 1, wherein one of the test modules is configured to detect bromine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises one or more of DPD (N, N-diethyl-p-phenylenediamine), tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide.

9. The multifunctional detection test kit, as recited in claim 1, wherein one of the test modules is configured to detect lead and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is xylenol orange, the buffer comprises one or more of citric acid, sodium citrate, glycine, sodium hydroxide.

10. The multifunctional detection test kit, as recited in claim 1, wherein one of the test modules is configured to detect iron and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a reducing agent and a buffer for immersing the carrier and then drying the carrier, wherein the color developer is ammonium thiocyanate, the reducing agent comprises one or more of metal elements, phenol, and ascorbic acid, the buffer comprises citric acid and sodium citrate.

11. The multifunctional detection test kit, as recited in claim 1, wherein one of the test modules is configured to detect copper and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is 4-(2-pyridyl azo) resorcinol, the buffer comprises one or more of citric acid, sodium citrate, disodium hydrogen phosphate, sodium dihydrogen phosphate, TRIS, boric acid, borax, sodium hydroxide, hydrochloric acid, nitric acid, sulfuric acid.

12. The multifunctional detection test kit, as recited in claim 1, wherein one of the test modules is configured to detect nitrite and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises p-aminobenzenesulfonic acid and N-1-naphthylethylenediamine hydrochloride, the buffer comprises one or more of citric acid, sodium citrate, disodium hydrogen phosphate, sodium dihydrogen phosphate, TRIS, boric acid, borax, sodium hydroxide.

13. The multifunctional detection test kit, as recited in claim 1, wherein one of the test modules is configured to detect nitrate and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a reducing agent and one or more additives for immersing the carrier and then drying the carrier, wherein the reducing agent comprises one or more of microorganism, enzyme, metal, and organic reducing agent.

14. The multifunctional detection test kit, as recited in claim 1, wherein one of the test modules is configured to detect microplastics and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is N,N-diethyl-p-phenylenediamine (DPD), the buffer comprises boric acid and borax.

15. The multifunctional detection test kit, as recited in claim 1, wherein one of the test modules is configured to detect nickel and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and an oxidant for immersing the carrier and then drying the carrier, wherein the color developer is dimethylglyoxime, the buffer comprises one or more of citric acid, sodium citrate, disodium hydrogen phosphate, sodium dihydrogen phosphate, TRIS, boric acid, borax, sodium hydroxide, and the oxidant comprises one or more of manganese dioxide, potassium dichromate, ferric chloride.

16. The multifunctional detection test kit, as recited in claim 1, wherein one of the test modules is configured to detect phosphate and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a reducing agent for immersing the carrier and then drying the carrier, wherein the color developer is ammonium molybdate, the reducing agent comprises one or more of microorganisms, enzymes, metals, and organic reducing agents.

17. The multifunctional detection test kit, as recited in claim 1, wherein the test modules are configured to detect pH value, total alkalinity, cyanuric acid, total chlorine, bromine, free chlorine water hardness, lead, iron, copper, nitrite, nitrate, microplastics, nickel, and phosphate;

wherein the test modules comprise a first test module which is configured to detect free chlorine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises one or more of N,N-diethyl-p-phenylenediamine (DPD), tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide;

wherein the test modules comprise a second test module which is configured to detect water hardness and comprises a carrier attached onto one of the test zones of the hydrophobic layer and a detection substance immersed into the carrier in order to carry the detection substance on the hydrophobic layer and to separate the detection substance from the base layer, wherein the detection substance is formed by immersing the carrier in an immersing solution containing a color developer and a buffer and then drying the carrier, wherein the color developer comprises one or more of calcium magnesium reagent, chrome black T, calcium carboxylic acid, azo arsine 1, and azo arsine 3, wherein the buffer comprises one or more of citric acid, disodium EDTA, sodium citrate, disodium EDTA, disodium hydrogen phosphate, sodium dihydrogen phosphate, TRIS, boric acid, borax, and sodium hydroxide;

wherein the test modules comprise a third test module which is configured to detect pH value and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a surfactant for immersing the carrier and then drying the carrier, wherein the color developer comprises one or more of phenol red, sodium phenol red, bromocresol green, sodium bromocresol green, bromophenol blue, bromothymol blue, cresol red, sodium cresol red, and xylenol orange;

wherein the test modules comprise a fourth test module which is configured to detect cyanuric acid and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color rendering agent, a surfactant and melamine for immersing the carrier and then drying the carrier, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange;

wherein the test modules comprise a fifth test module which is configured to detect total alkalinity and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color rendering agent and a surfactant for immersing the carrier and then drying the carrier, wherein the color rendering agent comprises one or more of phenol red, phenol red sodium, bromocresol green, bromocresol green sodium, bromophenol blue, bromocresol purple, bromothymol blue, cresol red, cresol red sodium, and dimethylphenol orange;

wherein the test modules comprise a sixth test module which is configured to detect total chlorine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a buffer, a surfactant and a color developer for immersing the carrier and then drying the carrier, wherein the buffer comprises one or more of citric acid, sodium citrate, disodium hydrogen phosphate, sodium dihydrogen phosphate, TBS, boric acid, borax, and sodium hydroxide, wherein the color developer comprises one or more of DPD (N, N-diethyl-p-phenylenediamine), tetramethylbenzidine, syringaldazine, and vanillin azine;

wherein the test modules comprise a seventh test module which is configured to detect bromine and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises one or more of N,N-diethyl-p-phenylenediamine (DPD), tetramethylbenzidine, syringaldehyde azine, and vanillin azine, wherein the buffer comprises one or more of citric acid, sodium citrate, disodium hydrogen phosphate, sodium dihydrogen phosphate, TRIS, boric acid, borax and sodium hydroxide;

wherein the test modules comprise an eighth test module which is configured to detect lead and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is xylenol orange, the buffer comprises one or more of citric acid, sodium citrate, glycine, sodium hydroxide;

wherein the test modules comprise a ninth test module which is configured to detect iron and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a reducing agent and a buffer for immersing the carrier and then drying the carrier, wherein the color developer is ammonium thiocyanate, the reducing agent comprises one or more of metal elements, phenol, and ascorbic acid, the buffer comprises citric acid and sodium citrate;

wherein the test modules comprise a tenth test module which is configured to detect copper and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is 4-(2-pyridyl azo) resorcinol, the buffer comprises one or more of citric acid, sodium citrate, disodium hydrogen phosphate, sodium dihydrogen phosphate, TRIS, boric acid, borax, sodium hydroxide, hydrochloric acid, nitric acid, sulfuric acid;

wherein the test modules comprise an eleventh test module which is configured to detect nitrite and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and a surfactant for immersing the carrier and then drying the carrier, wherein the color developer comprises p-aminobenzenesulfonic acid and N-1-naphthylethylenediamine hydrochloride, the buffer comprises one or more of citric acid, sodium citrate, disodium hydrogen phosphate, sodium dihydrogen phosphate, TRIS, boric acid, borax, sodium hydroxide;

wherein the test modules comprise a twelfth test module which is configured to detect nitrate and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a reducing agent and one or more additives for immersing the carrier and then drying the carrier, wherein the reducing agent comprises one or more of microorganism, enzyme, metal, and organic reducing agent;

wherein the test modules comprise a thirteenth test module which is configured to detect microplastics and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a buffer for immersing the carrier and then drying the carrier, wherein the color developer is N,N-diethyl-p-phenylenediamine (DPD), the buffer comprises boric acid and borax;

wherein the test modules comprise a fourteenth test module which is configured to detect nickel and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer, a buffer and an oxidant for immersing the carrier and then drying the carrier, wherein the color developer is dimethylglyoxime, the buffer comprises one or more of citric acid, sodium citrate, disodium hydrogen phosphate, sodium dihydrogen phosphate, TRIS, boric acid, borax, sodium hydroxide, and the oxidant comprises one or more of manganese dioxide, potassium dichromate, ferric chloride;

wherein the test modules comprise a fifteenth test module which is configured to detect phosphate and comprises a carrier attached onto one of the test zones of the hydrophobic layer and a detection substance immersed into the carrier in order to carry the detection substance on the hydrophobic layer and to separate the detection substance from the base layer, wherein the detection substance is formed by mixing a color developer and a reducing agent for immersing the carrier and then drying the carrier, wherein the color developer is ammonium molybdate, the reducing agent comprises one or more of microorganisms, enzymes, metals, and organic reducing agent.

18. The multifunctional detection test kit, as recited in claim 1, further comprising a lead detection unit which comprises a lead detection card and a reaction tube, wherein the lead detection card comprises a base plate, a gold label pad, a nitrocellulose membrane, and a water absorbent paper, wherein the base plate is pasted with the nitrocellulose membrane, one end of the nitrocellulose membrane is pasted with the gold label pad, and the other end thereof is pasted with the water absorbent paper, wherein the gold label pad and the water absorbent paper are separated from the base plate by the nitrocellulose membrane, wherein the nitrocellulose membrane is provided with a test strip and a quality control strip, wherein the test strip and the quality control strip are provided on the nitrocellulose membrane between the gold label pad and the water absorbent paper, wherein the test strip is coated with a lead detection antigen, and the quality control strip is coated with goat anti-mouse IgG, wherein the gold label pad is coated with colloidal gold labeled with a lead monoclonal antibody, wherein the reaction tube is equipped with a chelating agent which comprises one or more of ethylenediaminetetraacetic acid, disodium ethylenediaminetetraacetic acid, dipotassium ethylenediaminetetraacetic acid, benzyl ethylenediaminetetraacetic acid, and diethylenetriaminepentaacetic acid.

19. The multifunctional detection test kit, as recited in claim 1, further comprising a total coliform bacteria detection unit which comprises a plurality of dosage containers each is storing a detection substance which comprises a nutrient, a chemical buffer, and an indicator, wherein the nutrient, the chemical buffer, and the indicator are mixed and packed in each of the dosage containers, wherein the nutrient comprises one or more of glucose, maltose, lactose, corn starch, potato starch, wheat starch, hydrolyzed fatty acids, sodium acetate, ammonium sulfate, sodium nitrate, peanut cake powder, soybean cake powder, cottonseed cake powder, corn steep liquor, yeast powder, fish meal, silkworm pupa powder, and peptone, wherein the chemical buffer comprises one or more of sodium chloride, potassium chloride, ammonium chlorides, wherein the indicator comprises one or more of bromocresol purple, bromophenol red, chlorophenol red, phenol red, phenol red sodium, bromocresol green, bromocresol green sodium, bromophenol blue, bromothymol blue, cresol red, cresol red sodium, and xylenol orange.

\* \* \* \* \*